US005834233A

United States Patent [19]
Molin et al.

[11] Patent Number: 5,834,233
[45] Date of Patent: Nov. 10, 1998

[54] METHOD OF LIMITING THE SURVIVAL OF GENETICALLY ENGINEERED MICROORGANISMS IN THEIR ENIVRONMENT

[75] Inventors: Soren Molin, Holte; Michael Givskov, Copenhagen; Claus Sternberg Kristensen, Copenhagen N., all of Denmark; Asim K. Bej, Birmingham, Ala.; Leo Eberl, Graz, Austria

[73] Assignee: GX BioSystems A/S, Copenhagen, Denmark

[21] Appl. No.: 544,822

[22] Filed: Oct. 18, 1995

Related U.S. Application Data

[63] Continuation-in-part of Ser. No. 135,665, Oct. 13, 1993, abandoned, which is a continuation of Ser. No. 863,261, Nov. 6, 1992, abandoned.

[51] Int. Cl.$^6$ .......................... C12P 21/02; C12N 15/31; C12N 15/32; C12N 15/63
[52] U.S. Cl. ...................... 435/69.1; 435/172.3; 435/243; 435/320.1; 536/23.2; 536/23.71
[58] Field of Search ................................ 435/69.1, 172.3, 435/320.1, 243; 536/23.2, 23.71

[56] References Cited

U.S. PATENT DOCUMENTS

| | | | |
|---|---|---|---|
| 4,743,546 | 5/1988 | Lackman et al. | 435/108 |
| 4,948,735 | 8/1990 | Luria et al. | 435/252.8 |
| 5,086,169 | 2/1992 | Mascarenhas | 536/23.6 |

FOREIGN PATENT DOCUMENTS

| | | |
|---|---|---|
| WO8606743 | 11/1986 | WIPO . |
| 8607608 | 12/1986 | WIPO . |
| 8705932 | 10/1987 | WIPO . |
| WO8705932 | 10/1987 | WIPO . |
| 9117256 | 11/1991 | WIPO . |

OTHER PUBLICATIONS

DePalma Genetic Engineering News p. 27, Apr. 1, 1992.
Henschke et al. Biol. Fertil. Soils vol. 11 301–305, 1991.
Lamy et al. Nucleic Acids Res. vol. 18 1001–1006, 1991.
Cacciapuoti et al. Infection and Immunity vol. 20 418–420, 1978.
Elmros et al. J. Bacteriol. vol. 126 969–976, 1976.
Fox Bt cotton infestations renew resistance concerns. Nature Biotechnology vol. 14 1070, 1996.
Molin et al. Suicidal genetic elements and their use on biological containment of bacteria. Ann. Rev. Microbiol. vol. 47 139–166, 1993.
Tucker, Philip W. et al., "Staphylococcal nuclease reviewed: a prototypic study in contemporary enzymology"; Molecular & Cellular Biochemistry, vol. 23, No. 3, pp. 131–141 (09 Feb. 1979).
Hiraga, Sota, et al., *Chromosome Partitioning in Escherichia coli: Novel Mutants Producing Anucleate Cells,* Journal of Bacteriology, vol. 171, pp. 1496–1505, Mar. 1989.

Abstract, dialog Information Services, Biosis, Dialog Accession No. 716771, Biosis No. 88084516, of Atlas RM et al. Approaches for Monitoring . . . into the Environment, *Hazard Waste Hazard Mater.* 6:135–144 (1989).
Abstract, dialog Information Services, Medline, Dialog Accession No. 07722794, Medline accession No. 91241794 of Knudsen SM et al., "Development of efficient suicide mechanisms . . . ", Appl. Environ. Microbiol., 57 (1) pp. 85–92 (1991).
Bogo–Jensen, L. et al., "A Substrate–Dependent Biological Containment System for *Pseudomas putida* Based on the *Escherichia coli gef* Gene", Applied and Environmental Microbiology, 59:3713–3717 (Nov. 1993).
Depalma, Angelo, "GX Biosystems Targets Various Markets with its Suicide Gene Technology", *Genetic Engineering News*, Apr. 1, 1992.
Neidhardt, Frederick C., et al., eds., *Escherichia Coli and Salmonella Typhimurim: Cellular and Molecular Biology,* American Society for Microbiology, vol. 1, pp. 1190–1219.
Poulsen, L.K. et al., "The gef gene from *Escherichia coli* is regulated at the level of translation", *Molecular Microbiology,* 5(7)1639–1648 (1991).
Silhavy, Thomas J., et al., "Experiments with Gene Fusions", xi–xii, (1984).
Amann, et al.; Vectors being a hybrid trp–lac promoter useful for regulated expression of cloned gene in *E. coli*; Gene 25:167–178 (1983).
Poulsen, et al.; A family of genes encoding a cell–killi be conserved in all gram–negative ba Mol. Microl. 3(11):1463–1472 (1989).
Chang, et al.; Construction and Characterization of Amplifiable Multicopy DNA Cloning Vehicles Derived from the P15A Cryptic Miniplasmid.
Birnboim and Doly; A rapid alkaline extraction procedure for screening recombinant plasmid DNA Nucleic Acids Research 7(6):1513–1523 (1979).
Csonka and Clark; Deletions generated by the transposon Tn10 in the srl recA regin of the *E. coli* K–12 chromosome; Genetics 93:321–343 (1979).
Herrero, et al.; Transposon vectors containing non–antibiotic resistance selection markers for cloning and stable chromosomal insertion of foreign genes in gram–negative bacteria; J. Bacteriol. 172(11):6557–67 (1990).

(List continued on next page.)

*Primary Examiner*—James Ketter
*Assistant Examiner*—John S. Brusca
*Attorney, Agent, or Firm*—Iver P. Cooper

[57] ABSTRACT

The survival of cells is limited by introducing into the cells a regulatably expressible gene whose expression results in the formation of a cytoplasmatically active hydrolytic enzyme. Populations of cells containing, in addition to such a regulatably expressible gene, a DNA coding for a pesticidally active or environmental pollutant-degrading gene product, may be useful in pesticidally active compositions and environmental pollutant-degrading compositions, respectively.

125 Claims, 43 Drawing Sheets

OTHER PUBLICATIONS

Lanzer, et al.; Promoters largely determine the efficiency of repressor action Proc. Natl. Acad. Sci. USA 85:8973–8977 (Dec. 1988).

Schneider and Beck; New Expression for identifying and testing signal structures for initiation and termination and transcription; Methods in Enzymology 155:452–461 (1987).

deLorenzo, et al.; Mini–Tn5 transposon derivatives for insertion mutagenesis, promoter probing, and chromosomal insertion of cloned DNA in gram–negative eubacteria; J. Bacteriol. 172(11):6568–6572 (1990).

Sanger, et al.; DNA sequencing with chain–terminating inhibitors Proc. Natl. Acad. Sci. USA 74(12):5463–5467 (1977).

Givskov, et al.; Cloning and expression in E. coli of the gene for extracellular phospholipase A1 from serratia liquefaciens; J. Bacteriol. 170(12):5855–5862 (1988).

Boros, et al.; High–copy–number derivatives of the plasmid cloning vector pBR322 Gene 30:257–260 (1984).

Nilsson, et al.; An improved positive selection plasmid vector constructed by oligonucleotide mediated mutagenesis; Nucleic Acid Research 11(22):8019–8030 (1983).

Grinter, et al.; Two mechanisms necessary for the stable inheritance of plasmid RP4 Plasmid 22:203–214 (1989).

Gerlitz, et al.; Partitioning of broad–host–range plasmid RP4 is a complex system involving site–specific recombination; J. Bacteriol. 172(11):6194–6203 (1990).

Roberts, et al.; Genetic characterization of the stabilizing functions of a region of broad–host–range plasmid RK2; J. Bacteriol. 172(11):6204–6216 (1990).

Eberl, et al.; The divergent promoters mediating transcription of the par locus of plasmid RP4 are subject to autoregulation; Mol. Microbiol. 6(14):1969–79 (1992).

Muller–Hill, B.; LAC repressor and LAC operator Prog. Biophys. Molec. Biol. 30(2/3):227–252 (1975).

Boyer, et al.; A complementation analysis of the restrictin and modification of DNA in E. coli J. Mol. Biol. 41:459–472 (1969).

Birnboim and Doly; A rapid alkaline extraction procedure for screening recombinant plasmid DNA Nucl. Acids Res. 7(6):1513–23 (1979).

Bradford, Marion; A rapid and sensitive method for the quantitation of microgram quantities of protein utilizing the principle of protein–dye binding; Anal. Biochem. 72:248–254 (1976).

Bachmann, Barbara; Derivations and genotypes of some mutant derivatives of E. coli K12 Dept. of Human Genetics 1190–1219 (1987).

Ono, et al.; Nucleotide sequence of the pnd gene in plasmid R483 and role of the pnd gene product in plasmolysis; Microbiol. Immunol. 31(11):1071–1083 (1987).

Bech, et al.; Sequence of the relB transcription unit from E. coli and identification of the relB gene EMBO Journal 4(4):1059–1066 (1985).

Akimoto, et al.; Nucleotide sequence of the F plasmid gene srnB that promotes degradation of stable RNA in E. coli; FEMS Microbiol. Lett. 33:241–45 (1986).

Sakikawa, et al.; The pnd gene in E. coli plasmid R16: Nucleotide sequence and gene expression leading to cell $Mg^{2+}$ release and stable RNA degradation; Biochim. Biophys. Acta. 1007:158–166 (1989).

Shortle, David; A genetic system for analysis of staphylococcal nuclease Gene 22:181–189 (1983).

Bolivar, F.; Construction and characterization of new cloning vehicles: Derivatives of plasmid pBR322 carrying unique EcoRI sites for selection of EcoRI generated recombinant DNA molecules Gene 4:121–136 1978).

Brosius, et al.; Construction and fine mapping of recombinant plasmids containing the rrnB ribosomal RNA operon of E. coli; Plasmid 6:112–118 (1981).

Squires, et al.; Nucleotide sequence at the end of the gene for the RNA polymerase β subunit (rpoC) Nucleic Acid Research 9(24):6827–40 (1981).

Simon, et al.; A broad host range mobilization system for in vivo genetic engineering: Transposon mutagenesis in gram negative bacteria; Biotechnology 1:784–790 (1983).

Humphreys, et al.; Mutagenesis of plasmid DNA with hydroxylamine: Isolation of mutatns of multi–copy plasmids Molec. gen. Genet. 145:101–108 (1976).

Stark, Michael; Multicopy expression vectors carrying the lac repressor gene for regulated high–level expression of genes in E. coli; Gene 51:255–267 (1987).

Yanisch–Perron, et al.; Improved M13 phage cloning vectors; Gene 33:103–119 (1985).

Brosius and Holy; Regulation of ribosomal RNA promoters with a synthetic lac operator Proc. Natl. Acad. Sci. USA 81:6929–6933 (1984).

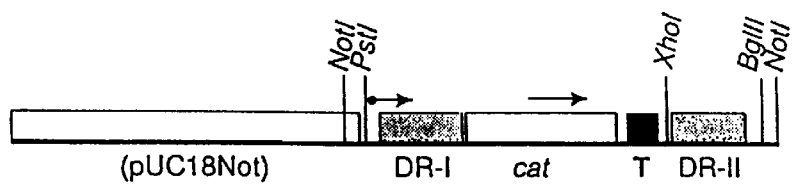
pCK81
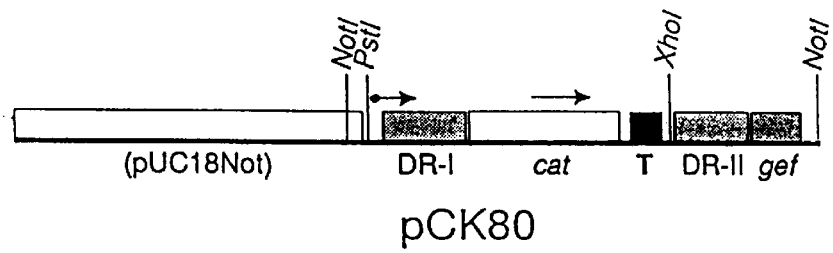
pCK80
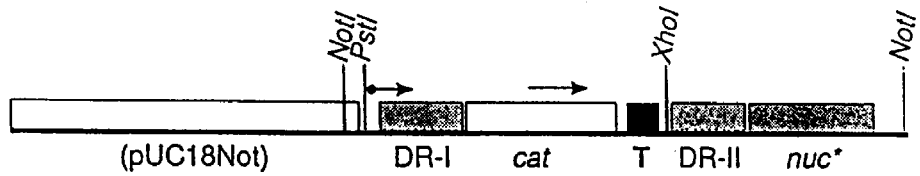
pCK95
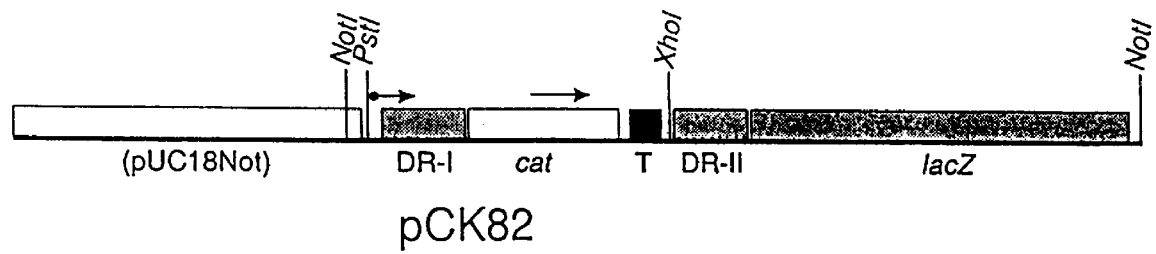
pCK82
Fig. 9

```
CGTAACCGGC TAGTTGCGGC CGCTGCCAGC CATTTGCCAC TCTCCTTTTC ATCCGCATCG GCAGGGTCAT

CCGGGCGCAT CCACCACTCC TGATGCAGTA ATCCTACGGT GCGGAATGTG GTGGCCTCGA AATTCTGTCA

TAAAGTTGTC ACGGCCGAGA CTTATAGTCG CTTTGTTTTT ATTTTTTAAT GTATTTGTAC ATGGAGAAAA
```

|       | GTG | AAA | CAA | ACG | ACT | ATT | GCA | CTG | GCA | CTC | TTA | CCG | TTA | CTG | TTT | ACC | CCT | GTG |
|TAAA   |F-Met|Lys  |Gln  |Ser  |Thr  |Ile  |Ala  |Leu  |Ala  |Leu  |Leu  |Pro  |Leu  |Leu  |Phe  |Thr  |Pro  |Val  |

ACA AAA GCC
Thr Lys Ala 10                                                    20
GCA ACT TCA ACT AAA AAA TTA CAT AAA GAA CCT GCG ACT TTA ATT AAA GCG ATT GAT GGT
Ala Thr Ser Thr Lys Lys Leu His Lys Glu Pro Ala Thr Leu Ile Lys Ala Ile Asp Gly

↓       30                                          ↓   40
GAT ACG GTT AAA TTA ATG TAC AAA GGT CAA CCA ATG ACA TTC AGA CTA TTA TTG GTC GAC
Asp Thr Val Lys Leu Met Tyr Lys Gly Gln Pro Met Thr Phe Arg Leu Leu Leu Val Asp
                Ase I                                                       Sal I
                                 50                                          60
ACA CCT GAA ACA AAG CAT CCT AAA AAA GGT GTA GAG AAA TAT GGT CCT GAA GCA AGT GCA
Thr Pro Glu Thr Lys His Pro Lys Lys Gly Val Glu Lys Tyr Gly Pro Glu Ala Ser Ala

↓             70              ↓                               80
TTT ACC AAA AAA ATG GTA GAA AAT GCA AAG AAA ATT GAA GTC GAA TTC GAC AAA GGT CAA
Phe Thr Lys Lys Met Val Glu Asn Ala Lys Lys Ile Glu Val Glu Phe Asp Lys Gly Gln
            Bst XI                                       Eco RI
                               ↓  90                           100
AGA ACT GAT AAA TAT GGA CGT GGG CTA GCG TAT ATT TAT GCT GAT GGA AAA ATG GTA AAC
Arg Thr Asp Lys Tyr Gly Arg Gly Leu Ala Tyr Ile Tyr Ala Asp Gly Lys Met Val Asn
                                Nhe I
↓                                 110                                     120
GAA GCT TTA GTT CGT CAA GGC TTG GCT AAA GTT GCT TAT GTT TAC AAA CCT AAC AAT ACA
Glu Ala Leu Val Arg Gln Gly Leu Ala Lys Val Ala Tyr Val Tyr Lys Pro Asn Asn Thr
Hind III
                                130                                    ↓  140
CAT GAA CAA CAT TTA AGA AAA AGT GAA GCA CAA GCG AAA AAA GAG AAA TTA AAT ATT TGG
His Glu Gln His Leu Arg Lys Ser Glu Ala Gln Ala Lys Lys Glu Lys Leu Asn Ile Trp
                                                                       Ssp I AGC GAA GAC AAC GCT GAT TCA GGT CAA TAA TGCTCATTGT AAAAGTGTCA CTGCTGCTAG TGGCAC
Ser Glu Asp Asn Ala Asp Ser Gly Gln

Fig. 30

METHOD OF LIMITING THE SURVIVAL OF GENETICALLY ENGINEERED MICROORGANISMS IN THEIR ENIVRONMENT

This application is a continuation-in-part of U.S. application Ser. No. 08/135,665, filed Oct. 13, 1993, now abandoned, which is a continuation of U.S. application Ser. No. 07/863,261, filed Apr. 16, 1992, now abandoned. Both prior applications and all references cited herein, are hereby incorporated by reference in their entirety.

FIELD OF INVENTION

The present invention provides a novel system of biological containment of genetically engineered microorganisms. The invention relates to a cell or a population hereof containing a regulatably expressible gene whose expression results in the formation of a cytoplasmatically active hydrolytic enzyme at a rate which leads to cell function limitation; to a recombinant replicon containing such a regulatably expressible gene; to methods of limiting the survival of a population of cells containing the expressible gene, to a method of containing an extrachromosomal recombinant replicon to a first kind of cells and of stochastically limiting the survival of a cell population.

There is also provided an immunologically active composition, a pesticidal composition and an environmental pollutant-degrading composition, all of which contain a cell population as defined above wherein the cells further contain a DNA sequence coding for a gene product which is immunologically active, pesticidally active or environmental pollutant-degrading, respectively.

TECHNICAL BACKGROUND

The increasing application of recombinant DNA technology to engineer novel microorganisms which are industrially useful have caused concerns in both the scientific community and the general public over potential risks. These concerns are primarily related to the potential harm to humans and to undesirable and/or uncontrollable ecological consequences upon deliberate or unintentional release of such genetically engineered microorganisms (GEMS) into the environment. These concerns have led to the establishment of official guidelines for the safe handling of GEMs in laboratories and production facilities where such organisms are applied. Up till now, such guidelines have primarily been directed to measures of physically containing GEMs in laboratories and production facilities with the aim of reducing the likelihood that workers in such facilities were contaminated, or that the GEMs were to escape from their primary physical environment, such as a fermentation vessel.

It is presently being recognized that the level of safety in the handling of GEMs can be increased by combining physical containment measures with biological containment measures to reduce the possibility of the survival of the genetically engineered organisms if they were to escape from their primary environment.

Lately, however, concerns have become increasingly focused on potential risks related to deliberate release of GEMs to the outer environment and to the use of GEMs as live vaccines. In this connection there is a strongly felt need to have biological containment systems which subsequent to the environmental release of the GEMs or their administration as vaccines to a human or an animal body, effectively kill the released organisms in a controlled way or which limit the function of the released GEMs to an extent where such GEMs are placed at a significant competitive disadvantage whereby they will eventually be ousted by the natural microflora of the environment to which they are released.

The first systems of biological containment were based on the use of "safe" cloning vectors and debilitated host bacteria. As examples, it has been suggested to select vectors which lack transfer functions or which naturally have a very narrow host range. Examples of debilitated host bacteria are *E. coli* mutants having an obligate requirement for exogenous nutrients not present or present in low concentrations outside the primary environment of the GEMs.

Other suggested biological containment systems have been based on mechanisms whereby the vector is restricted to the GEMs e.g. by using a plasmid vector with a non-sense mutation in a gene, the expression of which is indispensable for plasmid replication, or a suppressor mutation in the chromosome, said mutation blocking translational readthrough of the message of the gene. A further approach is to maintain the rDNA stably in the host by integrating it into the chromosomes of the GEMs.

Recently, an alternative biological containment strategy has been developed in which the recombinant vector is endowed with a gene encoding a cell killing function which gene is under the control of a promoter only being expressed under certain environmental conditions, such as conditions prevailing in an environment outside the primary environment of the GEMs, or when the vector is unintentionally transferred to a secondary host, or the expression of which is stochastically induced. By using incorporation in a GEM of such a cell killing function and selecting appropriate regulatory sequences, vectors can be constructed which are contained in the primary host cell and/or in a primary physical environment. A cell killing function as hereindefined may also be referred to as an active biological containment factor.

If a stochastically induced mechanism of expression regulation is selected for such a biological containment system, a population of GEMs containing the system will, upon release to the outer environment, or if used as a live vaccine, be subjected to a random cell killing which will lead to an increase of the doubling time of the host cell population or eventually to the disappearance of the organisms.

The above-mentioned genes encoding cell killing functions are also frequently referred to as "suicide" genes, and biological containment systems based upon the use of such genes, the expression of which are regulated as defined above, are commonly described as conditional lethal systems or "suicide" systems. Up till now, several cell killing functions have been found in bacterial chromosomes and in prokaryotic plasmids. Examples of chromosomal genes having cell killing functions are the gef (Poulsen et al., 1991) and relF (Bech et al., 1985) genes from *E. coli* K-12. Examples of plasmid encoded suicide genes are hok and flmA (Gerdes et al., 1986) genes isolated from plasmids R1 and F, respectively, the snrB gene also isolated from plasmid F (Akimoto et al., 1986) and the pnd gene isolated from plasmids R16 and R483 (Sakikawa et al., 1989 and Ono et al., 1987). Common features of these genes are that they are transcribed constitutively, regulated at a post-transcriptional level, and that they all encode small toxic proteins of about 50 amino acids. The application of the hok gene in a biological containment system has been disclosed in WO 87/05932.

Ideally, the features of an effective biological containment system should include as a minimum requirement that the cell killing function when it is expressed, is effective, that the containment system is functional in a broad range of species of GEMs, that the risk of elimination of the cell killing function e.g. by mutations in the suicide gene or the sequences regulating the expression of the gene, is minimal and that the risk of uptake by other organisms of rDNA released when cells are killed, is reduced.

None of the above-mentioned known containment systems fulfil all of these ideal requirements. However, the present invention provides a novel active biological containment system which is not based on a primary cell killing function but which makes use of genes, the expression of which in a cell where the gene is inserted, results in the formation of mature forms of exoenzymes which are hydrolytically active in the cytoplasm of the cell and which can not be transported over the cell membrane. When such enzymes are expressed, the normal function of the cell becomes limited to an extent whereby the competitiveness, and hence the survival, of a population of such cells is reduced significantly.

In this connection, it has been observed that although an exoenzyme such as a bacterial nuclease encoded by a gene from which the sequence coding for the signal peptide has been totally removed may be entirely suitable in a method of limiting the survival of GEMs in accordance with the above, a certain transport of the nuclease out of the cell comprising such a gene without the signal sequence-coding sequence may cause "leakage" of active enzyme out of the cell, thereby reducing the efficiency of this containment system. However, it has surprisingly been found that this problem can be overcome if a truncated and/or mutated form of a nuclease is used. Additionally, a significant increase in the cytoplasmic enzymatic activity of such a modified enzyme relative to a parent nuclease has been provided thus resulting in further improved methods of limiting the survival of GEMS. Accordingly, the hydrolytically active enzyme of the invention includes such a truncated and/or mutated form of a nuclease. Provided the hydrolytically active enzyme is an RNA-degrading and/or DNA-degrading enzyme, a biological containment system based upon such an enzyme may have a further advantage over the known biological containment systems in that the rDNA molecules in a genetically engineered host cell is destroyed simultaneously with the genetically altered host microorganisms.

As an example, a recombinant staphylococcal nuclease according the invention having endonucleolytic activity will when used in accordance with the invention cause hydrolysis of the DNA and the RNA to 3'-phosphomononucleotides. However, it may from a GEM risk point of view be advantageous to provide the GEM containment system in a form where further intracellular degradation of the damaged nucleic acids is provided. This may e.g. be provided by inserting into the GEMs a further gene coding for a 3'-5'exonucleolytically active exonuclease. The simultaneous expression and the successive degradative activities of a endonuclease such as the above modified staphylococcal nuclease and an exonuclease will cause complete destruction of the host nucleic acids, thus killing the host strain without having its nucleic acids remaining stable in the environment for an unlimited period of time.

SUMMARY OF THE INVENTION

Many cells produce hydrolytically active enzymes which are inherently translocated extracellularly, i.e. the enzymes are excreted over the cell membrane. When expressed intracellularly in a cell naturally producing such enzymes, the enzymes are in the form of enzymatically inactive, immature exoenzyme molecules (proenzymes) comprising a signal peptide by means of which the proenzyme is transportable over the cell membrane. On passage of the cell membrane, the signal peptide is cleaved off the molecules which are thereby turned into the mature, enzymatically active form.

The present invention is based on the discovery that an exoenzyme including a truncated and/or mutated form hereof which normally, while present in the cytoplasm of cells producing them, are in the form of the immature, enzymatically inactive proenzyme may be expressed in a cell in the form of the mature enzyme being enzymatically active in the cytoplasm of the cell and that the presence intracellularly of such active forms of exoenzymes causes damages to the cells leading to a limitation of the normal cell function.

On the basis of these findings, the present invention provides a novel approach to biological containment of GEMs aiming at limiting the survival hereof in their environment.

Thus, in a first aspect, the present invention provides a cell containing a gene whose expression results in the formation of an enzyme which is present and hydrolytically active in the cytoplasm of said cell, the cell further containing a regulatory nucleotide sequence which regulates the expression of the gene, the expression of said gene leading to formation of the enzyme in the cell at a rate which results in the hydrolysis of hydrolysable cytoplasmic substances necessary for non-limited function of the cell, to an extent whereby the function of the cell is being limited.

In a further aspect, there is provided a recombinant replicon containing a regulatably expressible gene which, when expressed in a cell encodes an enzyme which is present and hydrolytically active in the cytoplasm of the cell, the expression of said gene leading to formation of the enzyme in the cell at a rate which results in the hydrolysis of hydrolysable cytoplasmic substances necessary for non-limited function of the cell, to an extent whereby the function of the cell is being limited, the expression of said genes being regulated by a regulatory nucleotide sequence which is contained in the recombinant replicon or in an other recombinant replicon present in a cell containing the replicon.

In a still further aspect, the present invention relates to a population of cells consisting of a multiplicity of cells as defined above.

Additionally, the present invention relates to a method of limiting the survival of a cell population in a first or a second environment which method comprises transforming the cells of said population with a recombinant replicon being replicated in the cells of the population and containing a gene whose expression results in the formation of an enzyme which is present and hydrolytically active in the cytoplasm of said cell, the cells further containing a regulatory nucleotide sequence being regulatable by an environmental factor and which regulates the expression of said gene, the expression of said gene leading to formation of the enzyme in the cells at a rate which results in the hydrolysis of hydrolysable cytoplasmic substances necessary for non-limited function of the cell, to an extent whereby the function of the cells is being limited leading to a limitation of the survival of the cell population.

In another aspect, the invention relates to a method of containing an extrachromosomal recombinant replicon to a first kind of cell, where said replicon is naturally transferable to a second kind of cell, which method comprises providing on the recombinant extrachromosomal replicon a gene whose expression results in the formation of an enzyme which is present and hydrolytically active in the cytoplasm of a cell, the formation of said enzyme being at a rate which results in the hydrolysis of hydrolysable cytoplasmic substances necessary for non-limited function of the cell, to an extent whereby the function of the cell is being limited, said first kind of cells having or being modified to have a chromosomal replicon comprising a regulatory nucleotide sequence which inhibits the expression of said gene and thereby protects said first kind of cells, said regulatory gene being lacking in said second kind of cell, whereby, if a cell of the second kind receives said extrachromosomal recombinant replicon said gene is expressed and has a function-limiting effect thereon.

In another further aspect, the present invention pertains to a method of stochastically limiting the survival of a cell population which comprises transforming the cells thereof with a recombinant replicon containing a regulatably expressible gene which, when expressed in a cell encodes an enzyme which is present and hydrolytically active in the cytoplasm of the cell, the expression of said gene leading to formation of the enzyme in the cell at a rate which results in the hydrolysis of hydrolysable cytoplasmic substances necessary for non-limited function of the cells, to an extent whereby the function of the cells is being limited, the expression of said genes or genes being stochastically induced as a result of recombinational excision of an excisable negatively functioning regulatory nucleotide sequence which, while present in the cells, inhibits expression of the gene coding for the enzyme, said negatively functioning regulatory nucleotide sequence being contained in the recombinant replicon or in an other recombinant replicon present in cells of the population containing the replicon.

In a still further aspect, there is provided an immunologically active composition which contains a viable function-limited cell population as defined above wherein the cells contain a further DNA sequence not naturally related to the gene coding for the hydrolytically active enzyme or to the regulatory nucleotide sequence, which further sequence is a sequence coding for an immunologically active gene product, the cells being function-limited to an extent which, when the composition is administered to a human or an animal, allows the cells to express the immunologically active gene product for a period of time and in an amount sufficient to obtain an effective immune response in said human or animal, but which does not allow the cells to persist in the human or the animal.

The present invention also provides a pesticidally active composition which contains a viable cell population as defined herein wherein the cells contain a further DNA sequence not naturally related to the gene coding for the hydrolytically active enzyme or to the regulatory nucleotide sequence, which further sequence is a sequence coding for a pesticidally active gene product, the cells being function-limited to an extent which, when the composition is administered to an environment containing a pest, allows the cells to express the pesticidally active gene product for a period of time and in an amount sufficient to obtain an effective pesticidal effect in said environment but which does not allow the cells to persist in the environment.

Finally, there is provided an environmental pollutant-degrading composition which contains a viable cell population as defined herein, wherein the cells contain a further DNA sequence not naturally related to the gene coding for the hydrolytically active enzyme or to the regulatory nucleotide sequence, which further sequence is a sequence coding for an environmental pollutant-degrading gene product, the cells being function-limited to an extent which, when the composition is administered to an environment containing a pollutant to be degraded, allows the cells to express said pollutant degrading gene product for a period of time and in an amount sufficient to obtain an effective pollutant-degrading effect in said environment but which does not allow the cells to persist in the environment.

DETAILED DISCLOSURE OF THE INVENTION

The Concept of an Active Biological Containment System Based on the Use of an Intracellularly Hydrolytically Active Exoenzyme which has a Cell Function-Limiting Effect A number of macromolecules such as proteins, lipids, phospholipids, DNA, RNA and polysaccharides that cannot pass cell membranes are nevertheless utilizable as substrates for cell growth. These substrates are enzymatically hydrolysed (degraded) in the external medium of the cells by protein enzymes excreted by the cells. Such hydrolytic enzymes that mediate extracellular degradation are termed "exoenzymes". In addition to true exoenzymes which are capable of passing the outer cell membrane and hence excreted into the external medium, certain cells produce incompletely excreted hydrolytic enzymes of which some enter the cell membrane and remain there rather than passing through. Others pass through the cell membrane but not the outer membrane (periplasmic enzymes) and still others remain in the outer membrane.

In the present context, the term "exoenzyme" is used to designate a hydrolytic enzyme which has been excreted naturally by the cell natively producing the enzyme or a cell in which the genes coding for such an excretable enzyme have been inserted, by passing through the cell membrane (the cytoplasmic membrane) and accordingly, this term includes native true exoenzymes, cell membrane-bound enzymes, periplasmically located enzymes and outer membrane-bound enzymes.

Generally, the mechanisms by which excretable exoenzymes as defined herein are excreted share common features. Thus, when first synthesized in the cytoplasm, these proteins are in the form of enzymatically inactive precursor molecules (also referred to as proenzymes) which are larger than they are after they have entered their proper extracellular location, since a portion of the amino-terminal end of the protein which is termed the signal peptide, is removed after the protein is properly located. The function of the signal peptide is to aid in the translocation of the protein exoenzyme to its place of location. When the molecule is properly located, the signal peptide is removed whereby the protein is turned into the mature or "processed", enzymatically active hydrolytic enzyme.

However, certain hydrolytically active exoenzymes including the Serratia species phospholipase as defined herein, are not provided with a signal peptide when expressed in a cell naturally producing the enzyme. In addition to the phlA gene encoding the phospholipase, the Serratia cells in which the phospholipase is naturally expressed contain a phlB gene encoding an intracellularly active protein which by interacting with the phospholipase protein render the cells refractory to damages from the phospholipase expressed in the cells.

As explained above, the present invention presents a novel approach to the concept of active biological containment which is based on the finding that it is possible to obtain in the cytoplasm of a cell, i.e. intracellularly, the presence of enzymatically active mature forms of exoenzymes. This is obtained by the insertion in the cell of a nucleotide sequence which codes for the exoenzyme molecule, but which does not comprise the sequence coding for the corresponding native signal peptide herefor. By deletion from the nucleotide sequence of the sequence coding for the signal peptide it is also obtained that the intracellularly active enzyme molecule cannot be translocated outside the cell membrane.

In accordance with the explanation above, an alternative way of obtaining an intracellularly active exoenzyme is to provide in a cell according to the invention, the gene coding for a hydrolytically active exoenzyme without the presence of a gene encoding a gene product which may render the cell refractory to the intracellular activity of said enzyme.

The cytoplasm of cells contains a mixture of macromolecules, the presence and function of which are necessary for the non-limited function of the cells, including basic life manifestations such as growth and replication. Examples of such macromolecules include DNA, RNA, lipids, phospholipids, proteins and polymeric carbohydrates.

When, in accordance with the present invention, a gene whose expression results in the formation of an exoenzyme as defined above is inserted into the cell, naturally occurring intracellular macromolecules may act as substrate for the intracellularly active hydrolytic enzyme.

Provided the hydrolytically active enzyme is expressed intracellularly at a rate which results in the hydrolysis of hydrolysable cytoplasmic macromolecules to an extent whereby the life functions of the cells become limited, the competitiveness of such cells with cells of the same type, but in which an exoenzyme as defined herein is not expressed in intracellularly active forms, will be decreased.

In the present context, the term "non-limited cell function" denotes that the growth of a cell as manifested i.a. by the synthesis of new cell material and the rate of replication of the cell is not decreased by an intracellular hydrolytic macromolecule degradation, not natively occurring in the cells. Accordingly, this term is used herein to describe i.a. the growth rate and the rate of replication, under any given conditions, of a cell in which an intracellularly active exoenzyme as defined above is not being expressed. Consequently, the term "limited cell function" as used herein describes, in a relative manner, the state of a cell in terms of i.a. a reduced growth rate and/or reduced rate of replication which results from the expression therein of an intracellularly active exoenzyme when the cell is grown under the same conditions as a cell of the same kind having a non-limited cell function as defined above.

The recognizable manifestation of such limited cell function may ultimately be cell death, but it may also, relative to a cell having a non-limited cell function, be a reduced cell growth appearing as a reduced rate of replication resulting in a reduced increase of cell numbers within a certain period of time as a result of an increase of the lag phase and/or of the cell doubling time. Other manifestations may be a relatively increased requirement for one or more nutrient components or a relatively higher susceptibility to detrimental environmental factors such as sub-optimal temperatures or cell damaging caused by toxic substances.

The actual type of manifestation or manifestations of such limited cell function and the degree hereof will depend in particular on the specific species of the exoenzyme being expressed in the cell, the rate of expression of the exoenzyme, the capability of the enzyme to be hydrolytically active under the conditions prevailing in the cytoplasm, the amounts of substrate macromolecules, and the significance of such macromolecules for non-limited function of the cell, and the number of copies of the gene encoding the intracellularly active exoenzyme.

The Intracellularly Hydrolytically Active Exoenzyme Having Cell Function-Limiting Effect In accordance with the invention, a suitable intracellularly active exoenzyme may be any exoenzyme which, when it is expressed, is capable of hydrolytically degrading macromolecules present in the cytoplasm of prokaryotic and eucaryotic cells to an extent whereby the function of the cell is being limited. Interesting hydrolytic enzymes which are useful in the present invention include nucleases, phospholipases, lipases, lysozyme, proteases and carbohydrases. As mentioned above, hydrolytic enzymes according to the invention also include truncated and/or mutated forms of nucleases such as truncated and/or mutated Staphylococcus aureus nucleases.

As used herein, the term "nuclease" denotes hydrolytic exoenzymes capable of degrading nucleic acids. The nucleic acids DNA and RNA are polynucleotides formed by the joining of nucleotides by phosphodiester bonds. Some nucleases are capable of degrading both DNA and RNA, whereas others (deoxyribonucleases or DNases) degrade only DNA and still others degrade only RNA (ribonucleases or RNases). Nucleases may either be exonucleases which are diesterphosphate bond-hydrolysing enzymes cleaving off the last nucleotide residue in either of the two terminals of an oligonucleotide, or endonucleases which cleave phosphodiester bonds located in the interior of polynucleotides. In the art, the term "nick" is normally used to describe the lesion in a DNA strand resulting from an endonuclease cleavage of a diesterphosphate bond. It must be noted that term "exonuclease" when used in the present specific context denotes the mode of action as defined above and thus, the term is not used here to designate a nuclease normally being excreted out of the cell.

In the context of the present invention, useful nucleases include nucleases having the capability of hydrolysing diesterphosphate bonds in DNA. Particularly useful DNA-degrading nucleases include endonucleases, the activity of which, when double-stranded DNA is the substrate, results in the cleavage of diesterphosphate bonds (nicks) in only one of the strands of the DNA. Accordingly, in one embodiment of the invention, the hydrolytically active enzyme is an endonuclease including a staphylococcal endonuclease having such capability. Lesions in the DNA occur spontaneously in all cells with a relatively high frequency. However, in the normal cell such lesions are efficiently eliminated by an inherent DNA repair mechanism which involves that the altered portion of the damaged strand is recognized and removed by one set of enzymes and then replaced in its original form by a DNA polymerase, and finally an enzyme called DNA ligase seals the nick (the broken diesterphosphate bond) that remains in the DNA helix, to complete the restoration of an intact DNA strand.

This natural cell DNA repair mechanism will also eliminate DNA lesions (nicks) which may result from the enzymatic activity in a cell of a nuclease as defined herein. Accordingly, the function of a cell in which the intracellularly active nuclease as defined above, is expressed will only be limited when the nuclease is expressed at a rate which results in the presence of nicks in the cell nucleic acids in a number exceeding the number which can be repaired by the DNA repair mechanism, so that the number of DNA lesions (nicks) reaches a level whereby the function of the cell becomes recognizably limited.

The rate of expression of the intracellularly active exoenzyme as defined herein including a nuclease is also determined by the specific activity of the enzyme under the conditions prevailing in the cytoplasm of the cell. It will be understood that these conditions may differ from those prevailing in the extracellular environment into which the enzyme when present in a cell where it is normally produced, is translocated. As one example, an enzyme comprising sulphur-containing amino acid residues such as cysteine and methionine will be prone to damages caused by oxidation and hence, it may be assumed that it will be at least partially enzymatically inactive when present in the cytoplasm of a cell where the $E_h$-value is high. However, it was surprisingly found in the course of research leading to the present invention that an enzyme comprising sulphur-containing amino acids such as an endonuclease containing several cysteine residues may be enzymatically active intracellularly to an extent whereby the function of a cell in which the enzyme is expressed, is limited. Accordingly, in one embodiment of the invention, the hydrolytically active enzyme is an enzyme such as a nuclease, containing at least one sulphur-containing amino acid residue.

Several prokaryotic cells including gram-negative and gram-positive bacteria inherently produce exoenzymes which are translocated over the cell membrane, interesting examples being endonucleases produced by Serratia spp. It is known that such endonucleases have a high specific activity extracellularly. In WO 86/06743 are disclosed such extracellular Serratia spp. nucleases being expressed in *E. coli* and their usefulness in the removal of nucleic acids from biological materials is described. One example of a Serratia spp. nuclease is an enzyme encoded by the following DNA sequence (SEQ ID NO:1), excluding the sequence coding for the N-terminal signal peptide:

GCAGCAACCTCTCTATCCTCCGTCATCCTTATACGTTGAACAACAGCACCAAGTTCGCCAACTGGGTGGCTTATCACATCACCAAAGACACACCCCCCGACACCCTCGAATCCATCGACAACTGCGCGGTCGGCTGTGCCCGACCGGCGGCA
CGTCGTTCCACAGATAGCACGCAGTACGCAGTATGCGAATACGGCAACCTTGTTGTTCCGGTGTTCAAGCGGTTGACCCACCGGATTACACTGGCGCCAACGCGGCTGAAGGCCGGGCTGTCCGAGCTTACCTCTTGACGCGCCAGCCGCTGGCCGCCGT
GGCCAGGCGGCAAGACGGCAACTGGAAAACGATCCGGCGCTCAACCCGGCGGACACGTTGGCGCCGCCGTTACACTGGCGCCAACGCGGCTGAAGGCCGGGCTGTCCGAGCTTACCTCTTGACGCGCCAGCCGCTGGCCGCCGT
CCGGTCGCCCGTTCTGCGCCGGTCTGACCTTTTGGCTAGGCCGAGTTGGGCCGCCCTGTGCAACCGCGGGCCCCCTAATGTGACCGCGGTTGCGCCGCGACTTC

GTCGATCGGTCATCAGGCGGCCGCTCGGCCTCTCCCGGCTGGGAATCCCTGAATTACCTGTCTCCAACATCACGCCGCAAAAGTCCGATC
CACCTAGCGCCAGTCCGGGCGACCGGAGCCGACCCTTTAATGGAGCCCTTAGCGACTTGACACCTTGTAGTGCCCCGTTTCAGGCTAG
TTAACCAGGGCCCCTGGGGCGCGGCTGGAAGATCAGGAACGCAAGCTGATCGATCGCCGATATCTCCCTGCCTCTATACCGTGACCGGGCCGCTGTATGA
AATTGGTCCCGCGGACCCCCCGCCGACCTTCTAGTCCTTGCGTTCGACTAGCGCGGCTATAGAGAGCACTGGCCCGGACTACT

ACGCGGATATGGCAAACTCCCGGCACCCAGAAAGCGCACACCATCCCCAGCCCTACTGGAAGGTGATTTTCATCAACAACCCCGGTGAACCAC
TCCGCTATACCCGTTTGACGGCCCGTGGGTCTTCGCGTGTAGGGGGTCGCGGATGACCTTCCACTAAAAGTAGTTGTGTCGGGCCCCACTTGGTG
TATGCCGCTTTCCTGTTCGATCAGAACACGCCGAAGGGCGCCGATTTCTGCCAATTCCGCGTTGGACGGAGATCGAGAAACGCACCGGCCTGATCA
ATACGGCGAAAGGACAAGCTAGTCTTGTCCGGCTTCCCGGGCTAAAGACGGTTAAGACGCCACCTGCTCTACCCTCTTTGCGTGGCCGGACTAGT

TCTGGCCGGGTCTGCCGGACGTGCAGGCTTCGCTGAAGAGCCTCCTGCCGGACT
AGACCCGGCCAGACGGCCTCCTGCACGCGTCCGAAGCGACTTCTCGTTTGGCCGCAGGACGCCCTCA

It has now been found that such a Serratia spp. nuclease when expressed intracellularly in accordance with the present invention in the form of the mature enzyme, i.e. without the signal peptide, is enzymatically active to an extent whereby the function of the cell in which the enzyme is expressed, is limited. Accordingly, in useful embodiments of the invention, the gene whose expression results in the formation of an intracellularly hydrolytically active enzyme is a gene coding for a Serratia spp. nuclease without its native signal peptide. Further suitable nucleases may be nucleases encoded by genes isolated from other gram-negative bacteria including Aeromonas spp. or Yersinia spp.

In other embodiments of the invention, the hydrolytically active enzyme is a nuclease encoded by a gene isolated from a gram-positive bacterial species such as a Staphylococcus species, one suitable example hereof being the mature form of the nuclease of the Foggi strain of *Staphylococcus aureus*. The gene encoding this enzyme has been cloned and characterized (Shortle, 1983, Gene, 22, 181–189). This nuclease is a $Ca^{2+}$-activated 16.8 kD thermostable extracellular phosphodieterase which degrades both DNA and RNA. The enzyme consists of 149 amino acids with no disulphide bonds or free sulfhydryl groups. The gene encoding this nuclease may be derived from plasmid pFOG408 or plasmid pFOG301 containing the gene.

During the experimentation leading to the present invention, it has been found that a staphylococcal nuclease including the above nuclease of the *Staphylococcus aureus* (Foggi) strain may be hydrolytically active even in a truncated form, i.e. in a form where amino acid residues have been deleted from the N-terminal or the C-terminal end of the wild type enzyme, or from both ends. Examples of such truncated hydrolytically active enzymes are nucleases encoded by the plasmids pSNUC24–26 and pSNUC420–26 as described hereinbelow. Such truncated enzymes may have improved characteristics as compared to the parent enzymes from which they are derived.

Such improved characteristics may include higher specific activity, higher intracellular stability, no or very low transport of the enzyme out of the cell.

Accordingly, in other useful embodiments of the present invention the hydrolytically active enzyme is in a truncated form. As an example, such a truncated enzyme may be a staphylococcal endonuclease, for example lacking at least 9 amino acid residues of the parent enzyme.

Such a truncated staphylococcal nuclease may even maintain its enzymatical functionality when further modified relative to the parent enzyme. Thus, such a truncated nuclease may be mutated in one or more codons by substitution of at least one nucleotide or it may be modified by insertion of DNA sequences in the coding sequence for the truncated enzyme. Furthermore, it was found that deletions of one or more nucleotides may occur in the coding sequence without impairing the function of the enzyme, even when such a deletion causes a frameshift mutation.

Another interesting hydrolytically active enzyme which in accordance with the present invention may be useful as a cell function-limiting enzyme, is a phospholipase such as e.g. a phospholipase coded for by a gene isolated from a Serratia spp. As one specific example hereof may be mentioned the phospholipase disclosed in WO 86/06743 and which is encoded by the following nucleotide sequence (SEQ ID NO:2):

```
ATGAGTATGCCTTTAAGTTTTACCTCTGCAGTATCCCCCCTGGCCGCCATCCCTACCCCTCGCGCCGCTCCCGAGACGCGGACGG
TACTCATACGGAAATTCAAAATGGAGACCTCATAGGGCCCACCGGCGCTAGGGATCCGGAGCGCGGCGACGGCTCTGCGCCTGCC

CGGCGAGCCTCCGGCACCCCCGCAAATCCGGGCCCGTCCCCTCTCCCTCTCAGAACACGCTGAACGCGCAGAATCTGTTCAATACGCTGGTCGGCGATAT
CCCGCTCGGACGCCGTCCCCCCGTTTAGGCCCGGCCACCGGAGAGGGAGACTCTTGTCCGACTTGCGCGTCTTAGACAACTTATCCCACCAGCCGCTATA

CTCAGCGGCCCCACCGACGGCGGCCGCAGCGCCGGGCGTGACGCGGGGGCAGCAATCGCAGGAGGGGGATTATGCGTTGGCGCTGTTCGCCAAGGACGTT
GAGTCCCCGCCGTCGCTGCCGCCGCCGTCCCCGCCCGCACTGCGCCCCCGTCGTTAGCGTCCTCCCCCTAATACGCAACCGCGACAACCGGTTCCTGCAA

TACTCACTCAATCCCCAGGGCGCCGCCGGGTTCAACCGCCTGAGCGACAGCGCGCTGCTCGGTTTCGGCATCGATCCCCCCAGCCTGCACGACCCGCGCA
ATGAGTGAGTTACCGGTCCCGCGGCGGCCCAAGTTGGCCGACTCGCTGTCGCCCGACGAGCCAAAGCCGTAGCTAGGGCCGTCCGACGTGCTGCGCCCGT

CCCCTTTCCAGGCTGGGATTTACAGCAACCACAAACACTATGTGTTGGCCTTCGCCCCCACCAACGACTGGCGCGATTCGCTGACCAACGTGCGGCACCC
CCCCAAACGTCCGACCCTAAATGTCGTTCCTGTTTGTCATACACAACCGCAAGCCCCCGTGGTTGCTGACCGCCCTAACCCACTCGTTCCACGCCGTCCG
GACGGGCTATGACGATGTCCAGTACAATGAGGCCGTTCCCGCTGCCAAAACCCGCCAAGGCCCCCTTCGGCCATGCGCTGGTGATCGCCGGCCATTCCCT
CTGCCCGATACTGCTACACGTCATCTTAGTCCCCCAACGGCGACGGTTTTCGGCGGTTCCGCCGGAAGCCCCTACGCGACCACTAGCGGCCGGTAAGCGA

TCGCGGTGGTCTGGCGGCCACCGCCGCGCTGGCGACCCCCACCGTCGCGGTCACCTTCAACGCGGCCGGCGTCTCGGATTACACCCTGAATCGCCTGGGC
ACCGCCACCAGACCGCCGGTGGCGGCCCGACCGCTGGCCGTGGCAGCGCCAGTGGAAGTTGCGCCGGCCCCAGAGCCTAATGTGGGACTTAGCGGACCCG

ATCGATCCGGCGGCAGCGAAGAAAGATGCCGAAGCCGGCGGCATTCGCCGTACAGCGACCAATATGACATGCTGACCAGCACCCAGGACTCGACCTCGCT
TAGCTAGGCCGCCGTCGCTTCTTTCTACGGCTTCGGCCGCCGTAAGCGGCATGTCGCTCGTTATACTGTACGACTGGTCGTGGGTCCTCAGCTGGAGCGA

GATCCCCGATGCCATCGGCCACAACATCACCCTGGCCAACAACGATACCCTGACCGGCATCGATGACTGGCGGCCGAGCAAACATCTGGATCGCAGCCTG
CTAGGGCCTACGGTAGCCGGTGTTGTAGTGGGACCGGTTCTTGCTATGGGACTGGCCGTAGCTACTGACCGCCGGCTCGTTTGTAGACCTAGCGTCGGAC

ACGGCGCACGGCATCGACAAGGTGATAAGCTCGATGGCGGAACAAAAGCCGTGGGAGGCGAAGGCCAATGCC
TGCCGCGTGCCGTAGCTGTTCCACTATTCGAGCTACCGCCTTGTTTTCGGCACCCTCCGCTTCCGGTTACGC
```

A Cell Containing the Hydrolytically Active Exoenzyme

As mentioned above, the present invention relates in one aspect to a cell containing a gene coding for the hydrolytically active exoenzyme as defined herein. The cell may be selected from a wide variety of cells for which a need for containment exists. Thus, the cell to be contained may be a bacterial cell, a protozoan cell, a yeast or fungal cell, or a cell derived from the tissues of multicellular organisms such as plants, animal and fungi.

The gene coding for the hydrolytically active enzyme may be derived from a variety of replicons contained in any organism producing an extracellular enzyme as presently defined. Thus, sources of the gene include bacterial chromosomes, bacterial plasmids, prokaryotic viruses, eucaryotic viruses, eucaryotic plasmids, or eucaryotic chromosomes. The gene may also be constructed synthetically according to standard procedures.

In accordance with the invention, the cell as defined herein may be obtained by methods known per se. These methods include the steps of screening for cells expressing a suitable extracellular hydrolytic enzyme, isolating from such cells the gene encoding the enzyme, removing from the gene the nucleotide sequence coding for the signal peptide and inserting into a cell to be contained, the gene and a nucleotide sequence capable of regulating the expression hereof, growing the cell under conditions allowing the expression of the gene, and testing for the intracellular presence of the enzyme in an enzymatically active form.

The insertion of the gene coding for the hydrolytically active exoenzyme may be in the chromosome of the cell or the gene may be inserted in an extrachromosomal recombinant replicon such as a recombinant plasmid capable of replicating in the cell.

The Regulatory Nucleotide Sequence Regulating the Expression of the Hydrolytically Active Exoenzyme As also mentioned above, the expression of the gene coding for the hydrolytically active enzyme is regulated by a regulatory nucleotide sequence. In the present context the term "regulatory nucleotide sequence" is intended to indicate a nucleotide sequence which directly or indirectly regulates the expression of the gene coding for the hydrolytically active enzyme at the level of transcription or at the level of translation. The regulatory nucleotide sequence may be one, the function of which results in a suppression or inhibition of the activity of the regulatable promoter. Such regulatory nucleotide sequences are herein referred to as "negatively functioning regulatory nucleotide sequences".

One interesting example of such a negatively functioning regulatory nucleotide sequence is a sequence coding for a repressor substance which represses the expression of the gene coding for the hydrolytically active enzyme and which substance may, when a cell containing it is released to a human or an animal body or to the outer environment, undergo a decay whereby the repression of expression of the enzyme-encoding gene is gradually reduced and eventually, when the decay of the repressor is completed, the repression is removed.

In preferred embodiments of the invention, the regulatory nucleotide sequence is contained in the cell in one or more recombinant replicons and it may be contained in the same replicon as that containing the enzyme-encoding gene or in a different recombinant replicon.

One way whereby the expression of the cell function-limiting enzyme in accordance with the invention is regulated is by providing in the cell a gene coding for the hydrolytically active enzyme, which gene is regulated at the level of transcription. The regulation at the level of transcription may be carried out in various ways including a regulation by means of a promoter, regulated by one or more factors. These factors are either ones which by their presence ensure expression of the gene coding for the cell function-limiting enzyme or, alternatively, factors which suppress the expression of the gene so that their absence causes the enzyme to be expressed.

Factors regulating the activity of the promoter as defined above may be selected from a variety of factors. Thus, the expression of the gene encoding the cell function-limiting enzyme may be determined by the environmental conditions or the physiological state of the cells, or by a cyclical or stochastic event. In the present context, the term "cyclical event" is understood to mean a cyclically recurrent event causing changes in certain factors known to be potentially useful in influencing the expression of genes such as temperature conditions, changes in light intensity or hormonal changes. The term "physiological state of the cells" denotes factors such as cell density or the growth phase of cells.

In accordance with the invention, advantageous promoter regulating factors are readily regulatable factors including the presence or absence of a certain chemical substance in the environment or the physical conditions in the environment such as the prevailing temperature or other physical factors (e.g. the intensity of the light in the environment). Thus, it is possible to envisage containment systems as presently claimed, in which the gene coding for the cell function-limiting enzyme is expressed when a certain chemical substance present in a first environment such as the fermentation medium in which the cell is propagated, is not present in a second environment to which the cell is released, or when a factor required for the growth or survival of the cell is no longer present, or the factor is a factor which, when it is exhausted from an environment of the cell, has the desired effect, viz. that the gene is expressed.

The promoter regulating the transcription of the gene coding for the cell function-limiting hydrolytically active enzyme can also become activated in a second environment of the cell by a chemical substance which is not present in a first environment of the cell, but which is present in the second environment in sufficient quantities to activate the promoter. Similarly, the promoter may be a promoter which is activated by a shift in temperature, such as a shift from a higher temperature in a first environment as e.g. a fermentation vessel, to a lower temperature prevailing in an outside second environment, or the intensity of light, in that the promoter is one which is activated in the presence of light of sufficient intensity, but is inactive in the darkness prevailing in a first environment such as a fermentation vessel.

Where cells as defined herein are ones that are to be released to the natural environment in a controlled manner, e.g. to a restricted area of land or to the intestinal tract of a human or an animal, the regulatable promoter is preferably one which is regulated chemically, i.e. by the presence or absence of a certain chemical substance in the environment of the cells as it has been explained above.

However, the regulatable promoter is advantageously a promoter which is activated cyclically, e.g. by changes of the temperature, or most advantageously by a stochastic event. The term "stochastic event" as used herein is intended to denote an event which occurs at random at a certain frequency per cell per generation or at a frequency per unit time which, in accordance with the invention results in a limitation of the function of the cells in which the activation of expression of the cell function-limiting intracellularly active exoenzyme occurs, optionally to an extent which leads to the death of the cells. The stochastic event can be occasioned by periodic inversions of the region carrying the promoter, but is more advantageously induced by the recombinational excision of a recombinationally excisable negatively functioning regulatory nucleotide sequence as defined above.

It should be noted that in order to ensure a general applicability of the present invention, the promoter used to initiate transcription of the gene coding for the cell function-limiting enzyme is preferably a promoter which is capable of causing expression of said gene in a wide range of cells.

In case of regulatable transcription of the hydrolytically active enzyme, the regulatory nucleotide sequence may e.g. be a promoter isolated from bacterial operons involved in the biosynthesis of amino acids or from bacterial genes, the transcription of which is activated late in the stationary growth phase or from bacterial genes involved in the synthesis of cell surface structures such as fimbriae. Examples of suitable promoters are $E.$ $coli$ trp which becomes activated in the absence of tryptophan, the bacteriophage λ $P_R$ and $P_L$ promoters controlled by temperature sensitive regulatory nucleotide sequences, the $Bacillus$ $subtilis$ sporulation gene promoters which are activated during sporulation, and the $E.$ $coli$ and Salmonella fimbriae gene promoters which are activated stochastically.

In case of chemically regulatable promoters, the chemical substance, the presence or absence of which determines the activation of the promoter, is suitably be selected from carbon or nitrogen sources, metabolites, amino acids, nucleosides, purine or pyrimidine bases or metal ions. When the chemical substance is one which, when present, suppresses promoter activity, it should preferably be a substance which rarely occurs in the natural environment in such concentrations that the promoter would not be activated when the cell is released to the natural environment. One example of a suitable promoter in e.g. an $E.$ $coli$ cell is the trp promoter which is repressed in the presence of tryptophan in the environment of the cell, but which is derepressed in the absence of sufficient amounts of tryptophan in the environment. A containment system using the trp promoter or another promoter being regulated in the same manner, therefore advantageously comprises an amount of tryptophan in a first environment, such as a fermentation vessel, to repress the promoter which is derepressed when the cell is released from the first environment to a second environment, e.g. the natural environment which usually contains very low amounts of tryptophan or no tryptophan at all.

Another example of a regulatable promoter, the activation of which is determined by a chemical substance is the lac promoter which is inducible by e.g. isopropyl-β-D-thiogalactopyranoside (IPTG). A particularly useful mode of regulation of the expression of the hydrolytically active exoenzyme according to the invention is described in the below Example 20 where the expression of a snuc* gene is under the control of the $P_m$::lacI gene coding for a repressor for the snuc* gene and which is regulated by the XylS protein the expression of which induced in the presence of 3-methyl benzoate (3-MB). Accordingly, in such a system the cell function-limiting mutated nuclease is not expressed in the presence of 3-MB, but is only expressed in the absence of this xenobiotic compound.

Where cells as defined herein are used in a pesticidally active composition e.g. being administered to a plant, the regulatable promoter is suitably regulated by the presence/absence of a compound secreted by this plant.

As mentioned above, the regulatable promoter is advantageously a promoter, the activity of which is determined by the temperature prevailing in the environment of a cell containing the gene coding for the cell function-limiting enzyme and a the regulatable promoter regulating the expression of the gene. In such a case, the regulation of the promoter is advantageously obtained by the presence in the cell of a temperature sensitive gene coding for a repressor for the promoter. As one typical example, the λ promoters including those mentioned above are regulated by a temperature sensitive λ cI repressor.

Promoters which are activated stochastically by periodic inversions of the promoter region (in the present context, such promoters are also termed as an "invertible promoter" and "inversional switch promoter") and which are useful for the purposes of the present invention include as examples the hin, cin and gin promoters. One particularly useful invertible promoter is the fimA promoter which is one $E.$ $coli$ fimbriae promoter. The activation (inversional switch) of this promoter is regulated by the gene products of the two genes which for the present purposes is termed the "on" and the "off" genes, the on gene product inducing a switch from off (inactive) to on (active), and the off gene product inducing a switch from on to off. In a wild-type $E.coli$ cell where the fimA gene and its associated promoter is present in one copy on the chromosome, the inversional switch occurs with a switching frequency of about one cell/1000 cells/generation. It is, however, possible to regulate the frequency of the inversional switch as required by regulating the dosage of expression of the on and off genes. This is e.g. effected by means of suitable promoters to transcribe into the on and off genes. The frequency of transcription initiation by these promoters will then determine the relative dosage levels of the on and off gene products being formed.

As it has been explained above, the intracellular enzymatic activity of the cell function-limiting enzyme may also be regulated by the presence or absence in the cell of a gene product rendering the cell refractory to said enzymatic activity, e.g. by interacting with the enzyme so that the cell function-limiting effect hereof is not expressed.

Stochastically Induced Regulation of the Gene Coding for the Hydrolytically Active Exoenzyme by Means of Recombinational Excision of Negatively Regulatory Nucleotide Sequences In accordance with the invention, one particularly advantageous method of stochastically regulating the expression of the gene coding for the cell function-limiting exoenzyme is the induction of the gene expression as a result of recombinational excision of an excisable negatively functioning regulatory nucleotide sequence which, while present in the cell, inhibits expression of the gene. In the present context, the term "recombinational excision" refers to the result of a naturally occurring phenomenon of genetic recombination (cross-over) whereby nucleotide sequences in replicons, in a controlled process, pair, brake and rejoin to form recombinant replicons by the sequential action of enzymes acting on the DNA. The frequency of recombinational events in a cell depends i.a. on the degree of homology between paired complementary nucleotide sequences and on the length of the complementary sequences. Thus, it has been shown that about 50 base pairs of homology may be required to obtain recombination in a bacterial cell.

When a negatively regulatory nucleotide sequence is inserted between directly repeated nucleotide sequences of a sufficient length in a recombinationally proficient cell which, in accordance with the invention contains a gene coding for a cell function-limiting enzyme, recombination between the repeats results in the recombinational excision of the negatively regulatory nucleotide sequence allowing the gene to be expressed, whereby the cell function-limiting enzyme may be produced intracellularly in amounts leading to a limitation of the cell function, optionally resulting in the death of the cell.

Accordingly, the phenomenon of recombinational excision as used herein, implies that a DNA subsequence, i.e. the negatively regulatory nucleotide sequence, is excised from a longer DNA sequence through a recombination event. In essence, the longer DNA sequence is cleaved on either side of the subsequence and the fresh ends are joined, leaving out the subsequence. Recombination occurs between sufficient homologous flanking nucleotide subsequences. Thus, with DNA of the general structure W-X-Y-X-Z, X being a repeated sequence and Y being a negatively regulatory nucleotide sequence, this could recombine to form W-X-Z, with the Y subsequence being excised.

As mentioned above, the frequency of the recombination can to some extent be determined by varying the lengths of the repeats and/or the distance between the repeats. Furthermore, the frequency can be varied by using repeat sequences of varying homologies. Thus, nucleotide sequence repeats being 100% homologous and having a size which does not impair recombination will result in a high recombination frequency and hence, in a high frequency of recombinational excision of the negatively regulatory sequence, whereas mismatches within complementary sequences will reduce the recombination frequency depending on the degree of mismatch. As an example, it has been found that 10% divergence between nucleotide sequence repeats may reduce the recombination frequency 40-fold.

Accordingly, the cell containing the gene coding for a hydrolytically active exoenzyme may, in accordance with the invention, be a cell containing a regulatory nucleotide sequence which is a recombinationally excisable negatively functioning regulatory nucleotide sequence being flanked by a first flanking nucleotide sequence and a second flanking nucleotide sequence substantially homologous with the first flanking sequence. As used herein, the term "substantially homologous with" is used to indicate that the degree of homology is sufficient to result in a desired frequency of recombination. In certain embodiments it is, in order to obtain a desirable maximum frequency of recombination, advantageous to use direct repeats, i.e. sequences being 100% homologous, whereas, in other embodiments where a moderate degree of cell function limitation is desirable, it is appropriate to use repeats which are more or less heterologous, but still allowing a desirable lower frequency of recombination to occur. Accordingly, in the present context, the term "sufficiently homologous" may appropriately be used to indicate a degree of homology between two flanking nucleotide sequence repeats which results in a desired frequency of recombinational events in a cell containing the gene coding for the hydrolytically active exoenzyme and a negatively regulatory nucleotide sequence.

As also mentioned above, the frequency of recombination depends on the lengths of the flanking sequences. In useful embodiments of the invention, flanking sequences are used which have a length being in the range of 100–5000 base pairs. In certain preferred embodiments, it is advantageous to use flanking sequences, the length of which is in the range of 200–3000 base pairs. As the flanking sequences can be used any nucleotide repeats of sufficient lengths and homology as it has been defined above. As one useful example of flanking sequences can be mentioned the chloramphenicol resistance gene having a size of about 900 base pairs and which occurs in the plasmid pBR325 (Bolivar, 1978, Gene, 4, 121–136). Another example of a useful nucleotide sequence which, when inserted as repeats results in recombination, is a subsequence of the rrnB gene isolated from the plasmid pKK3535 (Brosius et al., 1981, Plasmid, 6, 112–118) of the rrnB gene isolated from the plasmid pKK3535 (Brosius et al., supra) having a size e.g. in the range of 503 to about 3000 base pairs, such as 598 base pairs.

In one interesting embodiment of the invention, the cell containing a gene whose expression in the cell results in the formation of a hydrolytically active enzyme is a cell wherein said gene is a gene which encodes a first RNA which is a messenger RNA, and which further contains an excisable negatively regulatory nucleotide sequence operably linked to said gene encoding the hydrolytically active gene, which is a gene encoding a second RNA which forms an RNA-RNA duplex with said first messenger RNA and thereby, when it is expressed, inhibits translation of said gene coding for the hydrolytically active enzyme.

In another useful embodiment of the present invention, the recombinationally excisable negatively regulatory nucleotide sequence is a gene encoding a polypeptide repressor of transcription of the gene whose expression results in the intracellular formation of a hydrolytically active enzyme. Such a polypeptide repressor may, e.g. be a lac repressor. As one specific example of a useful lac repressor, the repressor encoded by the LacIq gene can be mentioned.

In a further useful embodiment of the invention, the excisable negatively regulatory nucleotide sequence is a transcription termination sequence, preventing the transcription of the gene whose expression results in the formation intracellularly of a hydrolytically active enzyme. In one specific embodiment of the invention, such a suitable terminator sequence is the rpoCt' transcription terminator isolated from the plasmid pHBA102rpoCt (Squires et al., 1981, Nucleic Acid Res., 9, 6827–6839).

Negatively regulatory nucleotide sequences which in accordance with the invention are suitable, are isolated from nucleotide sequences derived from a virus, or a prokaryotic or eucaryotic cell. Thus, sources of the nucleotide sequence include bacterial chromosomes, bacterial plasmids, prokaryotic viruses, eucaryotic viruses, eucaryotic plasmids, or eucaryotic chromosomes.

In preferred embodiments of the invention, the excisable negatively regulatory nucleotide sequence being operably linked to the gene coding for the hydrolytically active enzyme and the first and second flanking sequences, both as defined above, is provided in the form of a "cassette" which term is used herein to describe a readily insertable nucleotide sequence comprising at least the above-mentioned sequences and optionally the gene coding for the hydrolytically active enzyme, and optionally further nucleotide sequences including as examples a suitable marker such as a gene coding for antibiotic resistance. In the present context, the term "insertable" denotes that the cassette as defined herein is provided with suitable restriction sites at both ends allowing for insertion in a replicon having the same restriction sites. Accordingly, such preferred restriction sites include sites which occur frequently in replicons where insertion is desirable or alternatively, restriction sites which may be easily provided in such replicons.

It will be understood that, in accordance with the invention, a cassette as defined above and which does not comprise the gene coding for hydrolytically active enzyme and operably linked to the negatively regulatory nucleotide sequence, may be inserted in a replicon which is different from the replicon containing said gene. Optionally, the cassette as defined above can be inserted in a first replicon such as e.g. a transposon and subsequently inserted via the transposon into the chromosome to obtain a cell as defined herein.

As it has been explained above, the activation of certain invertible promoters such as the fimA promoter or functional homologues hereof is regulated by the gene products of an on gene and an off gene. It will be understood that this mechanism of promoter regulation provides the possibility of using the off gene or a functional homologue hereof as a negatively regulatory nucleotide sequence which is inserted in the cell as defined herein, as a recombinationally excisable nucleotide sequence in the manner explained in details above. Accordingly, in one embodiment, the present invention provides a cell wherein the gene whose expression results in the formation of a hydrolytically active enzyme is stochastically expressed as a result of recombinational inversion of an invertible promoter sequence of the regulatory nucleotide sequence said promoter being operably linked to the gene.

Stochastically Induced Regulation of the Gene Coding for the Hydrolytically Active Exoenzyme by Means of Site-Specific Recombinational Excision of Negatively Regulatory Nucleotide Sequences In plasmids, inherent mechanisms occur whereby multimer resolution of the plasmid during replication takes place. As exemplified by the broad host range plasmid RP4, this resolution system may comprise (1) a gene coding for a multimer resolving enzyme, a resolvase and (2) a site for the site-specific resolvase-mediated resolution. In plasmid RP4 the gene coding for the resolvase is parA and the site for the resolution is designated mrs. If two mrs sites are placed in direct orientation, a nucleotide sequence inserted between those two sites can, if the parA gene is present in the same host cell, be deleted at a relatively high frequency whereby a site-specific recombination system is provided. In useful embodiments the ParA gene is located in trans.

It has now been found that such a site-specific recombination system provides a useful mechanism for stochastically regulating the expression of a gene such as the gene coding for the hydrolytically active enzyme as defined herein, since the site-specific recombination can be used to obtain recombinational excision of a negatively regulatory nucleotide sequence as defined above.

Accordingly, in one interesting embodiment, the present invention provides a cell as defined herein in which the negatively regulatory nucleotide sequence is a sequence flanked by a first site for a site-specific resolution recombinase and a second site for site-specific resolution, the second site being recognizable by the same or a functionally equivalent multimer resolving enzyme as is the first site, whereby the regulatory sequence is recombinationally excisable in the cell. In a specific embodiment, the gene coding for the multimer resolving enzyme is located in trans relative to the sites for site-specific resolution. In the present context, one useful example of a suitable gene is the parA gene isolated from plasmid RP4.

The Gene Coding for an Intracellularly Active Exoenzyme Having a Cell Function-Limiting Function As it has been mentioned above, the gene coding for the hydrolytically active enzyme can, in accordance with the invention, be derived from several sources including a bacterial replicon. In one preferred embodiment of the invention, the gene is a gene derived from a gram-negative bacterium which may suitably be selected from a species of Enterobacteriaceae, Pseudomadaceae or Vibrioriaceae such as a Serratia species, an Aeromonas species or a Yersinia species. In a specific embodiment, the Serratia species is *Serratia marcescens* and the hydrolytically active enzyme is an enzyme as defined herein encoded by a *Serratia marcescens* gene. In particularly preferred embodiments, the *Serratia marcescens* gene may be one encoding an endonuclease and having the DNA sequence as defined above or a gene encoding a phospholipase and having the DNA sequence as defined above.

In a further useful embodiment, the invention provides a cell as defined above which contains a gene coding for a hydrolytically active exoenzyme which gene is derived from a gram-positive bacterial species including as an example a gene coding for a nuclease without its signal peptide which gene is isolated from a Staphylococcus species such as *Staphylococcus aureus* and e.g. carried on a plasmid. One example of such a gene is one carried by the plasmid pFOG408.

Provision of a Cell According to the Invention in which the Function-Limiting Effect of the Hydrolytically Active Enzyme is Increased by Mutation In certain embodiments, it is advantageous to obtain a higher intracellular enzymatic activity than is obtained by the insertion of the gene coding for the hydrolytically active enzyme and/or the regulatory nucleotide sequence in the form in which this/these sequence(s) are primarily isolated. Such a higher activity may be the result of an increased amount of enzyme being expressed and/or of an increased specific activity of the enzyme, relative to the amount or the specific activity which is obtained by the insertion of the primarily isolated sequences. An increased intracellular activity of the hydrolytically active enzyme may also be the result of an increased intracellular stability of the enzyme. Furthermore, a higher intracellular enzymatic activity can be obtained with a modified enzyme which relative to a parent enzyme which to some extent is transported extracellularly, is retained essentially intracellularly.

Such increased enzymatic activity is conveniently obtained by subjecting the isolated sequences separately or together to a conventional in vitro or in vivo mutagenization treatment e.g. with a chemical mutagen, by means of a site-directed mutagenesis, e.g. by use of a PCR technique, or by a mutagenically active radiation treatment.

Cells containing thus treated nucleotide sequences in which a mutation or mutations resulting in an increased intracellular enzymatic activity have occurred, are selected by growing a culture of the cells under conditions where the gene coding for the hydrolytically active enzyme is expressible, and isolating cells or cell clones which relative to cells or cell clones containing the primarily isolated sequences and grown under the same conditions, show an increased level of cell function limitation as defined above.

Accordingly, the invention provides in one embodiment a cell as defined herein in which at least one of the genes whose expression results in the formation of a hydrolytically active enzyme and the nucleotide sequence regulating said gene, is mutated at one or more sites, whereby the cell function-limiting effect of the enzyme encoded by the gene, when expressed in the cell, is the same or increased relative to the cell function-limiting effect of the enzyme expressed in a cell containing said gene and said nucleotide sequence in non-mutated form. In one interesting embodiment, the cell in which the enzyme activity is increased by the mutation treatment is a cell containing a gene coding for an endonuclease such as e.g. a gene derived from a Serratia species or a mutant nuclease encoded by a mutated Staphylococcus spp gene such as the nucleases encoded by pSNUC24–26 or pSNUC420–26 as described below.

A Cell According to the Invention Comprising a Further Regulatably Expressible Gene which Encodes a Cell Function-Limiting Function As a means of increasing the cell function-limiting effect in a cell as defined herein it may be advantageous to insert into the cell a further regulatably expressible gene which further gene is a gene encoding a cell function-limiting gene product. Accordingly, the present invention provides in one specific embodiment a cell containing a further gene as defined above. Such a further regulatably expressible gene can be regulated by a regulatory nucleotide sequence of the same type as the sequence regulating the gene coding for the hydrolytically active enzyme or the gene is one which is regulated by a regulatory nucleotide sequence of another type, said other type of regulatory sequence optionally being one which is also capable of regulating the expression of the gene coding for cell function-limiting hydrolytically active enzyme.

A suitable gene coding for a further regulatably expressible cell function-limiting gene product is conveniently selected from the above-mentioned genes having cell killing function. In certain preferred embodiments, said further gene is selected from the hok gene of the parB region of plasmid R1, the gef gene and a DNA sequence which is a functional equivalent of either of these genes.

Another suitable example of a suitable further enzymatically active cell function-limiting gene product is an exonucleolytically active enzyme which is expressed intracellularly in the mature form such as the *E. coli* exonuclease III. One advantage of providing in a cell to be contained the simultaneous expression of the staphylococcal nuclease according to the invention and an exonuclease as defined above is that the enzymatic efficiency of the staphylococcal nuclease in the cell is enhanced.

A Cell as Defined Herein which Further Contains a DNA Sequence Not Naturally Related to the Replicon Carrying the Gene Coding for the Hydrolytically Active Enzyme As it has been defined above, the cell according to the present invention may, when occurring as a population comprising a multiplicity of the cell which further comprises a DNA sequence coding for an immunologically active enzyme, a pesticidally active or a pollutant-degrading gene product, respectively, is useful in an immunologically active composition, a pesticidally active or a environmental pollutant-degrading composition, respectively, to be contained in the particular environment where such a composition is released.

Accordingly, in such specific embodiments the cell is a cell which further comprises a DNA sequence not naturally related to the replicon carrying the gene whose expression results in the formation of a hydrolytically active enzyme and/or the replicon carrying the regulatory nucleotide sequence, said DNA sequence being selected from a sequence coding for an immunologically active gene product, a sequence coding for a pesticidally active gene product and a sequence coding for a pollutant degrading gene product.

In the present context, the term "immunologically active gene product" is used to describe an epitope (antigenic determinant) from a pathogenic organism which, when it is administered to the body of a human or an animal is capable of stimulating the formation of antibodies therein. A cell as defined in the present invention which contains one or more genes encoding such a gene product can be utilized in the preparation of useful live vaccines. In the immunization against several pathogens it is considered advantageous to administer live vaccines as compared to killed organisms or antigenic fragments of the pathogen, since the level of immunity conferred by a live vaccine is frequently higher than that conferred by vaccines comprising killed pathogenic organisms or fragments thereof. Most known vaccines comprising viable epitope-containing organisms are either based on recombinant non-pathogenic organisms encoding the epitope or they are based on attenuated pathogenic organisms. The cell advantageously contains a multiplicity of genes each of which codes for a specific immunologically active gene product.

However, up till now the use of live vaccines has been limited since it is often difficult to obtain the right combination of attenuation, viability and adequate immune response. Furthermore, the deliberate release of genetically engineered microorganisms to the body and to the external environment which is a result of the use of viable recombinant organisms as vaccines, is currently not allowed in any country for reasons of public concern as to the possible long-term environmental impact, in particular the risk of permanent establishment of the GEMs in the environment.

The present invention provides an advantageous means of circumventing these problems associated with the use of known GEM-based live vaccines by introducing into a viable epitope-containing cell the regulatably expressible gene coding a cell function-limiting hydrolytically active enzyme as defined above. In particularly interesting embodiments, the invention provides as a useful basis for a viable vaccine, the cell as defined above which contains a gene coding for the hydrolytically active enzyme whose expression is stochastically induced.

In useful embodiments of the invention, the cell which contains the DNA sequence coding for an immunologically active gene product further comprises means for transporting the epitope, when expressed, to the outer surface of the cell, i.e. translocating it across the cell membrane. Preferably such a translocation is obtained by inserting the gene coding for the epitope into a nucleotide sequence coding for an outer cell surface polypeptide structure such as fimbriae which contains the fimbrillin protein, pili, flagellae or certain other surface proteins including as an example the OM protein found in Streptococcus species. By providing the cell with such a hybrid nucleotide sequence being expressible in the cell, the gene product hereof will be a fusion or hybrid protein comprising the epitope and the relevant cell surface structure.

A cell in which is expressed a fusion protein which comprises the epitope fused to a surface structure protein by which the cell can adhere to the mucosal cells of a body to which the cell is administered, is considered to be particularly useful in that the epitope will be brought in close contact with the mucosa and thereby effectively stimulate a protective immune response in the form of the excretion of secretory antibodies of the IgA and IgG classes.

Furthermore, the adhesion of the epitope-carrying cell will ensure that the cell is retained in the human or animal body for a period of time which is sufficient to obtain the desired immune response. It is considered that a satisfactory immunization typically may be obtained if the cell is present in sufficient numbers in a particular body environment such as the intestinal tract for a period in the range of 15–30 days, depending on the nature and the activity of the epitope expressed from the cell.

As it will be understood from the above description of the gene coding for the cell function-limiting hydrolytically active enzyme and the regulatory nucleotide, the present invention provides useful means of providing live vaccines based on recombinant organisms which are immunologically effective and which can be used without the risk of undesired spreading of recombinant genes to the microflora of humans and animals or to the outer environment.

In accordance with the invention, a useful cell for the preparation of a live vaccine is one selected from a bacterial species which inherently contains an outer surface structure as mentioned above. Such species include as examples species of Enterobacteriaceae such as Salmonella and *E. coli* species, Vibrionaceae and Pseudomonadaceae. It will be understood that strains of such species which are particularly useful in the present invention as the basis of a live vaccine as defined above, are non-pathogenic strains or strains having low pathogenicity.

The epitope expressed by a cell as defined above can be an epitope derived from any pathogenic organism or agent against which it is desirable to obtain immunity. Such pathogens include viruses, bacteria and eucaryotic organisms such as fungi, yeast or protozoa.

In commercially important embodiments, the cell according to the invention contains a nucleotide sequence coding for a pesticidally active gene product. In this context, the term "pesticidally active gene product" is used to denote a product which, when expressed in a cell being released to an environment where there is a need to reduce or eliminate the presence of pests including insect pests, vermins such as rodents or birds, has a pesticidal effect. Until recently, such pests were primarily controlled by the administration to the infestated environment of toxic chemical pesticides, but recently various naturally occurring pesticidally active organisms including viruses, bacteria and fungi have been used as biological pest control products.

Prominent examples of such pesticidally active organisms include biotypes or strains of the species *Bacillus thuringiensis* which produce crystalline proteins being toxic to insects, in particular to caterpillars, and several viruses being pathogenic for insects in the larval stage or in the adult stage. However, the pesticidal effect of such organisms is frequently less satisfactory and there is a strong need in farming, forestry and horticulture to provide improved pesticidally active organisms. One approach to solving this problem is to construct genetically engineered organisms having an increased toxic effect or a better survival rate in the environment.

When such improved organisms are developed, their use in the environment will, as a consequence of current public concern of the potential risks involved in deliberate release of such toxic or pathogenic GEMs, only be approved by official environmental agencies if it can be demonstrated that the release does not lead to an undesired propagation or to an extended survival of such organisms in the environment to which they are applied.

The present invention clearly provides the means of limiting the survival in the environment of genetically engineered pesticidally active organisms. As it has been explained above, the rate of expression of the cell function-limiting hydrolytically active enzyme can be regulated stochastically and thus the survival rate of pesticidally active cells may conveniently be adapted to any specific need. Also, the cell function-limiting effect may, in accordance with the present invention be adjusted by selecting a hydrolytically active enzyme which has an appropriate cell function-limiting effect.

In another useful embodiment, the invention provides a cell in which the DNA sequence not naturally related to the gene coding for the hydrolytically active enzyme, is a sequence coding for a pollutant-degrading gene product. It is known that several xenobiotic compounds polluting the outer environment including soil and water can be degraded by micro-organisms having an inherent capability of degrading these compounds. Obviously, the technology of genetic engineering provides means of providing improved organisms having an increased pollutant-degrading capacity or having the capacity to degrade a broad range of compounds, in particular hydrocarbons.

However, the public concern as mentioned above are also relevant in this context and accordingly, the present invention provides useful means of providing improved pollutant-degrading cells, the survival of which can be controlled by regulating the expression of the cell function-limiting hydrolytically active enzyme as it is defined above. In particularly preferred embodiments, the cell contains a gene coding for a pollutant-degrading gene product, the expression of which is induced by the presence of a pollutant degradable by the cell.

Cell as Defined Herein which is a Transformed Cell

In a further specific embodiment of the invention, the cell according to the invention and as defined above, is a cell which is transformed with a recombinant replicon or recombinant replicons containing a gene whose expression results in the formation of the cell function-limiting enzyme, the expression of said gene being regulated by a regulatory nucleotide sequence which is contained in the recombinant replicon containing the gene or in another recombinant replicon present in the transformed cell.

Replicon Containing a Gene Coding for an Intracellularly Hydrolytically Active Cell Function-Limiting Enzyme and Optionally A Regulatory Nucleotide Sequence As mentioned above, the present invention pertains in a further aspect to a recombinant replicon containing the regulatably expressible gene encoding an intracellularly active hydrolytic enzyme as defined above, having, when it is expressed in a cell, a function-limiting effect thereon, said gene being regulated by a regulatory nucleotide sequence as also defined above and which sequence is operably linked to the expressible gene. In accordance with the invention, the regulatory nucleotide sequence can be a sequence contained in the replicon or in another replicon present in the cell containing the expressible gene.

In accordance with the invention, the replicon can also be a replicon wherein the gene coding for the hydrolytically active enzyme and/or the nucleotide sequence regulating the expression of said gene, when such a sequence is present in the replicon, is mutated at one or more sites, so that the cell function-limiting effect of the enzyme encoded by the gene, when it is expressed in a cell containing the replicon, is the same or increased relative to the cell function-limiting effect of the enzyme as expressed in a cell containing a replicon as defined herein not having been mutated.

In one embodiment, the replicon comprises a further regulatably expressible gene which encodes a cell function-limiting function, the expression of which is regulated by a regulatory nucleotide sequence of the same type as the sequence regulating the gene coding for the cell function-limiting hydrolytically active enzyme. In other embodiments, the nucleotide sequence regulating the expression of the cell function-limiting function is of a different type which however, may also be capable of regulating the expression of the gene encoding the cell function-limiting hydrolytically active enzyme.

In useful embodiments, said further regulatably expressible gene is the hok gene from the parB region of plasmid R1 or a DNA sequence which is functionally homologous to the hok gene or the *E. coli* chromosomal gef gene or an exonucleolytically active enzyme such as an *E. coli* exonuclease.

In other useful embodiments, the replicon further comprises a DNA sequence as defined above which is not naturally related to the replicon and which encodes a gene product selected from an immunologically active gene product, a pesticidally active gene product and a pollutant-degrading gene product.

Population of Cells Containing a Gene Coding for an Intracellularly Hydrolytically Active Exoenzyme Having Cell Function-Limiting Effect As mentioned above, the present invention pertains in a further aspect to a population of cells consisting of a multiplicity of cells as they have been defined above. Preferably, the cell population comprises cells having been transformed with a recombinant replicon as defined herein which are capable of replicating in the cells. Since the cell population in interesting uses is released to the outer environment, the cells are in advantageous embodiments bacterial cells which are selected from species whose natural habitat is a habitat selected from soil, surface water and plants, such as gram-negative bacterial species.

In this context, it is interesting to note that the survival of a population of cells as presently defined in which the expression of the gene coding for the cell function-limiting enzyme is regulatable by a repressor substance which is present in the cells, but in different amounts depending on the physiological state of the cells, when such a population is applied to a human or an animal body, or to the outer environment, is regulated as a result of a decay of the repressor substance to an extent whereby the repressor substance is converted to a non-functional form. Provided the amount of the repressor substance in individual cells of a population being released, is different, it is assumed that this decay will result in a gradually increasing loss of viability of the cells of the population.

Method of Limiting the Survival of a Cell Population

As it has also been mentioned above, the present invention provides in one aspect a method of limiting the survival of a cell population in a first or a second environment wherein the regulatory nucleotide sequence is regulatable by an environmental factor as defined herein. The method is in preferred embodiments related to a cell population as defined above.

In specific embodiments of this method, the survival of the cell population is limited in a first environment in which the gene coding for the cell function-limiting hydrolytically active enzyme is expressed whereby the cell population is contained in the first environment. In the present context, a first environment is typically the place of primary propagation of the cell such as a fermentation vessel.

In another specific embodiment of the method, the survival of the cell population is limited in a second environment which may is typically a first environment changing to a chemically different second environment, e.g. by the depletion of certain chemicals or the addition of such chemicals, or to a physically different second environment which change e.g. takes place by a shift in temperature or by a change of light intensity.

A cell population as defined herein may also be a cell population wherein the expression of the gene coding for the function-limiting enzyme is regulatable by a repressor substance which can undergo a decay or a degradation when said cells are released to a human or animal body or the outer environment to an extent whereby the repressor substance is converted to a non-functional form, said repressor substance being present in the cells of the population in different amounts whereby, as a result of said decay, the function of the cells of the population will gradually be limited.

Accordingly, the present invention provides in one useful embodiment a method of limiting the survival of a cell population by providing the cells with a gene coding for the hydrolytically active enzyme which is operably linked to a regulatory nucleotide sequence encoding a repressor substance which can undergo a decay when said cells are released to a human or animal body or the outer environment, to an extent whereby the repressor substance is converted to a non-functional form, said repressor substance being present in the cells of the population in different amounts whereby as a result of said decay the function of the cells of the population will be gradually be limited.

A Method of Containing an Extrachromosomal Recombinant Replicon

As defined above, the invention relates in one aspect to a method of containing an extrachromosomal recombinant replicon to a first kind of cells where the replicon is naturally transferable to a second kind of cells, in which method the recombinant replicon is preferably a recombinant replicon as defined herein. In one preferred embodiment, this replicon is one not containing a regulatory nucleotide sequence and advantageously, such a replicon contains a gene coding for a hydrolytically active enzyme which is an endonuclease capable of hydrolysing diesterphosphate bonds in nucleic acids in the first kind of cells containing the replicon to be contained.

Method of Stochastically Limiting the Function of Cells in a Cell Population

In a particularly interesting aspect, the invention pertains, as it has been mentioned above, to a method of stochastically limiting the survival of a cell population such as a cell population as defined above, said method comprising the transformation of the cells with a recombinant replicon as also defined herein. In one useful embodiment, the method comprises a method wherein the expression of the cell function-limiting hydrolytically active enzyme is induced as a result of a site-specific recombinational excision of an excisable negatively functioning regulatory nucleotide sequence which, while present in the cells, inhibits expression of said gene, the negatively functioning regulatory nucleotide sequence being contained in the recombinant replicon or in another recombinant replicon present in the cells.

In another useful embodiment of this method, the survival of the cell population transformed with a recombinant replicon as presently defined, is being limited as a result of the above-defined recombinational inversion of an invertible promoter sequence of the negatively functioning regulatory sequence. In accordance with the invention, the negatively functioning regulatory sequence can be one contained in the recombinant replicon or it is one present on another replicon present in the cells. As one suitable example, the promoter sequence is a sequence carrying the fimA promoter or a functional homologue thereof.

An Immunologically Active Composition

The immunologically active composition as defined above can in addition to the viable function-limited cell population comprise pharmaceutically acceptable carriers and additives. Such acceptable carriers include any vehicle which is used conventionally in vaccine production such as e.g. saline. In the present context, suitable additives include immune response-enhancing substances including as examples Freund's incomplete and complete adjuvant and other non-specific immunostimulating substances.

It may be preferred to provide the composition in the form of lyophilized compositions, optionally in combination with a suitable aqueous vehicle such as saline. The immunologically active composition as presently defined may contain different types of cells, each of which encodes a specific epitope. Alternative, the immunologically active composition according to the invention contains a population of cells containing a multiplicity of genes coding for an immunologically active gene product, each gene coding for a different gene product.

The immunologically active compositions provided herein are useful vaccines for the immunization of both humans and animals.

In preferred embodiments, the immunologically active composition contains cells containing a sequence encoding for an immunologically active gene product which is a sequence coding for a fusion protein comprising said gene product and a polypeptide, the presence of which results in the transportation of the fusion protein to the outer surface of the cells. As suitable examples, the composition contains cells wherein the polypeptide is one selected from a polypeptide selected from a bacterial fimbrillin protein, a bacterial pilus, a bacterial flagellum and a bacterial OM surface protein.

Nucleotide sequences coding for such a polypeptide are conveniently isolated from a bacterium selected from Enterobacteriaceae, Vibrionaceae and Pseudomonadaceae. A Pesticidally Active Composition In specific useful embodiments, a pesticidally active composition as defined herein contains a further DNA sequence encode a gene product which is toxic for insects or their progeny. In one interesting embodiment, the further DNA sequence is one derived from a strain of Bacillus thuringiensis which codes for an insecticidal protein.

As it has been explained above, cells as defined herein may code for a variety of pesticidally active gene products including the insecticidal protein mentioned above. Accordingly, this composition is useful in controlling a wide range of pests and vermins. Cells which are useful in the pesticidally active composition suitably contain a gene coding for the active gene product which are isolated from naturally occurring organisms producing or having a pesticidal activity.

The pesticidally active gene products coded for by the cells of the composition are gene products which have a toxic effect on a pest or vermin, or the gene products are pest pathogenic viruses which are expressed in the cells of the composition. The cells which in accordance with the present invention are used in this composition include cells in which the gene coding for a desired pesticidally active gene product can be expressed. Such cells include bacterial and fungal cells and plant and animal cells, optionally grown as cell cultures.

The pesticidally active composition may further comprise a suitable carrier. In this context, the term "suitable carrier" is used to indicate that the carrier comprises compounds which enhance the spreading of the composition in the pest infested environment such as bulking agents which do not limit the survival of the cells in the composition, and compounds which may ensure the maintenance of the viability of the cells during production and storage of the composition and optionally also after application to the environment. As an example, a typical carrier contains a compound which protect against the ultraviolet light which is detrimental to many organisms.

An Environmental Pollutant-Degrading Composition

The environmental pollutant-degrading composition as defined herein may preferably contain cells wherein the gene coding for the cell function-limiting hydrolytically active enzyme is only expressed when the pollutant degradable by the pollutant-degrading gene product is substantially degraded. As an example, such a composition may contain cells in which the expression of the hydrolytically active enzyme is repressed in the presence of the degradable pollutant such as is the case in the above system where the expression is suppressed in the presence of the xenobiotic compound 3-methyl benzoate.

DESCRIPTION OF THE DRAWINGS

The invention is further explained below with reference to the drawing in which

FIG. 9 shows a schematic representation of the plasmids pCK80, pCK81, pCK82 and pCK95.

FIG. 30 shows the nucleotide sequence (SEQ ID NO:13) of the Staphylococcus aureus (Foggi) nuclease including the signal peptide encoding sequence, and the amino acid sequence (SEQ ID NO:14) of the signal peptide and the mature enzyme.

EXAMPLE 1

Construction of a Gene for a Cytoplasmic Nuclease

The gene encoding the extracellular nuclease from *Serratia marcescens* has been cloned and sequenced. It has been shown that this nuclease also, when expressed in *E. coli*, is partly extracellular, partly periplasmic. The sequence of the gene indicated that the transport of the protein is mediated by a signal peptide recognised in the N-terminal end of the protein, and determination of the N-terminal amino acid sequence from the mature excreted nuclease verified that a signal peptide was removed from the proprotein during its transport. Hence, the active enzyme normally found after expression and excretion in either *S. marcescens* or *E. coli* is a processed form of the protein.

In order to assess the biological activity of the *S.marcescens* nuclease intracellularly, a plasmid carrying an inducible promoter fused to the nuclease coding sequence representing the mature, processed part of the protein, was constructed. This construction was facilitated by the presence of an EagI site at the border between the signal sequence and the sequence coding for the mature nuclease. In addition, an EagI site was present just downstream of the (C-terminal nuclease coding sequence. Thus, an EagI fragment encoding the entire mature part of the nuclease could be isolated after restriction of a plasmid like pNU121-nuc+ disclosed in WO 86/06743, encoding the total nuclease precursor protein.

The inducible promoter system chosen for the following construction was the plasmid, pUHE24-2, which carries a synthetic lac operator-promoter that is highly repressed in the absence of inducer, and extremely efficient in transcription after induction with IPTG. The plasmid also carries an efficient ribosome binding site coupled to a translational start codon enclosed in a multiple cloning site. There is no EagI site present in pUHE24-2.

Figure 1:
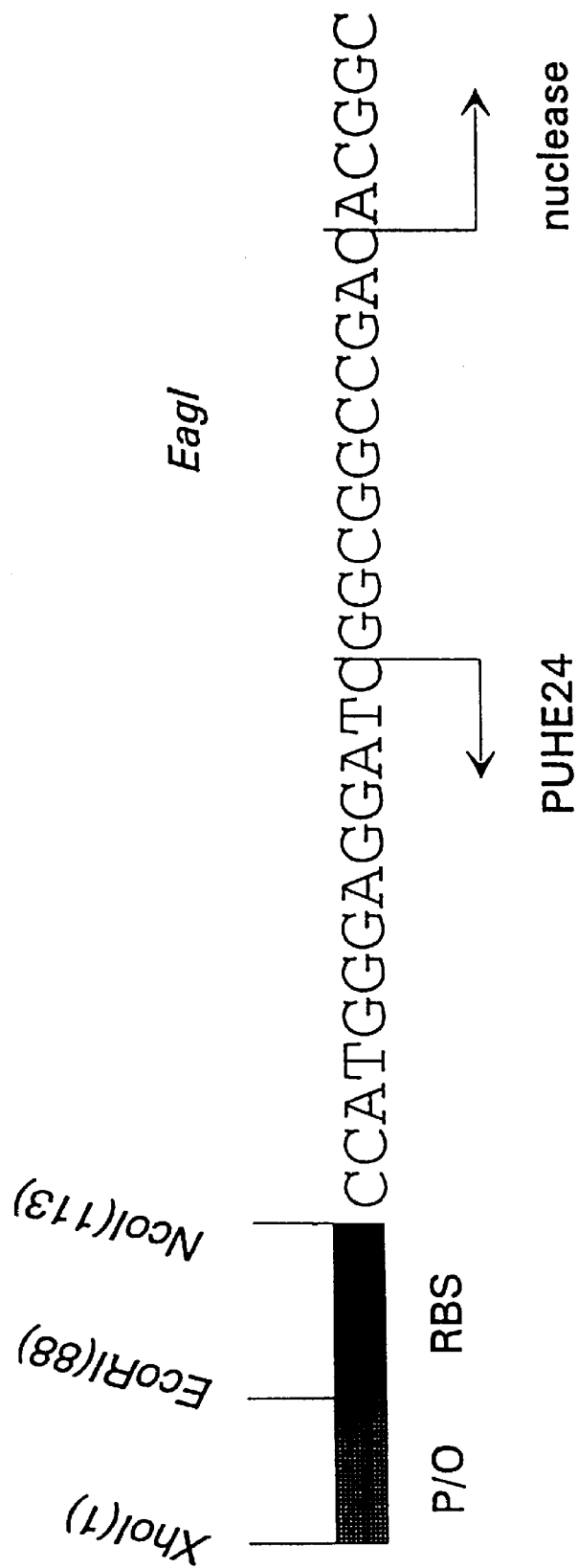
FIG. 1 shows a segment (SEQ ID NO:7) of plasmid pSM1088 showing an oligonucleotide linker comprising an EagI site inserted between the BamHI site and the SalI site of pUHE24-2.
Figure 2:
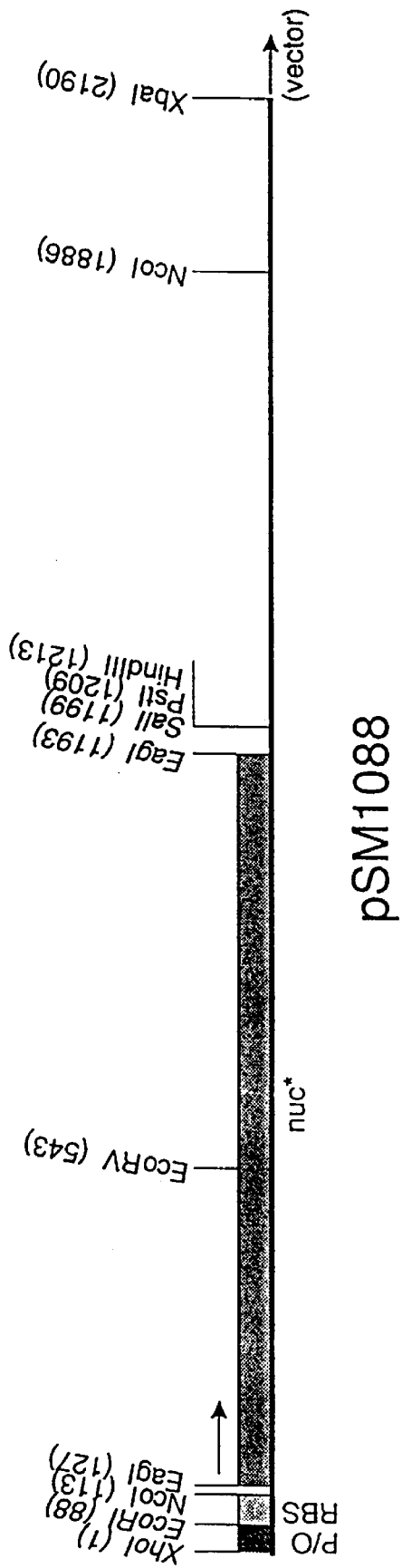
FIG. 2 shows a map of plasmid pSM1088.

For the insertion of the EagI fragment carrying the nuclease gene minus its signal sequence, an oligonucleotide linker comprising an EagI site was inserted between the BamHI site and the SalI site of pUHE24-2, cf. FIG. 1. Subsequently, the purified EagI fragment encoding the nuclease mature protein was ligated to the new pUHE24-2 derivative restricted with EagI, and transformants of strain JM105 comprising the lacI$^q$ gene were tested for viability on plates containing IPTG. Several clones were identified which exhibited poor growth on IPTG plates compared to control colonies harbouring no nuclease gene. Mapping the plasmid isolated from such clones showed that the nuclease gene had indeed been inserted in the correct orientation, and as is shown in FIG. 2 such an insertion leads to an in-frame fusion between the start codon of the expression vector and the nuclease sequence of the EagI fragment. In the following the nuclease gene with the indicated modifications will be referred to as the nuc* gene, and the resulting plasmid described here was designated pSM1088.

The plasmid pSM1088 contained in *E. coli*K12 JM105 was deposited on 5 Jul., 1991 with Deutsche Sammlung von Mikroorganismen und Zellkulturen GmbH (German Collection of Microorganisms and Cell Cultures), Mascheroder Weg 1B, 38124 Braunschweig, Germany.

EXAMPLE 2

Insertion of the nuc* Gene in Tn5

In order to obtain easy ways of transferring the constructed nuc* gene to the chromosomes of other bacteria, the gene with its expression promoter (from pUHE24-2) was inserted together with a gene encoding the lac repressor in Tn5 on a mobilizable plasmid.

Figure 3:
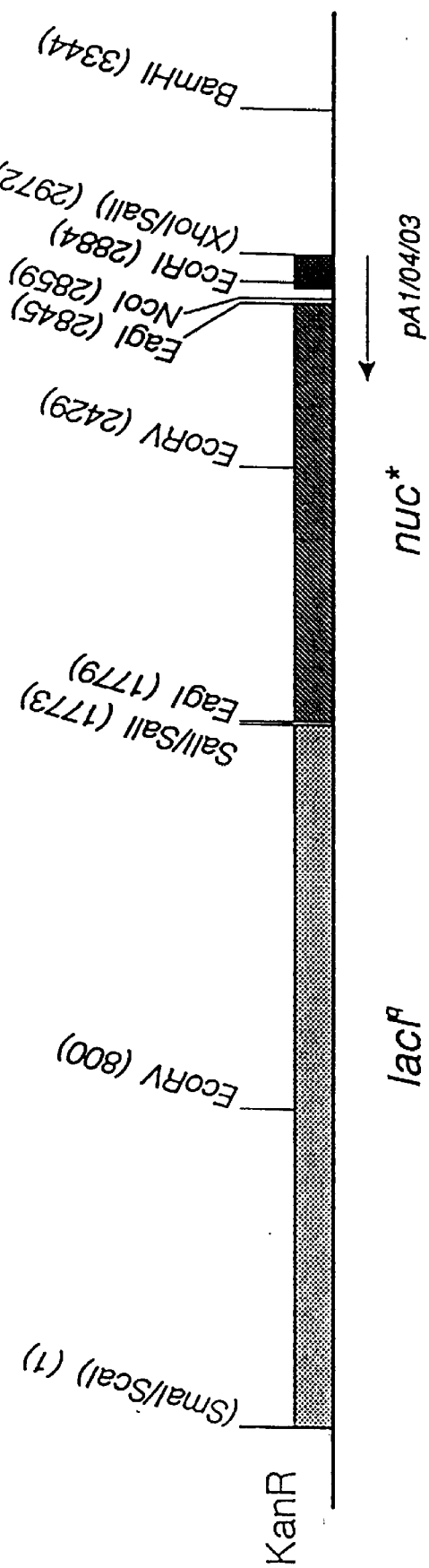
FIG. 3 shows a map of plasmid pSM1093.

The first vector used was the pBR325 derivative, pSUP202 (Simon et al., 1983, Biotechnology, 1, 784–790) which has an insertion of the mob site from plasmid RP4 upstream of the tet gene. From strains of *E. coli* such as strain S17.1 which has RP4 integrated in the chromosome, pSUP202 may be mobilized to a broad spectrum of bacteria. The following modifications of plasmid pSUP202 were carried out:

i) The plasmid was restricted with EcoRI, the single strand ends filled in with the Klenow fragment of DNA polymerase, the DNA ligated and finally transformed to MT102. Selection was for resistance to ampicillin, and colonies were screened for loss of chloramphenicol resistance (the EcoRI site is in the cat gene). The resulting plasmid was designated pSM865.

ii) Plasmid pSM865 was restricted with the enzymes BamHI and SalI, the single stranded ends filled in with Klenow enzyme, the DNA ligated and finally transformed to *E. coli*K12 MC1000 (Simon et al., supra). Selection was for resistance to ampicillin, and colonies were screened for loss of tetracycline resistance (the chosen restriction sites are located in the tet gene). The resulting plasmid was designated pSM878.

iii) The transposon Tn5 was inserted in pSM878 through infection of MC1000 (pSM878) with lambda phage carrying Tn5. After selection of kanamycin resistant colonies, they were pooled, plasmid DNA was prepared and subsequently transformed into a plasmid-free MC1000 strain, again selecting for kanamycin resistance. The transformants were screened for loss of ampicillin resistance, thus identifying inserts of the transposon in the bla gene. Verification of this was done by standard mapping of the resulting plasmid which was designated pSM890.

iv) The lacI$^q$ gene was inserted in Tn5 in pSM890. Plasmid pTTQ19 was restricted with Eco0109, and a SalI fragment was linker-inserted. From the resulting plasmid, the lacI$^q$ gene was isolated as a SalI-ScaI fragment, which was ligated to pSM890 restricted with the enzymes SalI and SmaI. The resulting plasmid harbours the lacI$^q$ gene in Tn5, and it was designated pSM1014.

v) Plasmid pSM1088 was restricted with the enzymes XhoI and SalI and plasmid pSM1014 was restricted with SalI. The two restricted DNAs were mixed, ligated and transformed to MC1000 with selection for kanamycin resistance. Colonies were screened for reduced growth on plates containing IPTG, and resulting plasmids were analyzed and mapped. Such a plasmid with insertions within Tn5 of the nuc* gene combined with the synthetic lac promoter from pUHE24-2 and the lacI$^q$ gene, was designated pSM1093. The map of the plasmid is shown in FIG. 3.

EXAMPLE 3

Immunological Assay for Intracellular Nuclease

To a culture of MC1000 (pSM1093) growing exponentially in LB medium was added 1 mM IPTG at an $OD_{450}$ of 0.2. After 30 minutes of continued growth of the culture, chloramphenicol was added at a concentration of 100 μg/ml, and incubation was continued for another 60 min. Samples of 5 ml were taken before addition of IPTG (uninduced control) 30 min after IPTG addition, and at different points of time after the addition of chloramphenicol. The addition of chloramphenicol allowed an assessment of the stability of the nuclease in the cytoplasm of the cells. The cells were collected from the 5 ml samples by centrifugation and resuspended in 0.5 ml TE buffer. These 10 fold concentrated cell samples were sonicated until clarified, and debris spun out. The amounts of nuclease present in the cell extracts were determined by the ELISA method essentially as described in Example 14 below, using preadsorbed polyclonal antibodies raised against the purified extracellular nuclease in rabbits.

The data in Table 1, which represent the ratio between $OD_{492}$ ELISA measurements and $OD_{260}$ measurement data for a standard nuclease are typical for such an experiment, and they show that nuclease protein encoded by the nuc* gene of pSM1093 was expressed in significant amounts as a consequence of induction. However, the protein was fairly unstable, and about 60 minutes after arrest of protein synthesis (achieved by the addition of chloramphenicol) there was no detectable nuclease protein left in the cells.

TABLE 1

The inhibition of growth of *E. coli* strains containing pSM1093 after induction with IPTG and arrest of protein synthesis by addition of chloramphenicol

| Minutes | MC1000 | SM825 | SM1067 |
|---|---|---|---|
| 0 | 1.5 | 1.3 | 1.1 |
| 30 | 4.1 | 3.6 | 2.5 |
| 60 | 0.88 | 3.9 | 1.2 |
| 90 | 0.85 | 2.2 | 1.2 |

MC1000: *E. coli*, SM825: *Enterobacter cloacae*, SM1067: *Pseudomonas fluorescens*.

EXAMPLE 4

Activity Assay for Intracellular Nuclease

The demonstration of immunologically reactive nuclease as described in Example 3 only showed that the protein was expressed; whether this protein had maintained its enzymatic activity intracellularly remained to be demonstrated.

Induction of nuclease synthesis in a culture of cells of MC1000 (pSM1093) was accomplished by the addition of 1 mM IPTG as described above, and after 30 minutes of incubation time the experiment was terminated. Samples were taken before and after the addition of IPTG and total DNA was prepared from the collected cells using a method employing high concentrations of EDTA in order to prevent or greatly reduce nuclease mediated hydrolysis of the DNA after lysis of the cells. As a control of such post-lysis nucleolytic degradation of the DNA an aliquot of previously purified plasmid DNA was added to one of the DNA preparations before the beginning of the lysis procedure. The presence of circular plasmid DNA after preparation of total DNA was taken as a strong indication that no degradation of DNA took place after harvest of the cells.

Figure 4:
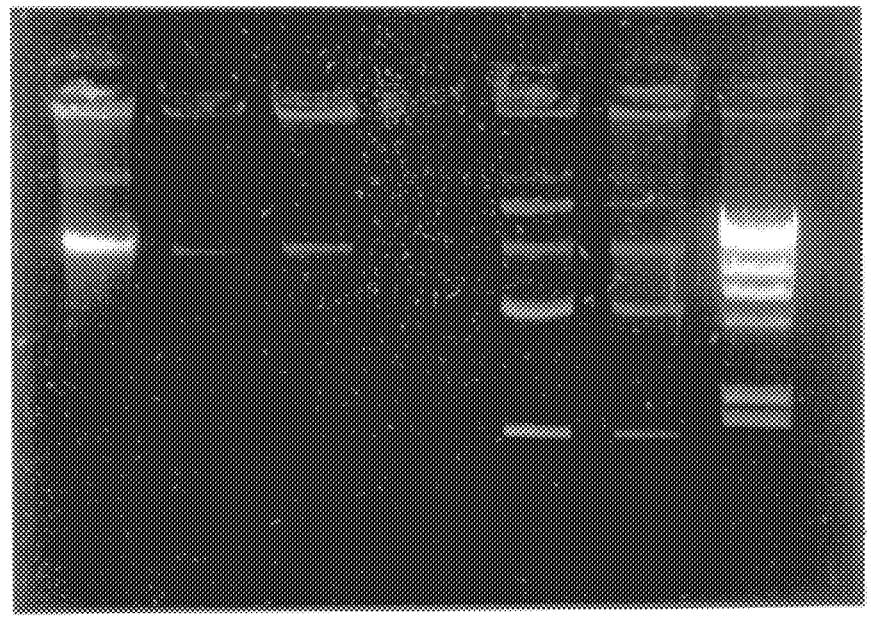
FIG. 4 shows the action of mutated nuclease (mut1) in E. coli S17.1 containing pSM1093-1:1.5 ml culture was harvested and subjected to total DNA preparation. Lane 1, sample taken prior to IPTG addition; lanes 2–4, 30, 120 and 270 minutes after addition of IPTG; lanes 5–6, 30 and 60 minutes after IPTG addition with samples to which were added 0.5 µg of pUC18 DNA prior to DNA preparation; lane 7, lambda DNA digested with HindIII.

The results of such an experiment are shown in FIG. 4. In the sample taken before induction of the nuc* gene the DNA appears as homogeneous undigested bands. In contrast, the DNA prepared from the sample taken after IPTG induction displayed a very heterogeneous appearance (smear) showing a high degree of degradation, and since the plasmid DNA added to such an induced sample retained its homogeneity (no degradation), the digestion of DNA after induction of the nuc* gene must have taken place inside the cells, intracellularly. The expressed protein thus had enzymatic activity.

EXAMPLE 5

Transfer of the nuc* System to Other Bacterial Species

In plasmid pSM1093 the IPTG inducible nuc* gene was placed within the Tn5 transposon on a mobilizable pBR322 derivative plasmid. Therefore, it should be possible to introduce the transposon comprising the nuc* gene in other bacteria by conjugational mating using, *E. coli* as the donor strain. In bacteria allowing the pBR322 plasmid to replicate (Enterobacteria) the transconjugants will carry the transposon on the donor plasmid just as in *E. coli*; in other bacteria (e.g. Pseudomonads) pBR322 plasmids do not replicate, and therefore the only possibility of obtaining transposon mediated antibiotic resistance in these species is transposition to the chromosome or to resident plasmids in the recipient organism.

Conjugal matings were performed by mixing suspended donor cells and recipient cells on LB plates without antibiotics followed by overnight incubation at 30° C. From the colony of mixed cells, aliquots were streaked onto selective plates (selection for kanamycin resistance of the transposon and for the antibiotic resistance marker of the recipient organism, usually rifampicin). Colonies appearing after 1–3 days incubation were restreaked on selective plates and tested for specific recipient characteristics to ensure that transfer had actually taken place.

The resulting transconjugant strains were finally tested for viability on plates containing IPTG. Induction of the nuc* gene in these various bacteria resulted in growth inhibition in several of these, but a few bacteria were apparently resistant to induction. One species, *Enterobacter cloacae*, showed higher sensitivity than *E. coli*.

In order to investigate the cause of the observed differences of sensitivity to the induction in different bacteria, measurements of the induction levels of nuclease protein were performed as ELISA assays as described in Example 3. The results summarized in Table 1 above showed that there was an excellent correlation between the level of induced nuclease protein and the degree of growth inhibition for each bacterial species. It should also be noted that in most of the bacteria the nuclease is as unstable as in *E. coli*; however, in *Enterobacter cloacae* the nuclease is more stable, and therefore higher levels of the enzyme are obtainable intracellularly in agreement with the increased growth inhibition observed in this organism. These results showed that growth inhibition after induction of the nuc* gene varied with the intracellular concentration of the nuclease. When this concentration exceeds a certain level, all bacterial species seem to be equally sensitive to the presence of the enzyme, which again indicates that DNA damages occurring with rates below a threshold value are repaired with equal efficiency in all tested bacteria.

EXAMPLE 6

Optimization of the nuc* Activity

From the characterization of the nuc* expression system as described for plasmid pSM1093 it is apparent that more efficient killing systems may be derived by mutation of the plasmid. In principle, higher nuclease activities in the cells can be obtained either by increasing the protein concentration after induction or by increasing the specific activity of the enzyme. Increased protein concentrations may be a consequence of increased gene dosage, increased gene expression levels or increased stability of the protein; increased specific activity requires mutation(s) in the structural gene for the nuclease.

A mutant screening programme was designed with the purpose of isolating any type of mutation causing increased growth inhibition after induction of the nuc* gene. The basis for the screening was the observation that $E.$ $coli$ cells harbouring pSM1093 are able to form small colonies on IPTG containing plates due to residual growth after induction. Therefore, mutants with increased intracellular nuclease activity would be expected to exhibit more severe growth inhibition on such plates.

Due to the significance of the possibility of transfer of the nuc* system to other bacteria, it was of importance to ensure that mutations leading to optimization were located in the plasmid and not in the chromosomal genes of $E.$ $coli$ (e.g. repair genes or genes encoding proteases responsible for the instability of the nuclease). Therefore, mutagenization was performed directly on purified plasmid pSM1093 DNA using the hydroxyl amine method according to Humphreys et al., 1976, Mol. Gen. Genet., 145, 101. This method comprises the initial preparation of a reaction mixture containing 20 $\mu$l of pure isolated DNA (3 $\mu$g), 100 $\mu$l of sodium phosphate buffer (0.1M, pH 6.0) containing 1 nM of EDTA and 80 $\mu$l of $NH_2OH/HCl$ (1M, pH adjusted to 6.0 with NaOH) containing 1 mM of EDTA. This mixture was incubated at 70° C. for 45 minutes followed by dialysing against DNA dialysis buffer at 2° C. overnight.

The thus treated DNA was subsequently transformed to a non-mutagenized $E.$ $coli$ strain (MC1000). After colonies had appeared on the selective plates (LB +kanamycin) they were replica plated onto plates containing also IPTG for induction of the nuc* gene. After 5–6 hours of incubation at 37° C. the replicas were inspected for growth, and colonies showing no or very poor growth on the IPTG containing plates were restreaked from the master plate (without IPTG) on selective plates and on selective plates containing IPTG and compared with similar streakings of the wild-type pSM1093 strain. From one cycle of mutagenesis 7 clones were isolated which all showed increased growth inhibition of $E.$ $coli$ on plates containing IPTG.

A series of tests was performed in order to characterize the mutated plasmids and possibly reveal the nature of the mutation(s). Using methods and assays already described in the previous examples, the isolated mutants were tested for expression levels of the nuclease protein (ELISA), for stability of the enzyme (ELISA and nuclease activity, spot tests), and for the levels of intracellular nuclease activity (spot tests). In addition, plasmid DNA from the isolated mutant clones was purified and relative amounts of these in the cells and restriction enzyme profiles were determined from inspection of agarose gels. All mutants showed increased amounts of protein and increased nuclease activity, and the correlation of the two parameters indicated that increased expression of the enzyme occurred in all cases. No mutation has caused increased stability of the protein which could be detected with the employed methods. Also, there was no indication of increased plasmid copy number of any of the mutants.

Thus, a preliminary analysis of the mutants pointed at higher expression levels after induction as the most likely cause of increased growth inhibition. One mutant, pSM1093-1, which showed the highest level of growth inhibition and the highest level of intracellular nuclease after induction, was found to have an extra EcoRV restriction site relative to pSM1093. The position of this site coincides with the location of the $lacI^q$ gene, indicating that a mutated repressor responds more optimally to IPTG induction leading to higher post-induction rates of nuc* transcription. Two mutants were selected for further characterization, both of which represent the clones with the highest levels of nuclease activity.

EXAMPLE 7

Comparison of the Properties of pSM1093 and Two Mutant Plasmids

The induced levels of nuclease protein (after 30 min induction) as measured by ELISA essentially as described in Example 14 below, are shown in Table 3. The values indicated represent the ratio between $OD_{492}$ ELISA measurements and $OD_{260}$ measurement data for a standard muclease. The inducing agent, IPTG was added at 0 minutes and chloramphenicol was added after 30 minutes. The results clearly show that pSM1093 (wild-type) produces less enzyme than pSM1093-1. Although the initial rate of degradation of the nuclease from pSM1093-1 seemed very high, the enzymes from the different strains are degraded with the same kinetics after addition of chloramphenicol to the cells.

TABLE 3

Level of nuclease protein after induction with IPTG and addition of chloramphenicol encoded by mutant plasmid pSM1093-1 in MC1000 as compared to the parent plasmid

| Minutes | pSM1093 | pSM1093-1 |
|---------|---------|-----------|
| 30 | 54.7 | 119.2 |
| 60 | 31.6 | 35.8 |

The efficiency of growth inhibition and cell killing of the induced nuclease from pSM1093-1 was studied in growth experiments. The results are shown in table 4.

TABLE 4

The effect of growth on $E.$ $coli$ S17.1 of intracellular nuclease encoded by pSM1093-1

| Hours after addition of | Colony forming units per ml on LB with | |
|---|---|---|
| 2 mM IPTG | Kanamycin | Kanamycin + IPTG |
| 0 | $1.2 \times 10^7$ | $1.3 \times 10^3$ |
| 1.5 | $2.7 \times 10^4$ | — |

TABLE 4-continued

The effect of growth on E. coli S17.1 of intracellular nuclease encoded by pSM1093-1

| Hours after addition of | Colony forming units per ml on LB with | |
|---|---|---|
| 2 mM IPTG | Kanamycin | Kanamycin + IPTG |
| 3.0 | $3.0 \times 10^4$ | $2.1 \times 10^4$ |
| Overnight | $1.0 \times 10^5$ | $8.7 \times 10^4$ |

The sample at 0 hour was taken prior to IPTG addition. The parent nuc* gene and the mutant derivative are both positioned within the Tn5 transposon, and it is therefore possible to transfer them to other bacterial species as described in Example 11 below. Each of the three plasmids described in Example 10 below were conjugated from *E. coli* S17.1 (donor strain) to *Pseudomonas putida* and *Pseudomonas fluorescens*, respectively.

After isolation of transconjugants and colony purification, a number of independent clones from each conjugation were tested for IPTG induced growth inhibition. For each specific combination of transposon and recipient there was no variation, indicating that independent of the transposition to the recipient the effect of induction was the same. The general picture mimics that observed in *E. coli*: The mutant is more effective as growth inhibitor even in the Pseudomonads, than the wild type.

EXAMPLE 8

Construction and Testing of a Model Recombinational System

A model plasmid for evaluation of the potentials for a stochastic induction system based on homologous recombination was constructed. The plasmid is based upon the well characterized plasmid pBR325 (Bolivar, 1978, Gene, 4, 121–136), where the chloramphenicol resistance gene is repeated. Between the two stretches of homologous DNA is inserted the lacIQ gene from a commercial plasmid, pTTQ19, (Stark 1987, 10 Gene, 51, 255-267). If another gene, controlled by a promoter which is repressed by lacI is residing in the same cell as is the model plasmid, mentioned above, (and the strain background is lacI)—then an induction of that gene will occur when the last copy of the model plasmid is recombined as the LacI repressor is lost in the process. The vector pBR325 typically exists in 50 copies per cell.

A. Construction of the Model Plasmids pCK24 and PCK25 pBR325 was linearized with EcoRI and the sticky ends were filled in by means of the large fragment of the DNA polymerase I (Klenow fragment). The plasmid was religated, resulting in pCK20, which confers ampicillin and tetracyclin resistance but not chloramphenicol resistance to the host cell. The same procedure was conducted on the plasmid pSUP202 (Simon et al., 1983, Biotechnology, 1, 784–790), resulting in pSM865. The chloramphenicol gene was cloned from the central BbvI fragment of Tn9, which was blunt ended. This fragment was inserted into the blunt ended XbaI site of pUC18 (Yanisch-Perron et al., 1985, Gene, 33, 103–109), giving pLKP46. The orientation of the fragment was determined by the internal EcoRI site which is proximal to the BamHI site of pUC18. Into the vectors pCK20 and pSM865, cut with BamHI and SalI, were inserted the BamHI/SalI fragment of pLKP46, giving the chloramphenicol resistant but tetracycline sensitive plasmids pCK22 and pCK23, respectively.

The plasmid pHB103 comprises the lacIQ gene from the plasmid pTTQ19. The excised LacIQ fragment is identical to the SspI/Eco0109I fragment with the following modifications: The Eco0109I site was blunt ended and ligated to a SalI linker (New England Biolabs, Inc. #1027) and subsequently, to the small SalI-BamHI fragment of pKK223-3 (Brosius et al., 1984, Proc. Natl. Acad. Sci. U.S.A., 81, 6929–6933). Thus, the resulting lacIQ fragment is residing on a approximately 1100 base pair SspI/BamHI fragment. This fragment was inserted into pCK22 and pCK23 cut with EcoRV and BamHI, giving pCK24 and pCK25, respectively. These plasmids are the model plasmids, and differs in that pCK25 additionally contains the mob gene (approximately 2000 base pairs) inserted between the two direct repeats, together with the LacIQ gene. The stretches that are homologous in the two plasmids are approximately 900 base pairs, and the inter repeat stretches are approximately 1100 base pairs (pCK24) and approximately 3100 base pairs (pCK25).

Figure 5:
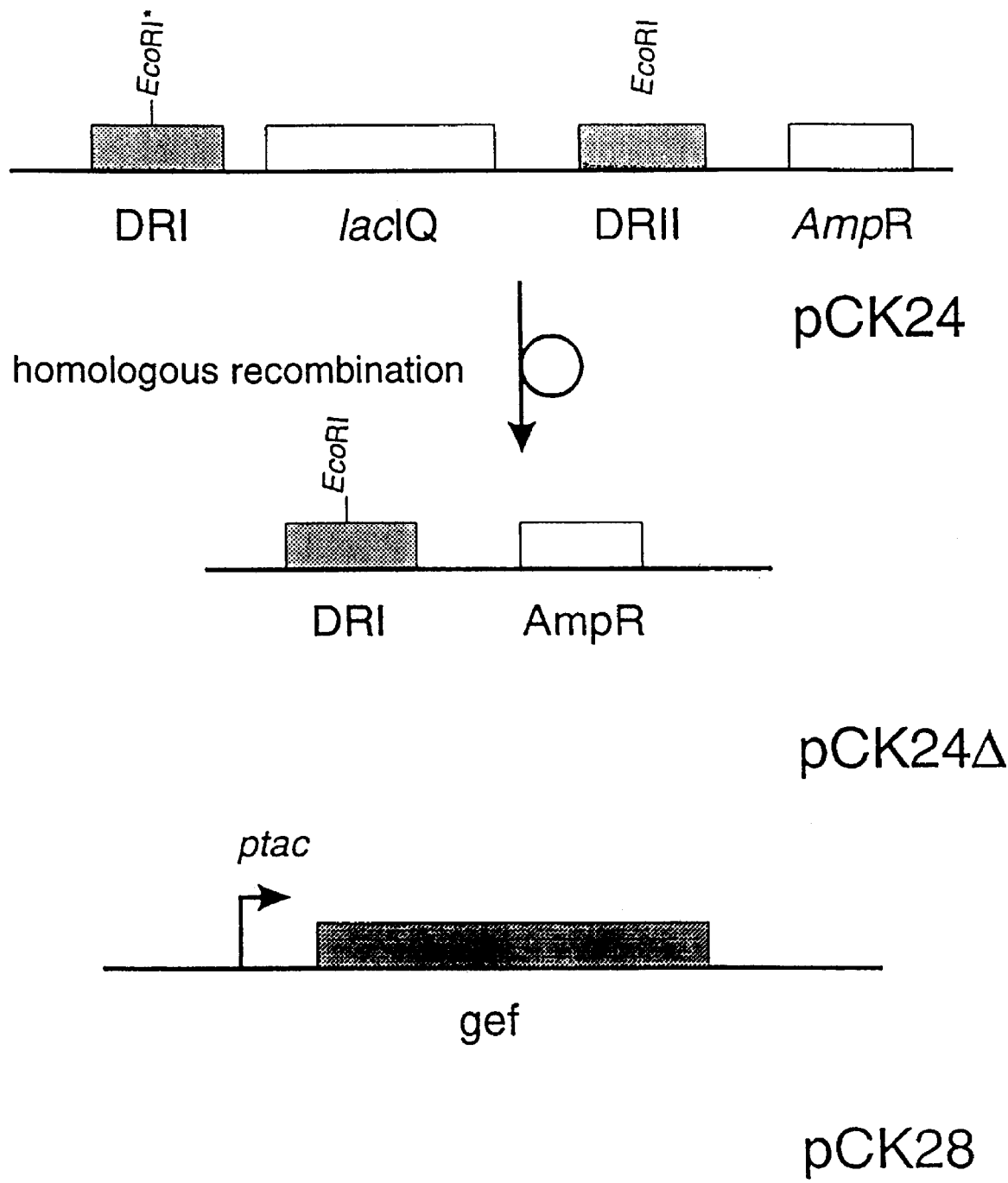
FIG. 5 shows a schematic representation of pCK28 which, when present in a cell with pCK24 from which the lacIQ repressor gene has been deleted as the result of homologous recombination, may express a killing function (gef gene product)

An additional plasmid, containing the gef gene under the control of a LacI repressible promoter, the trp-lac hybrid tac promoter (Amann, E. et al., 1983, Gene, 25, 167–178), was constructed. The plasmid pLKP118 (Poulsen et al., 1989, Molec.Microbiol., 3, 1463–1472) containing the gef gene, was digested with HindIII and EcoRI and ligated to pKK233-3 opened in HindIII and EcoRI, resulting in pHB11. The approximately 500 base pair BamHI fragment of pHB101 was inserted into the BamHI site of pACYC177 (Chang et al., 1978, J.Bacteriol., 134, 1141–1156), giving pCK28 (FIG. 5).

B. Determination of the Model Plasmid Physiology in Stationary Phase and in an Adapted Continuous Exponential Growth Phase The model plasmids pCK24 and pCK25 were transformed into the *E. coli* strain CSH36 (Cold Spring Harbour collection, USA), which has a delta(lac-pro) deletion on the chromosome and further harbours the F-factor, containing the complete lac-operon, except for a functional lacI gene. The strain phenotype is thus blue on plates containing 5-bromo-4-chloro-3-indolyl-β-D-galactopyranoside (X-gal), provided no lacI gene is residing in the cell.

The phenotype of the cells transformed with pCK24 or pCK25, when plated on X-gal plates were white, blue and blue sectored colonies, indicating that cells in the blue parts of the colonies had indeed deleted all the copies of the lacIQ in the model plasmids. When restreaking uniformly white colored colonies on X-gal plates, they too become sectored over night. Uniformly blue colored colonies, however, remained blue.

From plates described above, several white colonies were picked and resuspended in 2 ml of isotonic NaCl solution. From this solution aliquots of 0.2 ml were distributed as one large drop onto LB-plates and incubated at 37° C.

One aliquot was frozen immediately. The plates were then harvested on day one after inoculation and on the following days, with intervals of two or more days. The plates were harvested by adding 2 ml isotonic NaCl to the plates and resuspending the cells herein. The suspension was collected, spun and the resulting pellet resuspended in 0.2 ml NaCl. The harvested cells were kept frozen at −20° C. until the end of the experiment. After approximately 15 days, the cells were thawed and used for a DNA mini-preparation (a.m. Birnboim, H. C. and J. Doly, 1979, Nucleic Acids Res., 7, 1513–1523).

For assaying the genotype of the entire plasmid population, a recA deficient variant of CSH36 was constructed: CSH36 was P1 transduced with a phage stock prepared from the delta-recA::Tn10 strain JC10284 (Czonka et al., 1979, Genetics, 93, 321–343), giving CKE95.

Figure 6A:
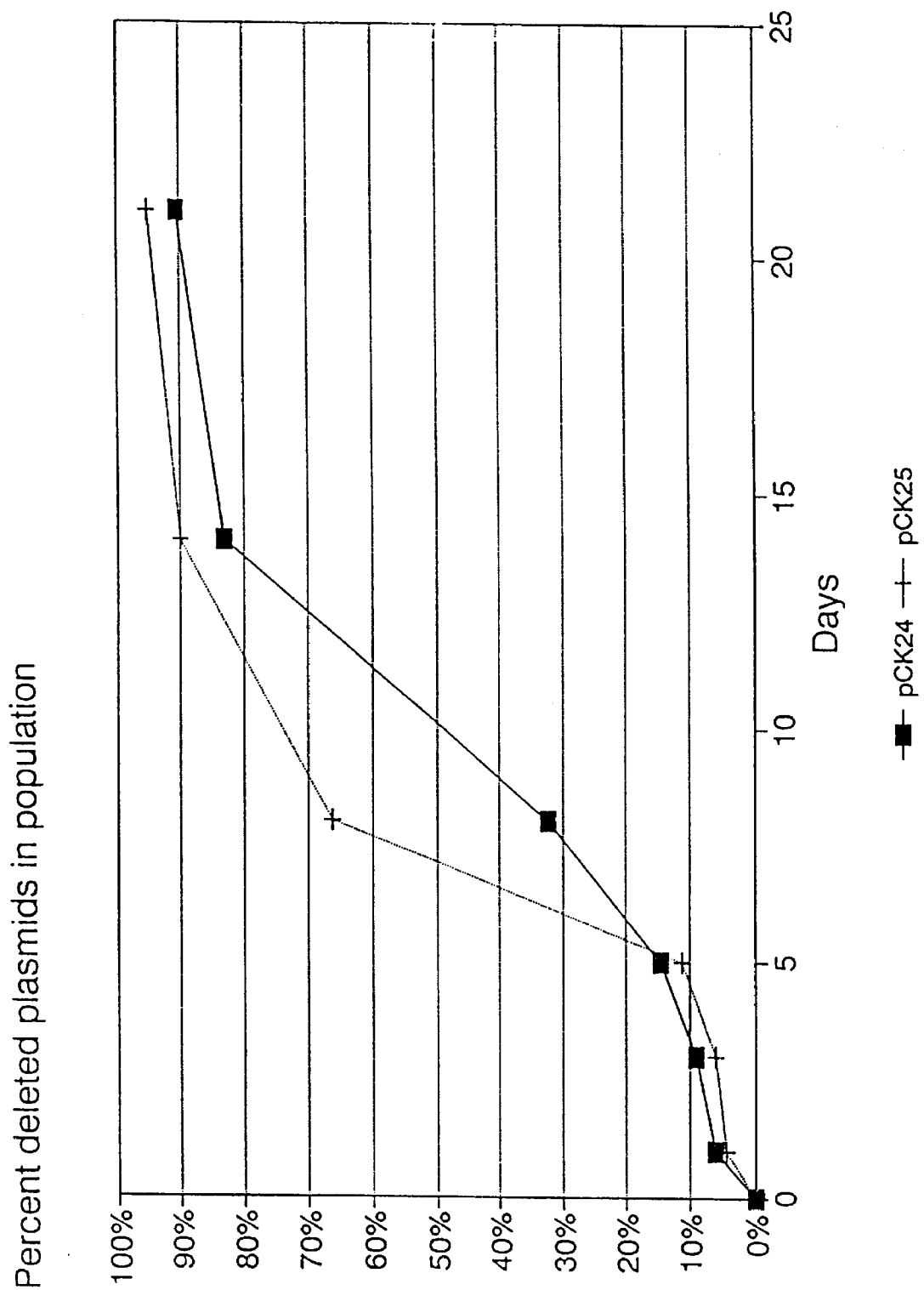
FIG. 6A shows the rate of recombination of pCK24 and pCK25, both contained in stationary phase E. coli CSH36, grown at 37° C. on LB plates containing 100 µg/ml ampicillin. Cells were harvested at the indicated times and retransformed into E. coli CKE95, a recA deficient mutant of CSH36. Plasmids from retransformants were digested with PstI. The resulting fragments were analyzed in a gel, and the relative intensities of the resulting bands was calculated as a measure of the percentage of plasmids with recombinational deletions.

Into CKE95 were transformed DNA samples from the plates described above, and the colony colour upon plating on X-gal was evaluated. The percentage of blue colonies correlated directly to the fraction of recombined plasmids in the corresponding DNA samples. When plotted (FIG. 6) a clear progression in the recombination could be recognized, indicating that the recombination system is active in stationary phase CSH36 cells. After 14 days, more than 80 percent of the plasmids in the population were recombined. There was no significant difference between the behaviour of pCK24 and pCK25.

Figure 6B:
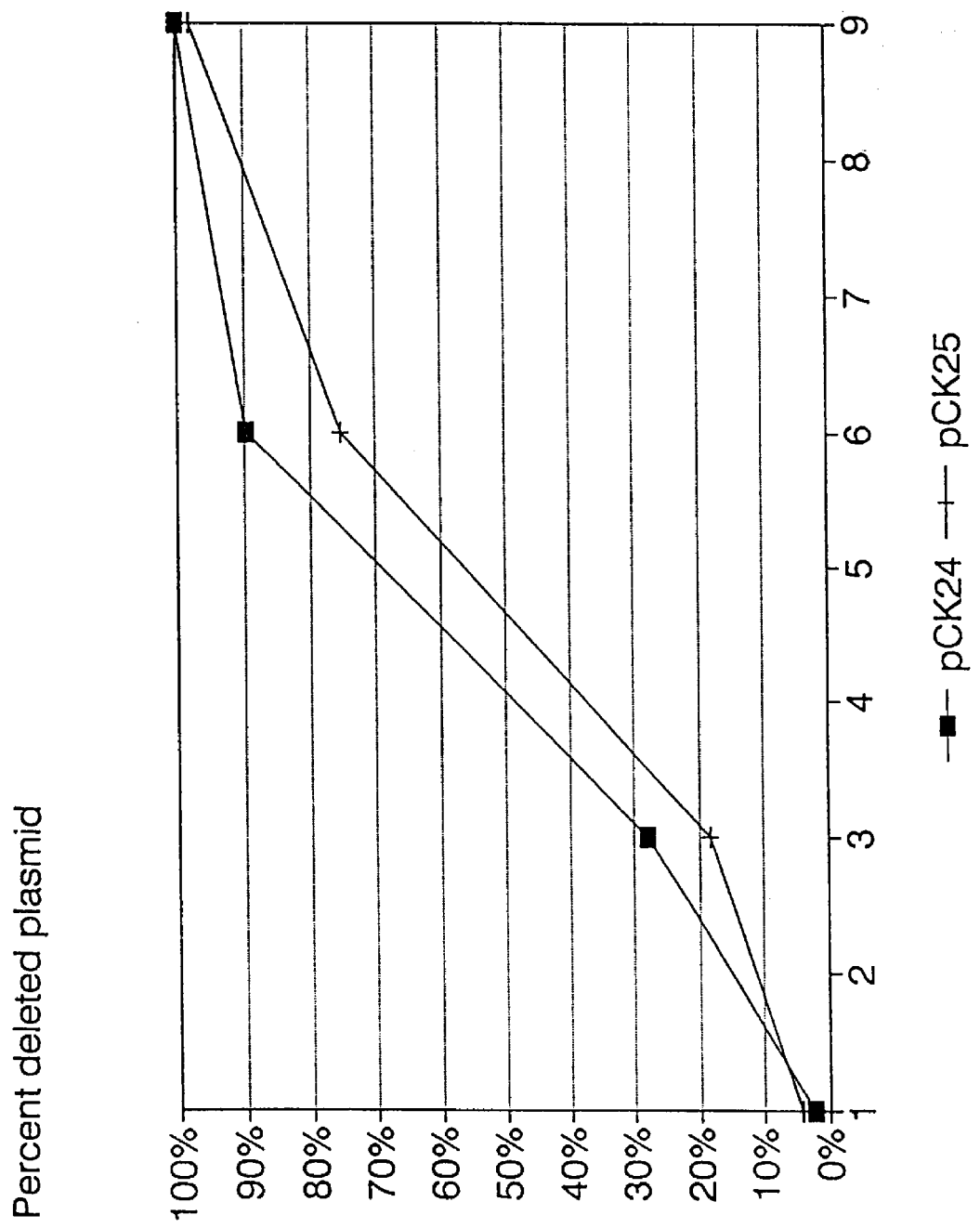
FIG. 6B shows the rapid progression in plasmid recombination in growing E. coli CSH36. The plasmid bearing strain was reinoculated once a day by a 1:100 inoculum in LB media containing 100 µg/ml ampicillin, and samples were withdrawn for DNA preparation with intervals of several days. The DNA was restricted with PstI and analyzed in a gel and the relative intensities were calculated as the relative percentages of plasmids with recombinational deletions.

The recombination rate was evaluated in a simulated continuous exponential growth experiment, where CSH36+pCK24 and CSH36+pCK25 cells were grown i LB medium supplemented with 100 μg/ml ampicillin, at 37° C. and shaking overnight and reinoculated in fresh LB medium every morning, using 1:100 inoculum. At the time of reinoculation, a fraction of the overnight culture was immediately used for a DNA mini-preparation. At the end of the experiment, the DNA samples was digested with PstI, which is unique in both model plasmids and located outside of the region which is deleted in the recombination process. The relative intensity of the two resulting bands from one DNA sample is a direct measure of the proportion of recombined to intact plasmid. One such experiment showed that the percentage of recombined pCK24 plasmids went from virtually nil to 90 percent in six days. After nine days essentially all plasmid in the culture had undergone rearrangement as assayed by gel-scanning. pCK25 behaved similarly. This indicates that the recombination system is active in exponentially growing cells (FIG. 6B).

This experiment was also conducted in the common laboratory *E. coli* strains C600 (Bachmann, 1987, in *Escherichia coli* and *Salmonella typhimurium* ed. Neidhard, F. C. et al. ASM, pp. 1190–1219) and MC1000 (Silhavy et al., 1984, Experiments with Gene Fusions, Cold Spring Harbour Laboratory, New York, pp. xi–xii). A progression of recombination could be observed in these strains as well, by visually inspecting DNA digest gels as described.

C. Experiments Using a Lac-Repressed Gene, gef in Trans

The CSH36 strains, harbouring pCK24 or pCK25 were transformed with pCK28, which contains the gef gene under control of the tac promoter on a compatible plasmid. When the last copy of lacIQ is excised by recombination, the promoter is derepressed and expression of the toxic gef-protein commences, causing the host cell to die. By streaking CKE95/pCK24/pCK28 and CKE95/pCK25/pCK28 together with the appropriate controls (CKE95/pCK24/pACYC177 and CKE95/pCK25/pACYC177) on minimal plates containing either 0.2% glucose, 0.5% glycerol or 0.5% acetate as sole carbon source and supplemented with chloramphenicol (50 μg/ml) and kanamycin (50 μg/ml) a significant growth inhibition could be observed for the strains containing the gef-plasmid. The lesser the quality of the carbon source, i.e. the slower overall growth rate, the more severe is the inhibitory effect. This experiment indicates that the stochastic induction system can be used in the context of containment on a laboratory basis, as a setup as described confers a significant disadvantage to cells containing the gef plasmid.

To test the combined strains further, the cell doubling time of CKE95/pCK24/pCK28 was compared to that of CKE95/pCK25/-pACYC177. The experiments were conducted in minimal medium containing 0.2% glucose supplemented with chloramphenicol (50 μg/ml) and kanamycin (50 μg/ml) and with or without casamino acids. In minimal medium with casamino acids, the doubling time of the strain containing the gef-plasmid was 45 minutes as compared to 43 minutes for the control. In minimal medium without casamino acids the doubling times were 93 and 85 minutes, respectively. This experiment verified the tendency seen on the minimal plate assay above.

EXAMPLE 9

Construction of Plasmids for Making Up a Toolbox for the Construction of Insertion Plasmids Containing a Direct Repeat Cassette Brief overview of the components of the system:

The system is based upon assembling two separately constructed plasmids:

A) First half consists of a cassette with a promoter directed towards a sequence of DNA which is of variable length, typically 600–1500 bps. This sequence is to be the actual repeated DNA. After this stretch of DNA is, optionally, a resistance factor, e.g. the chloramphenicol gene. Finally, hereafter, a transcription terminator is inserted 5' to the two restriction sites XhoI-SphI in that order.

B) The second half consists of a sequence identical, at least in part, to the above-mentioned repeated sequence, followed, optionally, by a killing gene or an indicator gene (or nothing). This cassette is flanked by unique XhoI and SphI sites, which enables this cassette to be inserted into the first half, described above. The complete "recombination cassette" is flanked by two NotI sites, which enables it to be excised and reinserted into a suicide delivery plasmid for integration of the cassette into the chromosome of the host cell by a Tn5 transposition mechanism.

A. Construction of a Series of Recombination-Cassette Type Plasmids With a 598 Base Pair Repeat Two basic cloning vectors, pUC18Not (Herrero et al. 1990, J.Bacteriol., 172, 6557–6567) and pUC19 (Yanisch-Perron et al. 1985, Gene, 33, 103–109) were modified by exchanging their polylinker sequences. Into the SacI/PstI cut pUC18Not was inserted the synthetic polylinker 5,'-CTGCAGTCCCGGGTGTCGACAGATCTA-GACATGCATCTCGAGTGCA (SEQ ID NO:3) (upper strand), destroying the original PstI site but retaining the SacI site, resulting in pCK29.

Likewise, the SacI/SphI cut pUC19 was ligatec to the synthetic polylinker 5'-CTCGAGGATCCTCCCGGGAGATCTGCATG (SEQ ID NO:4) (upper strand), retaining SacI as well as SphI, resulting in pCK30.

pCK29 was cut with NsiI and a 250 bp PstI fragment from the plasmid pHBA102rpoCt, containing the rpoCt' transcription terminator (Squires et al. 1981, Nucleic Acid Res., 9, 6827–6839) was inserted, the internal BglI site proximal to the BglII site of pCK29, resulting in pCK45.

The chloramphenicol resistance gene was cloned from the central BbvI fragment of Tn9, which was blunt ended by means of the large fragment of the DNA polymerase I (Klenow fragment). This fragment was inserted into the blunt ended XbaI site of pUC18 (Yanisch-Perron et al., supra) giving pLKP46. The orientation of the fragment was determined by the internal EcoRI site which is proximal to the BamHI site of pUC18.

pLKP46 was cut with SmaI and SalI and the fragment containing the chloramphenicol resistance gene was inserted into the pCK45 linearised with SmaI and SalI, giving pCK49.

Figure 7:
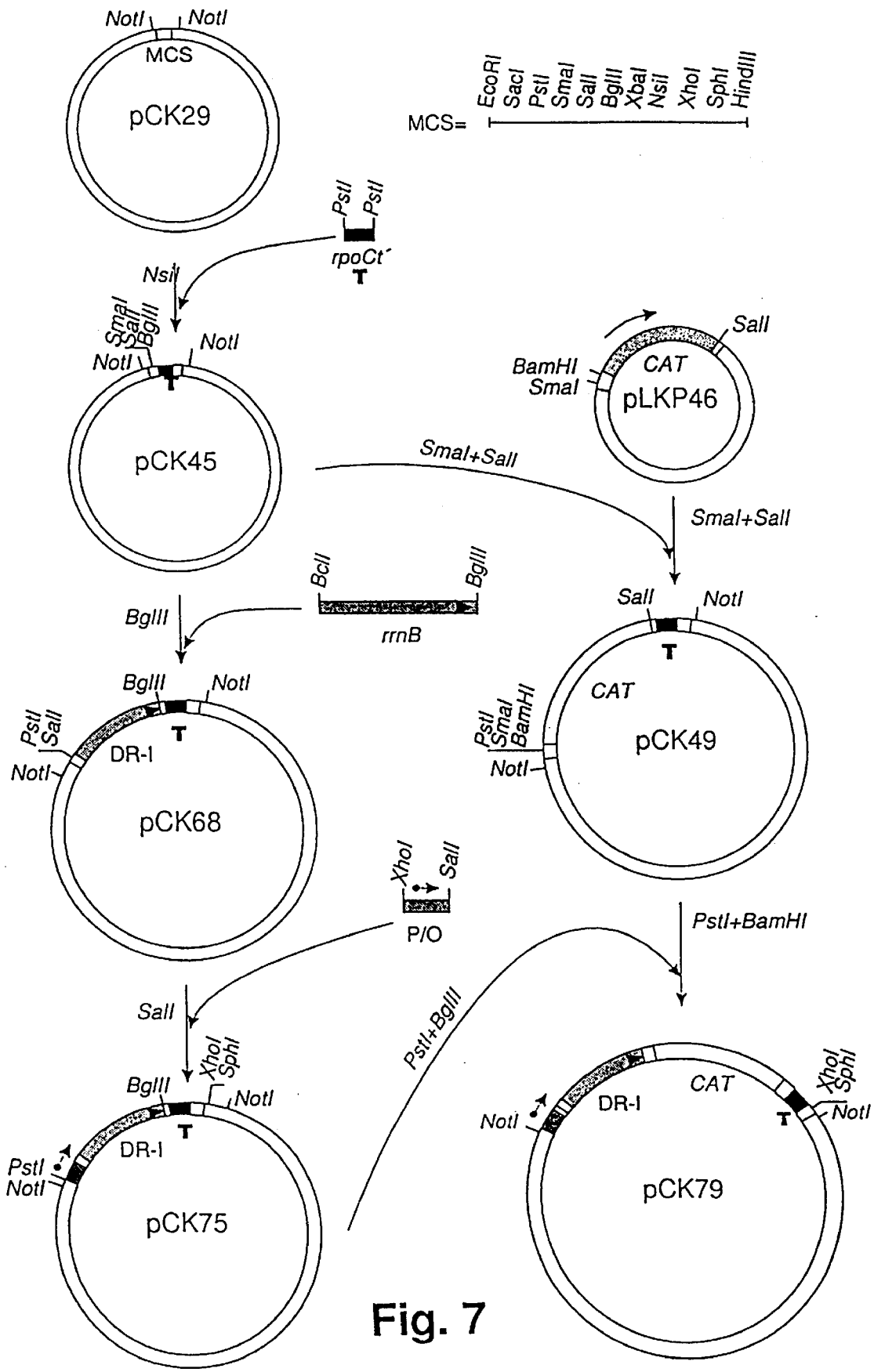
FIG. 7 shows a schematic representation of the construction of plasmid pCK79.

A 690 bp BclI-BglII fragment from the plasmid pKK3535 (Brosius et al. 1981, Plasmid, 6, 112–118), containing part of the 16S rrnB gene, was inserted into the BglII site of pCK45, with the BglII site recreated proximal to the rpoCt' sequence of pCK45 described above, giving pCK68.

pCK68 was linearised with SalI and a 127 bp XhoI/SalI fragment from pUHE24-2 (Lanzer et al. 1988, Proc.Natl.Acad.Sci. USA, 85, 8973–8977) containing the $p_{A1/04/03}$ promoter was inserted. The SalI site was recreated proximal to the inserted ribosomal sequence in pCK68, giving pCK75. pCK75 was cut with PstI and BGLII and the smaller fragment was inserted into pCK49 cut with PstI and BamHI, giving pCK79 (cf. FIG. 7).

Figure 8:
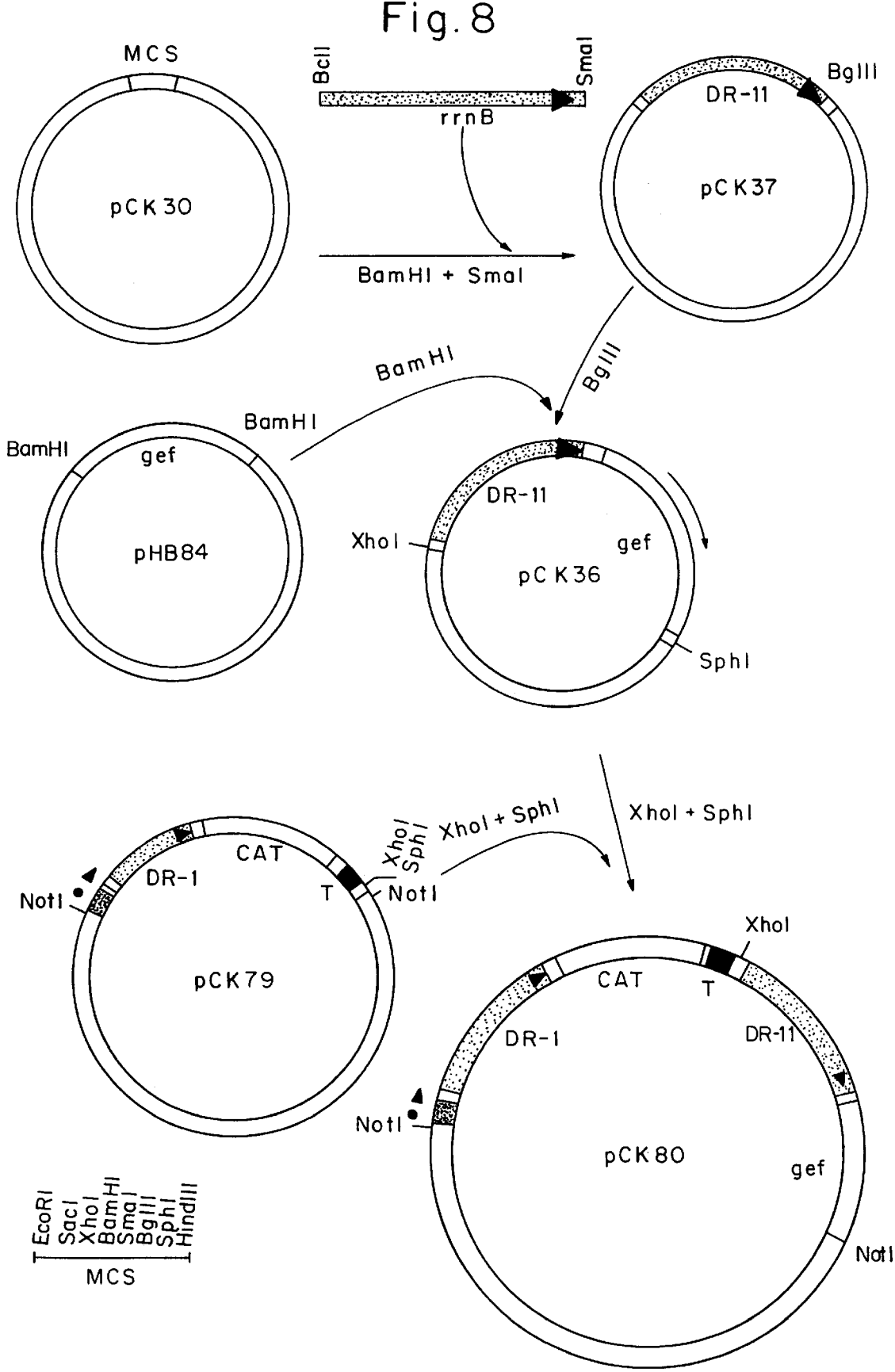
FIG. 8 shows a schematic representation of the construction of plasmid pCK80.

The two plasmids pCK75 and pCK79 (cf. FIG. 7) are the basic plasmids for constructing the recombination cassette (first half, 598 bp repeat).

pCK30 was cut with BamHI and SmaI and a 598 bp BclI-SmaI fragment from pKK3535 was inserted, resulting in pCK37 (FIG. 8).

Various plasmids containing genes to be expressed upon recombination were modified for use in the system. The plasmid pCB267, containing the lacZ gene (Schneider et al. 1987, Meth. Enzymol., 153, 452–461), was linearised with Eco0109I and blunt ended as described above, and ligated to a BamHI linker (New England Biolabs, Inc. #1021), resulting in pCK52.

The plasmid pSM1088, containing the nuclease gene (nuc*, nuclease gene devoid of its proprietary leader sequence (described in a previous example), was treated likewise: the HindIII and EcoRI sites were sequentially blunt ended and ligated to the BamHI linker described, resulting in pCK53 and pCK59, respectively.

Into the BglII site of pCK37 was inserted:

a) the approximately 3000 base pair BglII-BamHI fragment of pCK52, containing the lacZ gene, the BglII site recreated distal to the SphI site of pCK37, giving pCK56.

b) the approximately 1100 bp BamHI fragment of pCK59, containing the nuclease gene, the internal EcoRV site of the fragment distal to the SphI site of pCK37, giving pCK63.

c) The approximately 400 base pair BamHI fragment from the plasmid pHB84, comprising the gef gene, the EcoRI site of the fragment distal to the SphI site of pCK37, giving pCK36 (FIG. 8). pHB84 was created by inserting a BamHI linker (New England Biolabs #1021) into the blunt ended EcoRI site of the plasmid pLKP118 (Poulsen et al. 1989, Molec.Microbiol., 3, 1463–1472).

d) Nothing (i.e. pCK37 itself).

These four plasmids were used as the basic plasmids in the construction of the recombination cassette (second half, 598 bp, containing killing function, indicator gene or no marker).

B. Assembly of the Recombination Cassette and Making of Integration Plasmids

The XhoI/SphI fragments of the four basic plasmids described above was introduced into pCK79 cut with XhoI and SphI, resulting in the plasmids pCK82, pCK95, pCK80 and pCK81, respectively (cf. FIG. 9). From these plasmids, the NotI fragments containing the recombination cassette was ligated into the unique NotI site of the suicide vectors pUT-mini-Tn5-Tc and pUT-mini-Tn5-Km (de Lorenzo et al. 1990, J.Bacteriol., 172, 6568–6572), giving the vectors:

| vector | pUC18Not | pUTTc, | pUTKm |
|---|---|---|---|
| p->DR-CmR-DR-gef | pCK80 | pCK84 | pCK80 |
| p->DR-CmR-DR- | pCK81 | pCK85 | pCK88 |
| p->DR-CmR-DR-LacZ | pCK82 | pCK86 | pCK89 |
| p->DR-CmR-DR-nuc* | pCK95 | pCK96 | pCK97 |

The plasmid pCK81 contained in *E. coli* K12 MC1000OrecA was deposited on 5 Jul., 1991 with Deutsche Sammlung von Mikro-organismen und Zellkulturen GmbH (German Collection of Micro-organisms and Cell Cultures), Mascheroder Weg 1B, 38124 Braunschweig, Germany.

EXAMPLE 10

Construction of Recombination Plasmids With Longer Stretches of Repeated DNA

In order to provide a more versatile toolbox for future constructions, derivatives were made to facilitate easy and fast modification of the main system parameter: repeat length. A long stretch of rrnB-DNA was inserted into the vectors pCK29 and pCK75. By cutting at a desired position in the rrnB and, if necessary, blunt end the opened vector, and following cutting at the unique PstI site, the obtained fragment can be inserted into pCK45 or pCK49, opened in PstI/SmaI. Likewise a series of plasmids containing the gef, nuc* and LacZ, but without a rrnB sequence was created. In these plasmids, the desired length repeat is excised directly from pKK3535 as a blunt end to BclI fragment and subsequently inserted into the plasmids.

To obtain the plasmids for the first half of the system (direct repeat I), pCK29 and pCK75 were opened in BglII and SphI. Into pCK29 the 3196 base pair BclI/SphI fragment of pKK3535 was inserted, giving pCK72. The 2506 base pair BglII/SphI fragment of pKK3535 was inserted into pCK75 (which already contains part of the rrnB sequence), giving pCK83.

Figure 10:
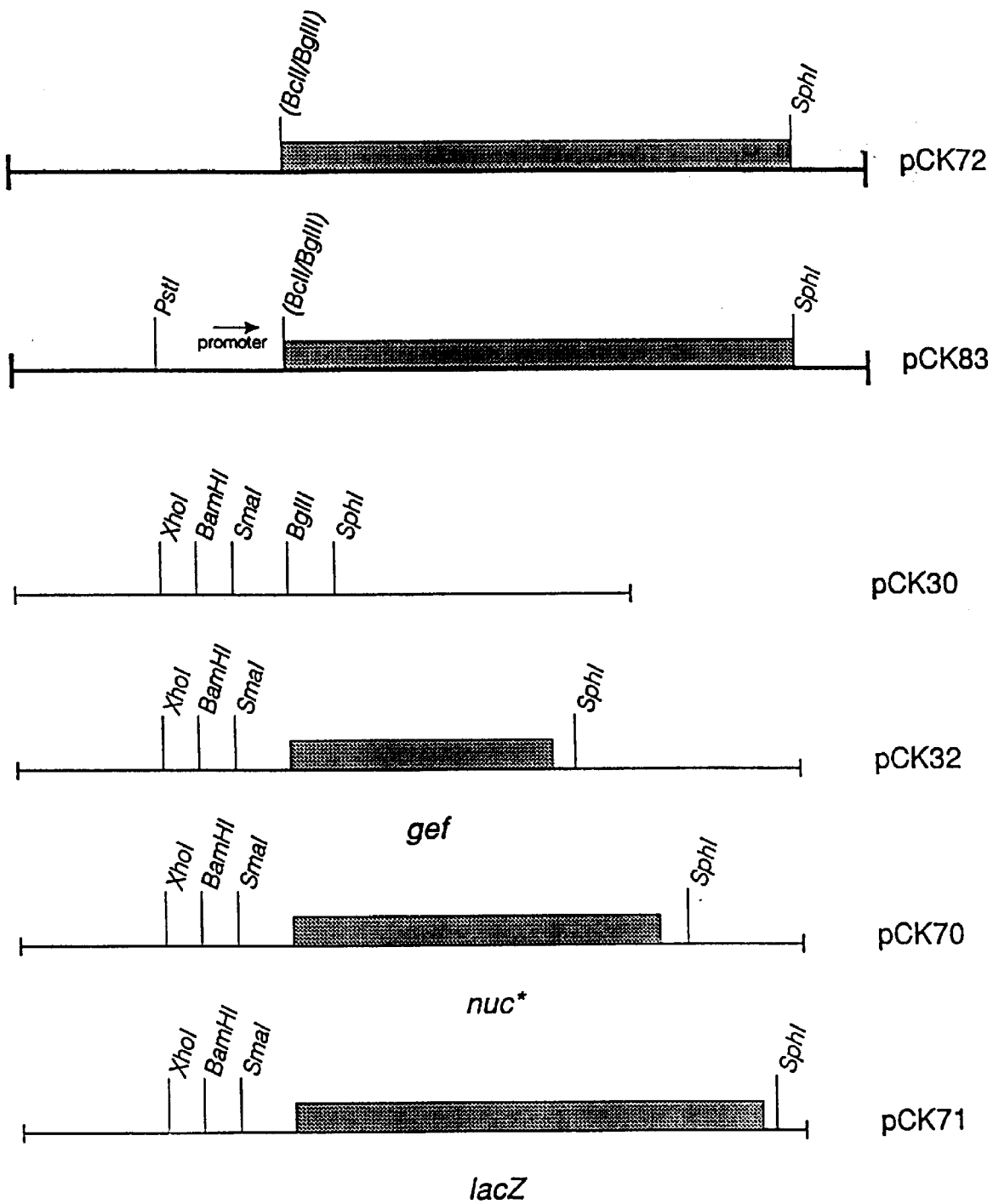
FIG. 10 shows a schematic representation of plasmids pCK72, pCK83 and plasmid pCK30 and the recombination plasmids pCK32, pCK70 and pCK71, derived from pCK30.

Into pCK30 linearised at the BglII site the following fragments were inserted (cf. FIG. 10):

a) the BglII/BamHI fragment of pCK52 containing the LacZ gene, giving pCK71, the recreated BglII site being proximal to the SmaI site of pCK30.

b) the BamHI fragment of pCK59 containing the nuc* gene, giving pCK70, the internal EcoRV site proximal to the SmaI site of pCK30.

c) the BamHI fragment of pHB84 containing the gef gene, giving pCK32, the internal EcoRI site proximal to the SmaI site of pCK30.

d) nothing (i.e. pCK30 itself).

EXAMPLE 11

Construction of Strains of Different Genera by Insertion of the RUT-Derivatives

By using the pUT-based vectors, the constructs can be inserted into the chromosome of virtually any gram-negative bacterium, thus obtaining a stable maintenance of the cassette as it is replicated together with the host chromosomal DNA. This integration feature makes the system independent of the requirement of compatibility of vector/host relations. The vectors pCK84-89 were successfully integrated into the chromosome of *Pseudomonas putida* and *Pseudomonas filuorescens*. The pUT plasmids require a pir-protein to replicate. The replication origin of the pUT plasmids is derived from the broad host range plasmid RP4 which also encodes the pir-protein. The pUT plasmids do not encode the pir-protein and the protein is thus required in trans if the plasmid is to exist extrachromosomally. A derivative of the *E. coli* strain S17.1 (Simon et al., 1983, Biotechnology, 1, 784–79D) into the chromosome of which the lambda phage containing the pir gene has been integrated, was used for conjugal transfer of the plasmids to other species. The S17.1 strain containing the appropriated plasmid was mixed with recipient strain on an LB agar plate and the mixture was left for 1-2 days at a temperature not exceeding 30° C. to prevent the lambda phage from entering the lytic phase.

Exconjugants were subsequently selected on plates which are selective for the recipient strain (e.g. containing rifampicin) and the transposon part of the integration plasmid (tetracycline or kanamycin). The integration was verified by plasmid DNA preparation from exconjugants.

EXAMPLE 12

Preliminary Experiments With the pCK Recombination Plasmids pCK82 was transformed into MC1000 (rec-proficient, delta-lacX74) and the transformation mixture was streaked onto LB agar plates containing 100 µg/ml of ampicillin and 50 µg/ml X-gal. After a few days, several blue colonies could be detected and additionally, several blue-sectored colonies which was an indication that the recombination system was functional as expected.

The plasmids pCK80-82 and pCK79 (as a control) were transformed into MC1000 and one colony of each type was streaked onto ABTG plates or ABT+0.5% glycerol plates supplemented with 20 mg/L leucine and 100 µg/ml of ampicillin. On the ABT+glycerol plates the cells containing the pCK80 (gef) grew more slowly than the three other strains. On ABTG, no difference was recognizable.

pCK86 and pCK89 were integrated into the chromosome of *Pseudomonas putida* and when streaked onto LB plates containing 50 µg/ml X-gal the host cells gave initially white colonies but distinctly blue colonies after a few days of incubation. The 600 base pair repeat and the effect of integrating the cassette into the host cell chromosome lowers the recombination frequency significantly as indicated by the lower ratio between blue and white colonies as compared to having the cassette located on an extrachromosomal plasmid.

EXAMPLE 13

Intracellular Expression and Development of a Conditional Cell Function-Limiting System in *Escherichia Coli* Using a Nuclease Gene from *Staphylococcus Aureus*

A. Bacterial Strains, Plasmids, Oligonucleotides Used

*E. coli* JM109 was purchased from Invitrogen Inc., San Diego, Calif. Plasmid PFOG 408 containing the nuclease gene of *Staphylococcus aureus* Foggi strain was a gift from A. Meeker. The cloning vector plasmid pUHE24-2 was obtained from S. Molin. The oligonucleotides for PCR amplification were custom-synthesized by GENOSYS Inc., USA.

B. PCR Amplification of the Nuclease Gene

The nuclease gene from the plasmid pFOG 408 without its signal sequence was PCR amplified using two oligonucleotide primers L-SNUC and R-SNUC. The primer L-SNUC was 37 nucleotides long (5'GATCCGG-ATCCGCAACTTCAACTAAAAAATTACATAA-31) (SEQ ID NO:5) with a 11 nucleotide overhang at the 5'-end consisting of BamHI, AccII, and HpaII restriction endonuclease sites. The primer R-SNUC was 33 nucleotides long (5'-GGTACCGGAATTCGTGCCACTAGCAGCAGTGAC-3') (SEQ ID NO:6) with EcoRI, HpaI, and KpnI restriction endonuclease sites. PCR amplifications were performed in a DNA thermal cycler 480 (Perkin Elmer Cetus) using Ampli-Taq DNA polymerase (2.5 units) (Perkin Elmer Cetus), 200 µM of each of the dNTPs (Pharmacia), PCR reaction buffer (1OX reaction buffer contained 500 mM Tris.HCl [pH 8.9], 500 mM KCl, and 25 mM MGCl$_2$), and 0.5 µM of each of the primers. The PCR amplification was performed for a total of 25 cycles, each cycle consisting of 1 min denaturation at 94° C., 1 min primer annealing of 55° C., and 1 min primer extension at 72° C. Successful PCR amplification of a 0.507 kb DNA fragment was determined by running 1 Seakem agarose gel (FMC Bioproducts), stained with EtBr, and visualized under a UV transilluminator.

PCR amplification using the primers L-SNUC and R-SNUC produced a single DNA band of 0.507 kb in size indicating no non-specific priming. The upstream primer L-SNUC was designed precisely so that it would prime the first nucleotide of the first amino acid residue after the signal sequence of the gene (cf. the sequence defined above). Moreover, a 11 bp overhang at the 5'-end of the primer ensured the synthesis of the gene from the desired nucleotide; thus eliminating the possibility of frameshift mutation during PCR amplification. The downstream primer R-SNUC was located further downstream of the stop codon and the possible hairpin structure outside the coding sequence of the gene, ensuring that all the amino acid including the stop codon of the gene remain intact and functional.

C. Cloning of the Amplified Nuclease Gene

The amplified DNA of the staphylococcal nuclease gene without its signal sequence was end-repaired with DNA polI Klenow fragment to create blunt ends as described by Ausubel et al (1987). The end-repaired blunt ended amplified nuclease gene was purified by using a Centricon 100 microconcentrator (Amicon, Ma.). pUHE24-2 was linearized with BamH1, end-repaired to create blunt-ends and purified by following the procedures described by Ausubel et al (1987). Cloning and transformation of the cloned DNA into *E. coli* JM109 was performed as described by Ausubel et al (1987). The transformed colonies were screened for the appropriate clones by replica plating on DNAse test agar (Difco) plates containing methyl green as indicator dye, 40 µg ampicillin per ml, 1 mM Isopropyl-β-D-thigalactopyranoside (IPTG), 10 mM CaCl$_2$, and 1 mM MgCl$_2$.

Colonies which produced indicator colour were further tested for clones by restriction analysis, PCR amplification, and DNA sequence analysis. Plasmid DNAs from the putative clones, designated as pSNUC-1 and pSNUC-3 were isolated and purified by alkaline lysis method as described by Ausubel et al (1987). The isolated plasmid DNAs were digested with HindIII restriction enzyme (US Biochemicals) according to the manufacturer. The restriction enzyme digested plasmid DNAs were analyzed by 10% polyacrylamide gel electrophoresis, stained with EtBr, and visualized by a UV transilluminator. The nucleotide sequence analysis of the cloned fragments in both plasmids, pSNUC-1 and pSNUC-3, were determined by Sanger dideoxy method (Sanger et al, 1977) using a sequenase sequencing kit (US Biochemicals) and the L-SNUC primer. These two clones were further characterized for induction and expression of the nuclease. Also they were tested for their ability to grow on LB agar plates containing ampicillin (40 μg per ml), 10 mM $CaCl_2$, 1 mM $MgCl_2$, with or without 1 mM IPTG.

Figure 11:
FIG. 11 shows the growth and phenotypic expression of the pUHE24-2 derived staphylococcal nuclease gene without its signal sequence in E. coli JM109 containing pSNUC-1 without (right plate) and with (left plate) induction with IPTG.
Figure 12:
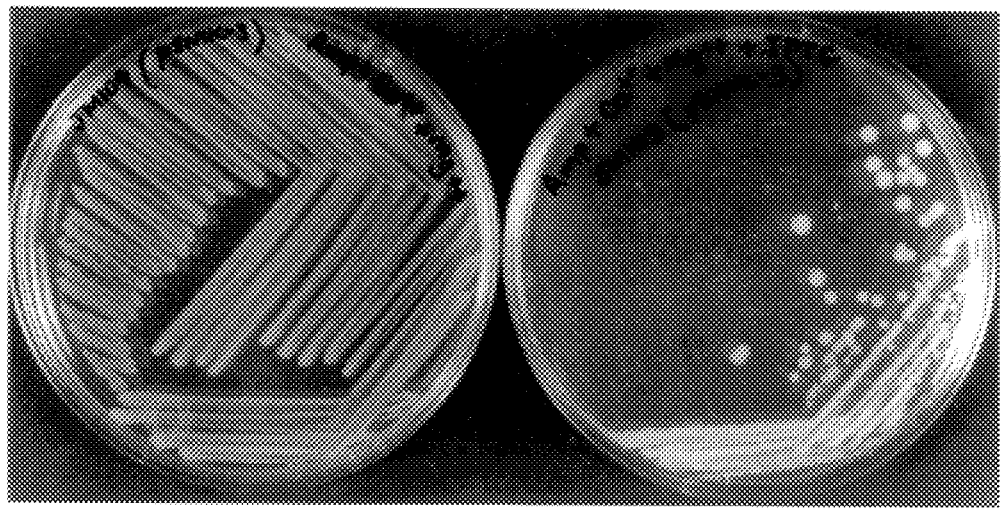
FIG. 12 shows the growth and phenotypic expression of the pUHE24-2 staphylococcal nuclease gene without its signal sequence in E. coli JM109 containing pSNUC-3 without (right plate) and with (left plate) induction with IPTG.
Figure 13:
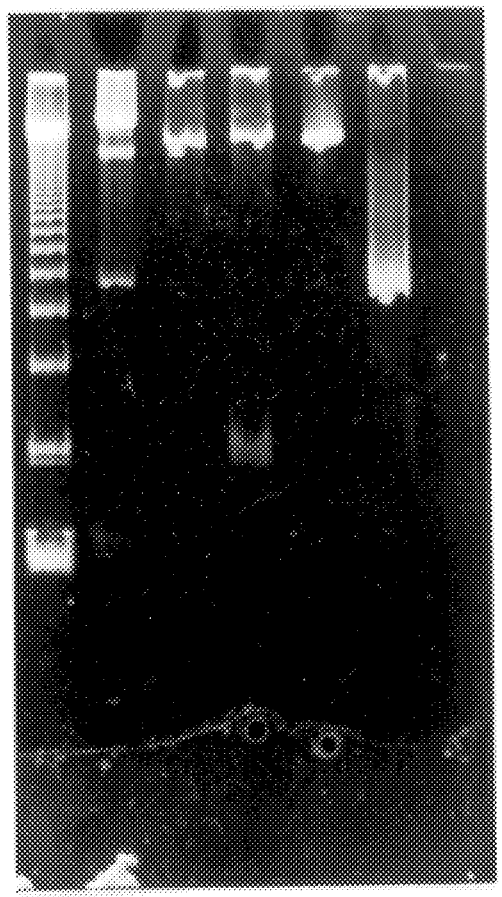
FIG. 13 shows a polyacrylamide gel electrophoresis analysis of the pUHE24-2 nuclease gene without its signal sequence cloned in the pUHE24-2 plasmid vector. Lane 1, 123 bp DNA ladder as size standard; lane 2, lambda DNA digested with HindIII restriction enzyme as size standard; lanes 3 and 5, pUHE24-2 digested with HindIII; lane 41 plasmid pSNUC-1 digested with HindIII; lane 6, PCR-amplified nuclease gene fragment from pFOG 408 using L-SNUS and R-SNUC primers.

The transformed cells were initially selected on LB agar plates containing 40 μg per ml ampicillin. Two putative clones which showed indicator colour change on DNAse test agar plate, were further tested on LB agar containing ampicillin, $CaCl_2$, $MgCl_2$, and IPTG. *E. coli* JM109 containing pSNUC-1 showed no growth on agar plate containing IPTG even after incubation up to 72 hours (FIG. 11). In contrast to this, *E. coli* JM109 carrying pSNUC-3 showed inhibited growth on similar type of agar plate containing IPTG (FIG. 12). In both cases, the control LB agar plates containing $CaCl_2$ and $MgCl_2$, but no IPTG showed complete growth within an 18–24 hours' time period. In this experiment, the inoculum sizes were kept as equal as possible for both types of plates, and they showed consistent results every time when repeated for a total of 7 times. Restriction analysis of the plasmids pSNUC-1 and pSNUC-3 with HindIII produced expected DNA bands of approximately 0.219 kb and 4.0 kb bands (FIG. 13). Since there was one HindIII restriction site within the coding sequence of the nuclease gene and one on the vector, it was possible to determine the right orientation of the nuclease gene on the vector.

Nucleotide sequence analysis of the first 40 bases of the cloned fragments in both pSNUC-1 and pSNUC-3 plasmids at their 5'-ends confirmed the presence of the nuclease gene in the right orientation.

D. Induction of pSNUC-1 and pSNUC-3

The *E. coli* JM109 (pSNUC-1) and *E. coli* JM109 (pSNUC-3) were grown in LB broth containing 10 mM $CaCl_2$ and 1 mM $MgCl_2$ at 37° C. for 1 hour with shaking at 100 rpm till the optical density ($OD_{450}$) reached 0.5–0.7 when 1 mM sterile IPTG solution was added for induction. Before and after the addition of IPTG the $OD_{450}$ was recorded every hour, a fraction of the cultures was serially diluted in phosphate buffer (pH 7.2) and plated on LB agar plates with 10 mM $CaCl_2$ and 1 mM $MgCl_2$ to determine viable plate counts. A control culture of each of the plasmid constructs was kept to compare the expression and killing efficiencies of the nuclease gene.

E. Expression of the Cloned Nuclease Gene Following Induction *E. coli* JM109 (pSNUC-1) and *E. coli* JM109 (pSNUC-3) were grown in LB broth as described earlier to mid-exponential phase ($OD_{450}$ Of 0.4 to 0.5) and IPTG was added for induction. The induction was carried on for 20 min when the cells were centrifuged and prepared for the total protein analysis by SDS-PAGE as described by Ausubel et al (1987) using the Mini-Protean II gel system (BioRad). The PAGE separated proteins were stained with commassie blue. Uninduced cultures of *E. coli* JM108 (pSNUC-1) and (pSNUC-3), cultures of *E. coli* AR120 (pFOG408), and *E. coli* JM109 (pUHE24-2) were used for controls.

For further characterization of the cloned nuclease genes in pSNUC-1 and pSNUC-3, a western blot was performed using rabbit antibody (a gift from A. Meeker). The proteins from the PAGE were transferred to nitrocellulose membrane (Millipore) using the Mini-Trans Blot system (BioRad). A 1:15,000 dilution of rabbit antibody was used and detected with biotinylated goat antirabbit immunoglobulin and streptavidin peroxidase (Fisher Biotech). The color development was performed by incubating in the peroxidase substrate by 4-chloro-1-naphthol. Appropriate controls were tested in this experiment.

Figure 14A:
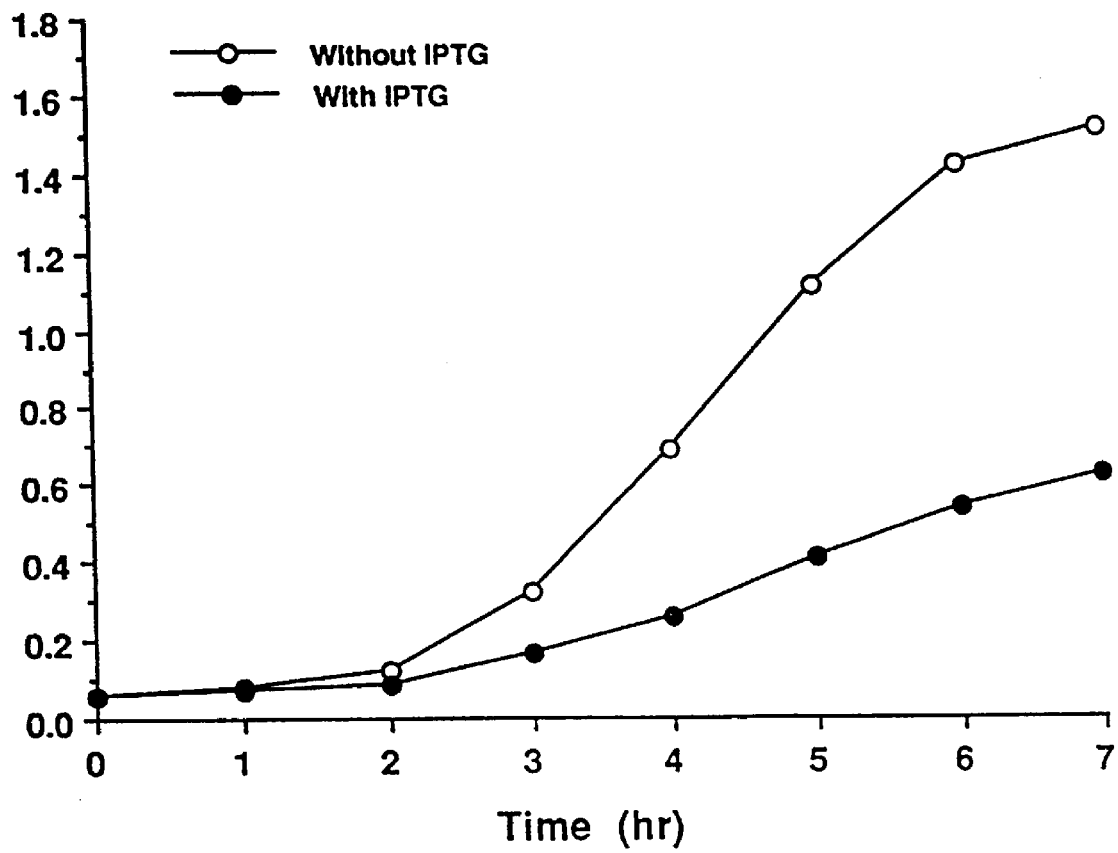
FIG. 14A shows the kinetics of induction of E. coli JM109 (pSNUC-1) in liquid culture with and without IPTG ($OD_{450}$)
Figure 14B:
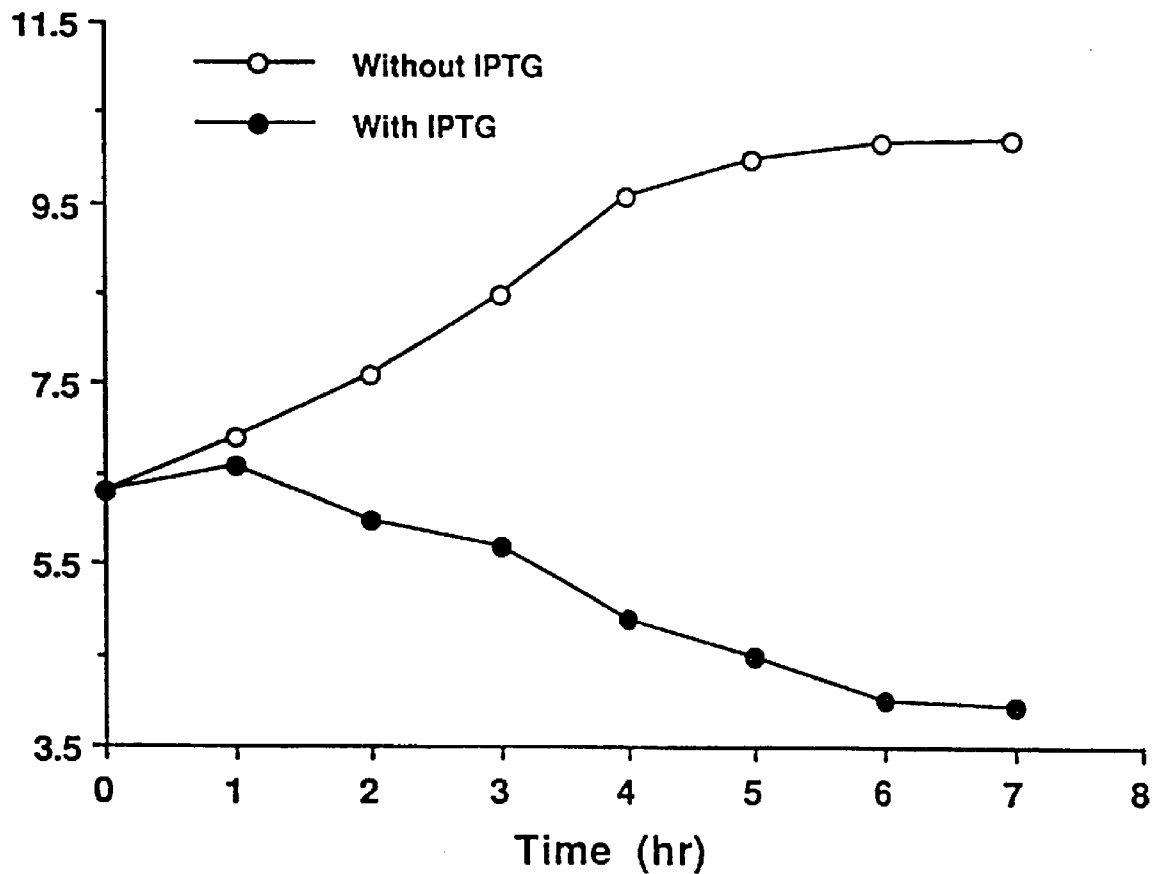
FIG. 14B shows log viable plate counts of E. coli JM109 (pSNUC-1) with or without IPTG.
Figure 15A:
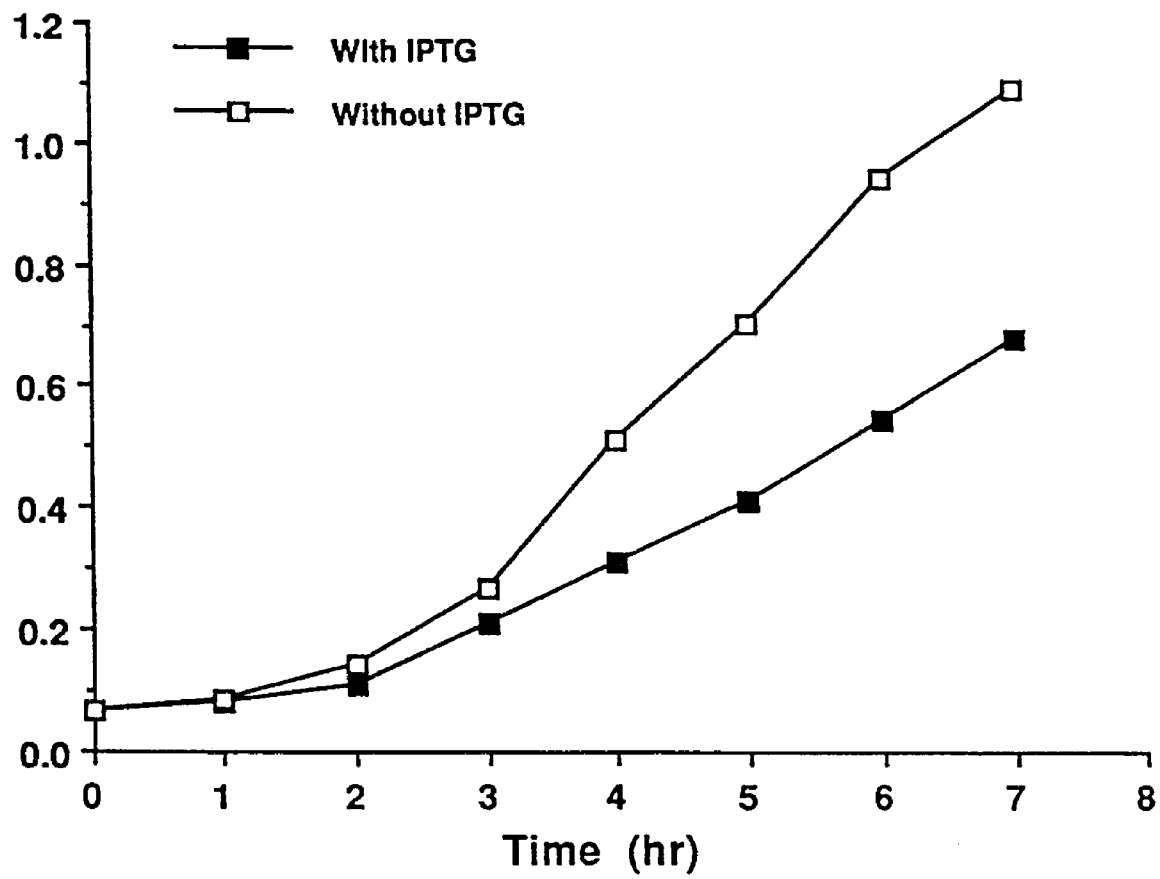
FIG. 15A shows kinetics of induction of E. coli JM109 (pSNUC-3) in liquid culture with and without IPTG ($OD_{450}$)
Figure 15B:
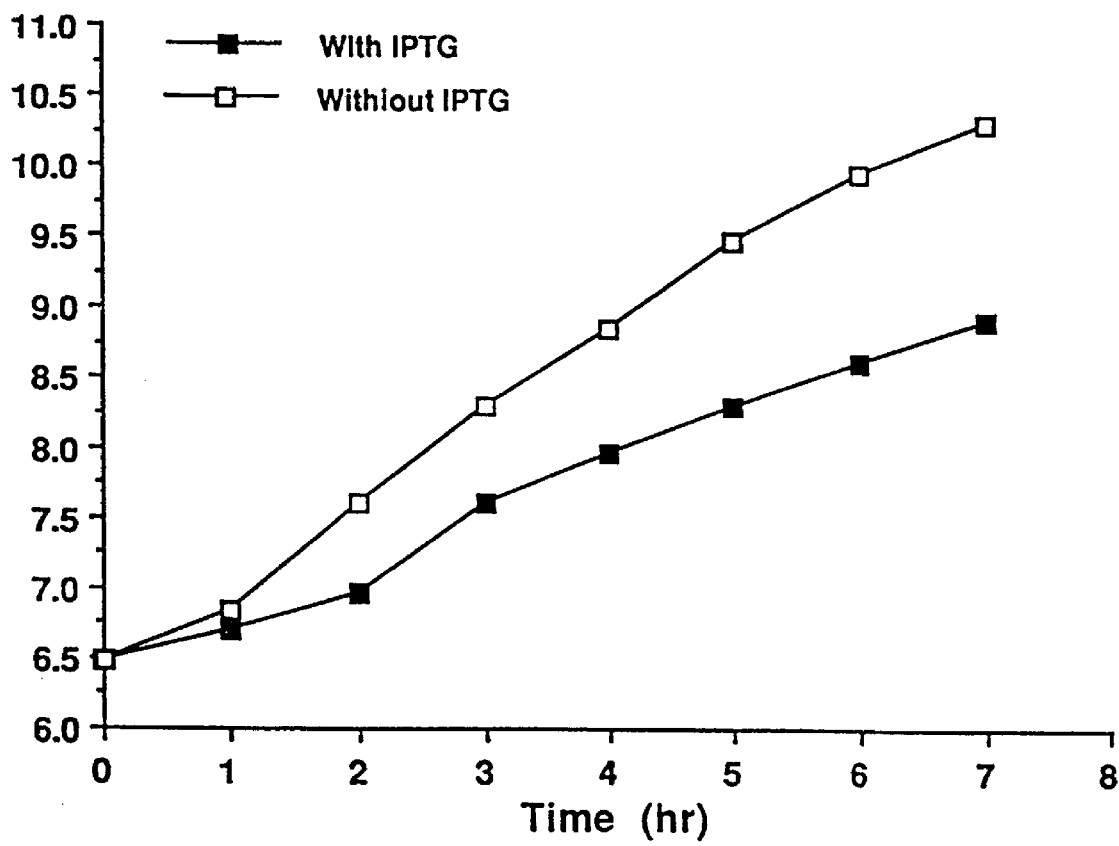
FIG. 15B shows log viable plate counts of E. coli JM109 (pSNUC-3) with or without IPTG.

Induction of *E. coli* JM109 (pSNUC-1) with IPTG showed significant decline in cell numbers between 2–7 hours' time period as determined by the $OD_{450}$ reading and viable plate counts (FIGS. 14a and 14b). The total cell number for *E. coli* JM109 (pSNUC-1) per ml declined form $2 \times 10^6$ to $1.5 \times 10^4$ between 0–7 hours' time period as determined by viable plate counts. In contrast to this, when *E. coli* JM109 (pSNUC-3) was induced with IPTG, a slow increase in cell number was evidenced as compared to the uninduced control as determined by the $OD_{450}$ measurements and viable plate counts (FIGS. 15a and 15b). The total cell number increased form $3 \times 10^6$ to $7 \times 10^8$ per ml between 0–7 hours as compared to the uninduced control which was $3 \times 10^6$ to $2 \times 10^{10}$ within the same time period. From these results it can be predicted that the lower killing efficiency of the plasmid pSNUC-3 upon induction as compared to pSNUC-1 may be due to mutation generated by misincorporation of nucleotide(s) during the PCR DNA amplification process. However, it is not obvious which of the two clones, if not both, has the altered nucleotide sequence.

The phenotypic expression of the cloned nuclease genes in pSNUC-1 and pSNUC-3 plasmids on the DNAse test agar containing methyl green indicator dye showed expected color change. The pSNUC-1 showed more rapid color change than pSNUC-3. The control plasmid vector pSM1128 did not show any change in color on the same agar plates, whereas, plasmid pFOG408 showed significant color change.

Figure 16:
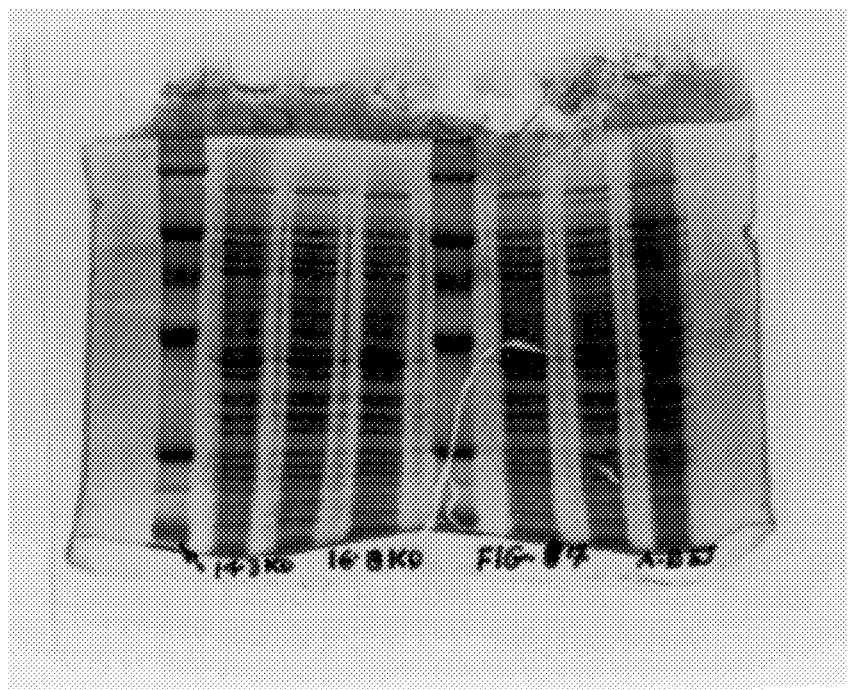
FIG. 16 shows SDS-PAGE analysis of whole cell protein extract from E. coli JM109 (pSNUC-1) and E. coli JM109 (pSNUC-3) cultures with or without IPTG. The gel was stained with commassie blue. Total cellular protein from E. coli AR120 (pFOF408) was used as a positive control and E. coli (pUHE24-2) was used as a negative control. The nuclease bands are indicated with arrows. Lane 1, protein size standard; lane 2, pSNUC-1 without IPTG; lane 3, pSNUC-1 with IPTG; lane 4, pSNUC-3 without IPTG; lane 5, protein size standard; lane 6, pSNUC-3 with IPTG; lane 7, pFOG408 as positive control; lane 8, pUHE24-2 as negative control.
Figure 17:
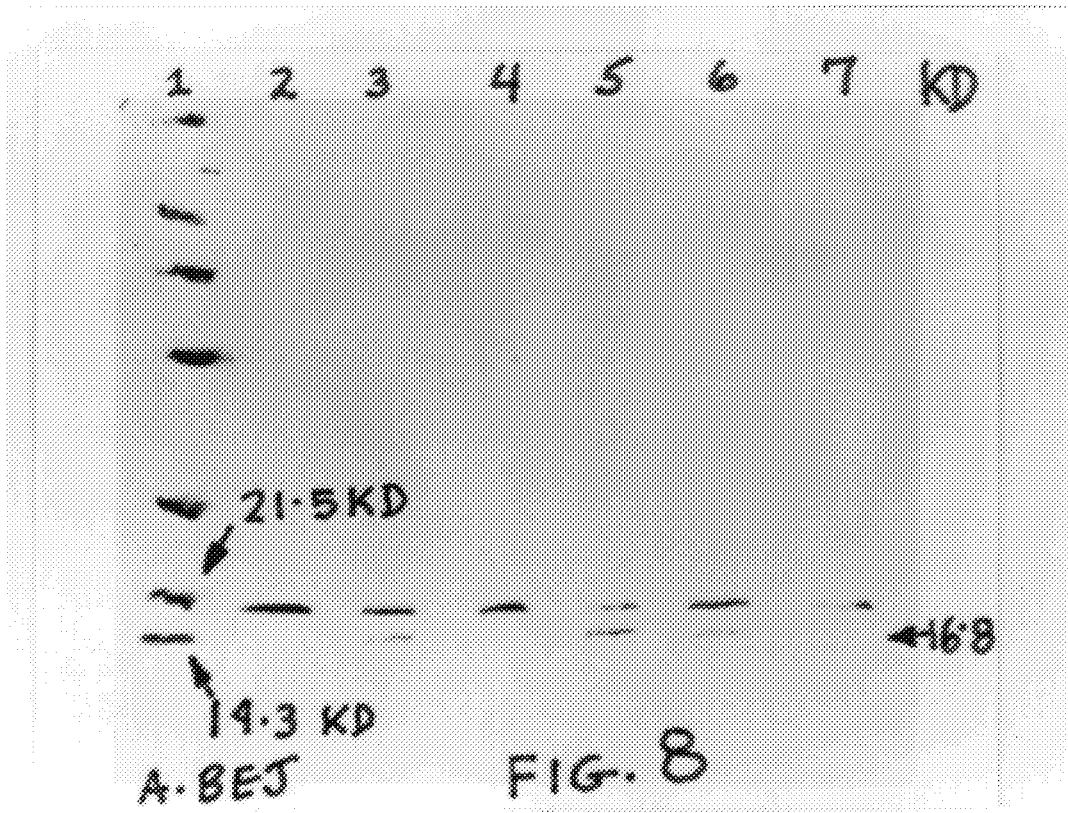
FIG. 17 shows a Western blot analysis of cellular proteins from cultures of E. coli JM109 (pSNUC-1) and E. coli JM109 (pSNUC-3) with or without IPTG. E. coli AR120 (pFOF408) was used as a positive control and E. coli JM109 (pUHE24-2) was used as a negative control. The 17.8 kD nuclease protein bands are indicated with arrows. Lane 1, protein size standard; lane 2, pSNUC-1 without IPTG; lane 3, pSNUC-1 with IPTG; lane 4, pSNUC-3 without IPTG; lane 5, pSNUC-3 with IPTG; lane 6, pFOG408 as positive control; lane 7, pUHE24-2 as negative control.

The PAGE gel for total protein analysis showed faint bands of approximately 17.8 kD size range for plasmids pSNUC-1 and pSNUC-3 following induction with IPTG. The uninduced controls and pUHE24-2 did not show any such band (FIG. 16). Since nuclease is an extracellular secretory protein, the *E. coli* strain carrying pFOG408 plasmid showed a very faint band in the gel. To confirm the expression of the cloned nuclease gene in plasmids pSNUC-1 and pSNUC-3, a western blot was performed. In the western blot, distinct protein bands of approximately 17.8 kD were evidenced from the induced *E. coli* JM109 strains carrying pSNUC-1 and pSNUC-3 plasmids, and *E. coli* AR120 strain carrying pFOG408 plasmid (FIG. 17). The uninduced cultures and control plasmid pSM1128 did not show any band. Another non-specific band of approximately 20 kD size was noticed in all samples, which seems to be the non-specific antigenic reaction against the secondary antibody. This experiment suggested that the nuclease was produced by both plasmids pSNUC-1 and pSNUC-3 upon induction. The lower killing efficiency for the pSNUC-3 plasmid could be due to the altered nucleotide sequence which has changed the protein structure and its functions for the substrate. Alternatively, this could be the case for the plasmid pSNUC-1 for its relatively higher killing efficiency. Complete nucleotide sequence analysis for both clones may resolve this question and also provide the information on possible sites where change of nucleotide sequence may make this enzyme more effective.

EXAMPLE 14

Determination of Intracellular Stability of Cloned Stanhylococcal Nuclease in *Escherichia coli* by ELISA Assay The staphylococcal nuclease gene snuc without its signal sequence was PCR-amplified and cloned in *Escherichia coli* JM109 as described in Example 13 using the expression vector pUHE24-2, in the BamHI restriction site (pSNUC-1 and pSNUC-3). The nuclease was expressed intracellularly when induced with IPTG. The stability of the intracellularly expressed SNUC enzyme in *E. coli* following induction was determined by ELISA assay using antibodies raised in rabbits. Two approaches were pursued to determine the stability of the intracellularly expressed SNUC enzyme:

1. Transcriptional inhibition following induction by blocking mRNA synthesis with rifampicin.
2. Removal of inducing agent (IPTG) from the culture following induction.

1. Transcriptional Inhibition Following Induction by Blocking mRNA Synthesis with Rifampicin E. coli cells harbouring pSNUC-1 or pSNUC-3 were grown in liquid broth at 37° C. till the optical density ($OD_{450}$) was between 0.12 and 0.15 (early exponential growth phase). The cells were then induced with IPTG for 30 minutes, and rifampicin was added to the culture to block transcription. The incubation was carried on for the next 3 hours. E. coli JM109 without pSNUC-1 or pSNUC-3 was used as the control.

Aliquots of 1 ml of the cultures were collected before induction, 30 minutes after induction, and every 30 minutes after the addition of rifampicin. The cells were centrifuged, washed twice with phosphate buffer (pH 7.2), and disrupted by sonication to release the total cellular proteins. The sonication was carried on (8 to 10 minutes with a pulse for 30 seconds at every 30 seconds interval) till the sample became clear. The debris was spun down and the supernatant (lysate) was used for ELISA assay.

An aliquot of each of the samples was subjected to spectrophotometric measurement to determine the total protein concentration. ELISA assay was performed using equal quantity of total cellular protein from each lysate. Typically, 10 to 55 µl of lysates (depending on the concentration of each lysate) from various samples were absorbed in a microtiter plate (Corning) for about 16 hours (overnight) at 4° C. The wells were then washed 5 times with phosphate buffer (pH 7.2). The unreacted surface of the microtiter plate was blocked with 2% bovine serum albumin (BSA) from Sigma Chemical at room temperature for 1 hour with gentle shaking. The excess BSA from the microtiter plate was washed off 5 times with phosphate buffer (pH 7.2). 1:15.000 fold diluted polyclonal primary antibodies raised against the purified extracellular staphylococcal nuclease in rabbits, was reacted with preabsorbed total cellular proteins for about 16 hours (overnight) at 4° C. The unreacted primary antibodies were washed off 5 times with phosphate buffer (pH 7.2).

The bound primary antibodies were then treated with secondary antibodies, goat antirabbit-Ig-biotin (CloneTech) for 1 hour at room temperature with gentle shaking. After washing off excess secondary antibodies, streptavidin-horseradish peroxidase (HRP-SA) conjugate was added to the microtiter plate and conjugated with the secondary antibodies. After washing off excess HRP-SA, colour development was carried out using 0.1 ml of substrate [2,2'-azinobis (3-ethyl benzthiazoline sulphonic acid) in a 0.1M citrate buffer, pH 4.2 with 0.03w hydrogen peroxide]. The absorbance was read at 415 nm in an ELISA microtiter plate reader (Flow Laboratories, Inc., McClean, Va.).

2. Removal of Inducible Agent (IPTG) from the Culture Following a Short Induction Stage E. coli cells harbouring pSNUC-1 or pSNUC-3 were grown to early exponential phase ($OD_{450}$ of 0.12 to 0.15) when 1 mM IPTG (final concentration) was added to the culture. The induction with IPTG was carried on for 5 minutes at 37° C. and the cells were centrifuged and washed twice with phosphate buffer (pH 7.2). The cells were resuspended in broth and incubated at 37° C. for another 3 hours. Aliquots of 1 ml each of the cultures were collected before induction and 5 minutes after induction. Also, aliquots were collected by centrifugation, washed twice with phosphate buffer (pH 7.2) and sonicated to release total cellular proteins. Cultures of E. coli JM109 without pSNUC-1 or pSNUC-3 was used as the negative control.

Total cellular proteins were released by disrupting the cells using a sonic disrupter as described above. ELISA assays for intracellularly expressed staphylococcal nuclease was also performed as described above.

The amount of staphylococcal nuclease protein encoded by pSNUC-1 and pSNUC-3 after transcriptional inhibition as defined above, was found to be significant amounts following induction with IPTG. The data for pSNUC-1 and pSNUC-3 are summarized in Tables 5 and 6, respectively. The expression of staphylococcal nuclease increased about 2-fold during the first 30 minutes after induction as compared with the amount detected prior to induction. The activity of the nuclease enzyme remained during the first 2 hours following rifampicin treatment. Between 2 and 3 hours after addition of rifampicin (2.5 and 3.5 hours after induction with IPTG; the activity of the nuclease was dropped significantly. From this experiment it can be concluded that the staphylococcal nuclease is stable intracellularly for at least 1.5 hours after the inhibition of transcription.

TABLE 5

Determination of the stability of intracellularly expressed staphylococcal nuclease expressed by pSNUC-1 following induction with IPTG and treatment with rifampicin

| Treatment | Time (h) | ELISA readings |
|---|---|---|
| IPTG | 0 | 0.427 |
| Rifampicin | 0.5 | 0.584 |
| | 1.0 | 0.666 |
| | 1.5 | 0.685 |
| | 2.0 | 0.675 |
| | 2.5 | 0.542 |
| | 3.0 | 0.488 |
| | 3.5 | 0.407 |
| Negative control | 1.0 | 0.276 |

TABLE 6

Determination of the stability of intracellularly expressed staphylococcal nuclease expressed by pSNUC-3 following induction with IPTG and treatment with rifampicin

| Treatment | Time (h) | ELISA readings |
|---|---|---|
| IPTG | 0 | 0.399 |
| Rifampicin | 0.5 | 0.495 |
| | 1.0 | 0.557 |
| | 1.5 | 0.593 |
| | 2.0 | 0.555 |
| | 2.5 | 0.443 |
| | 3.0 | 0.427 |
| | 3.5 | 0.378 |
| Negative control | 1.0 | 0.258 |

After induction of with IPTG for a short period of time (5 minutes), the cells were centrifuged, washed with phosphate buffer (pH 7.2), and grown in a rich medium for 150 minutes to determine the stability of the SNUC in the cells.

The summary of the data is presented in Tables 7 and 8. There was at least 3-fold increase in the amount of SNUC following induction. The SNUC protein was found to be stable in pSNUC-1 for 1.5 and 2 hours (between 5 and 125 minutes) after induction and 1 to 1.5 hours (between 5 and 95 minutes) in pSNUC-3 as it was determined by the ELISA assay. After 125 minutes for pSNUC-1 and 95 minutes for pSNUC-3 following removal of the inducing agent (IPTG), the SNUC activity decreased significantly.

TABLE 7

Determination of the stability of intracellularly expressed staphylococcal nuclease expressed by pSNUC-1 following removal of IPTG after 5 minutes of induction

| Treatment | Time (min) | ELISA readings |
|---|---|---|
| IPTG | 0 | 0.270 |
| Removal of IPTG | 5 | 0.565 |
|  | 35 | 0.560 |
|  | 65 | 0.543 |
|  | 95 | 0.501 |
|  | 125 | 0.456 |
|  | 155 | 0.329 |
| Negative control | 35 | 0.204 |

Table 8

Determination of the stability of intracellularly expressed staphylococcal nuclease expressed by pSNUC-3 following removal of IPTG after 5 minutes of induction

| Treatment | Time (min) | ELISA readings |
|---|---|---|
| IPTG | 0 | 0.171 |
| Removal of IPTG | 5 | 0.461 |
|  | 35 | 0.458 |
|  | 65 | 0.430 |
|  | 95 | 0.375 |
|  | 125 | 0.269 |
|  | 155 | 0.210 |
| Negative control | 35 | 0.164 |

EXAMPLE 15

Construction and Testing of a Model Inducible Containment System Based on the Expression of an Intracellularly Active Phospholipase Model plasmids for evaluation of an inducible cell function limiting function based on a toxic hydrolytically active enzyme was constructed and tested in *Escherichia coli*. The active component of the system is an extracellular phospholipase obtained from the strain Serratia lilzefaciens and encoded by the gene phlA. The plasmids are based on the vector pMG300 (Givskov and Molin 1988, J.Bacteriol 170, 5855–5862), a derivative of pCH624 (Boros 1984 Gene, 30, 257–260). pMG300 (FIG. 18) carries the temperature inducible repressor promoter cI857/pR of the lambda phage. The phlA gene is inserted downstream from this promoter and induction of phlA can be achieved by rising the temperature in the growth medium from 30° C. to 41° C. Induction results in cell death. The plasmids confer resistance to ampicillin. The phlA gene is inserted downstream from the lacI$^q$/ptac repressor/promoter system of the broad host range plasmid pVLT33. This plasmid can be transferred by conjugation to gram-negative bacteria.

A. Construction of the Model Plasmids pMG323 and pMG317

Figure 18:
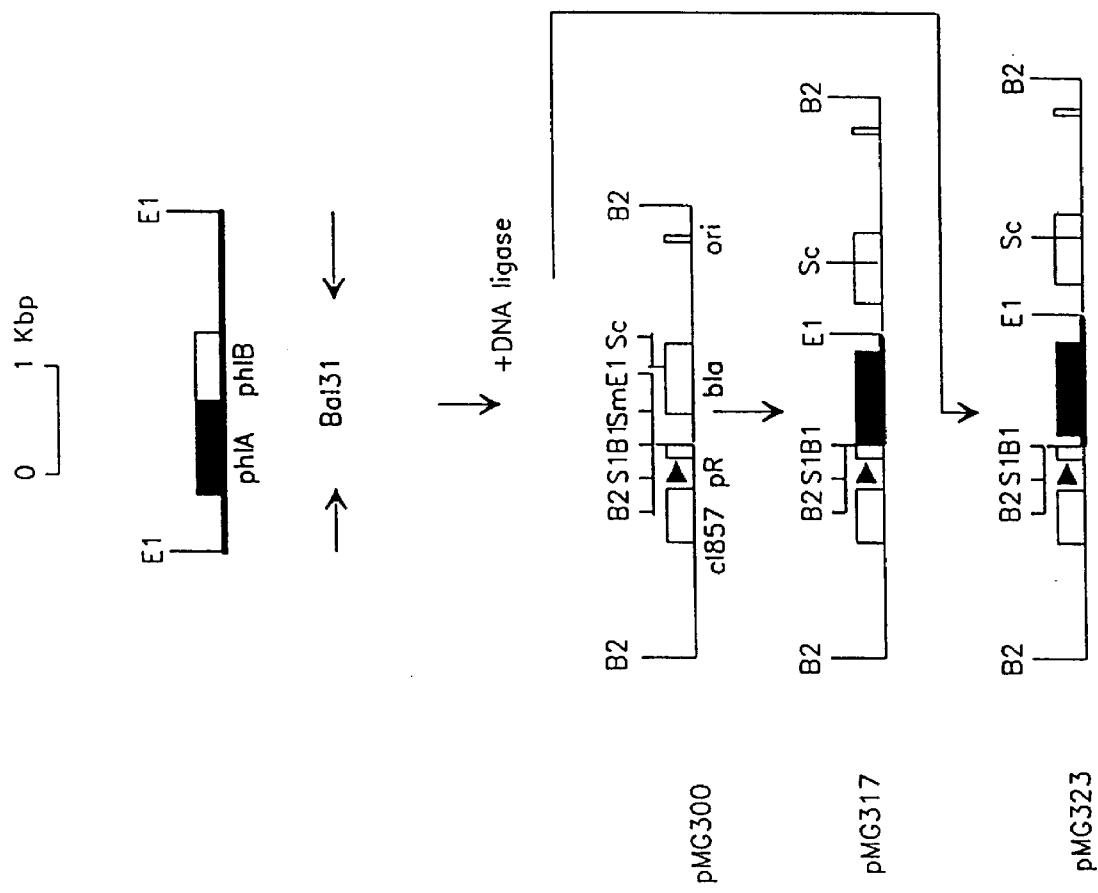
FIG. 18 shows a schematic representation of the construction of plasmid pMG323.
Figure 19:
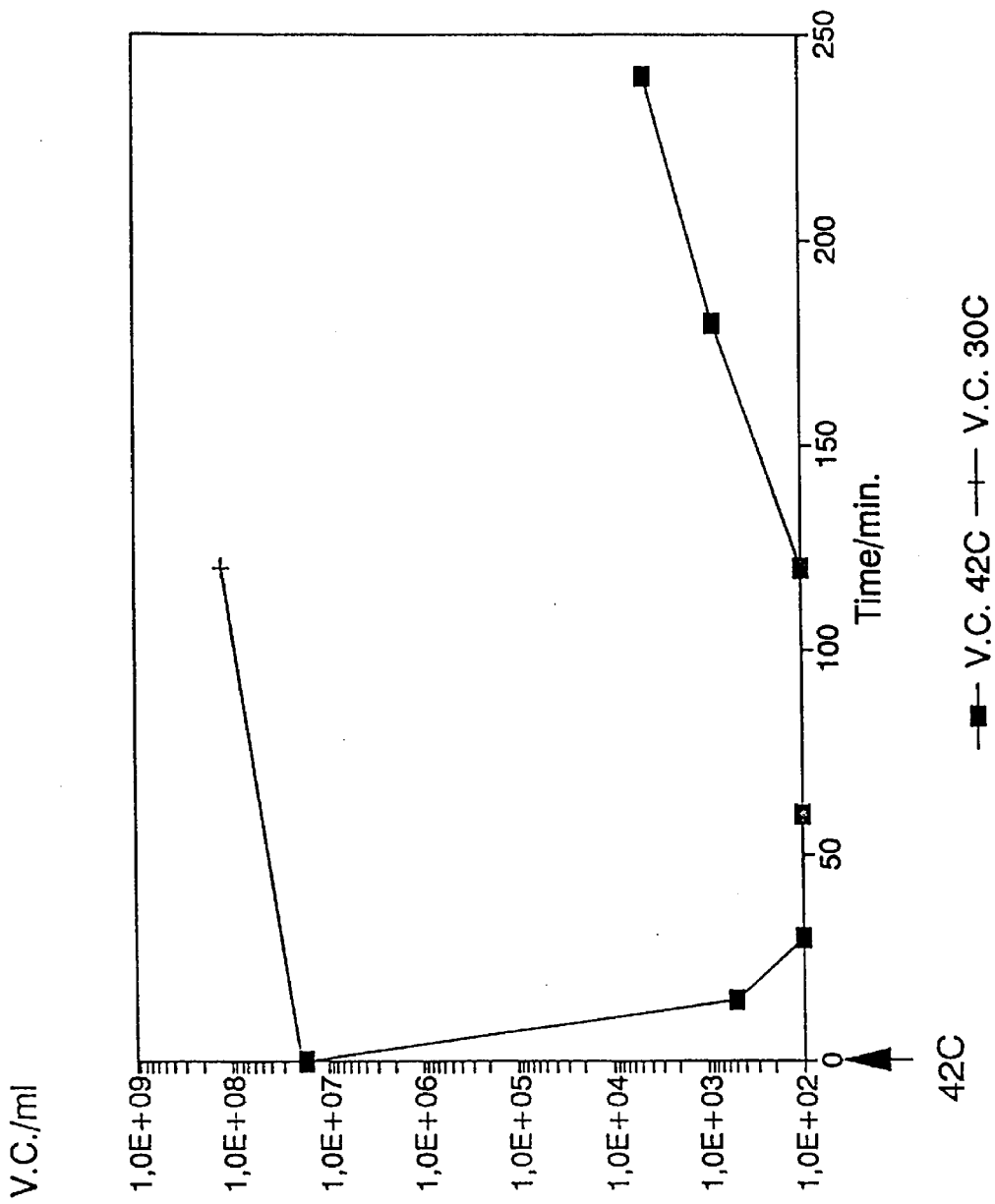
FIG. 19 shows viable counts (V.C.) of E. coli CSH50 transformed with pMG317 grown in LB medium supplemented with 100 µg/ml of ampicillin under phlA inducing conditions (41° C.) and non-inducing conditions (37° C.)

The construction of plasmid pMG300 was described by Givskov and Molin 1988, J.Bacteriol 170, 5855–5862. The gene phlA encoding the toxic hydrolytic phospholipase was obtained from a genomic bank of *Serratia liquefaciens*, constructed on the vector pNU121 (Nielsson et al. 1983, Nucl. Acid Res. 11, 8019–8030). A 3200 base pair EcoRI restriction fragment carrying the phospholipase operon genes phlA and phlB was purified and digested in-vitro with the exonuclease Bal3l. Digested DNA was ligated into the SmaI restriction site of pMG300. *E. coli* clones, where expression of phospholipase was controlled by the temperature inducible promoter system, were isolated. Two plasmids, pMG317 and pMG323 were obtained by this procedure (FIG. 18). These two plasmids and the DNA-sequence of the phospholipase operon has been described by Givskov and Molin 1988, J.Bacteriol 170, 5855–5862. *E. coli* strain CSH50 harbouring plasmid pMG317 was grown in 50 ml LB medium supplemented with 100 μg/ml ampicillin and 0.2% glucose, at a temperature of 30° C. in a shaking 300 ml Erlenmeyer flask. At an $OD_{450}$ of 0.2 the culture was diluted to an $OD_{450}$ of 0.05 and growth continued to obtain an $OD_{450}$ of 0.2. The culture was divided into two, of which one continued growth at 30° C. whereas the other one was shifted to a growth temperature of 41° C. Samples of the cultures were taken at different times after the temperature shift, diluted in 0.9% NaCl and plated on LB agar plates supplemented with 100 μg/ml ampicillin. The viable count of the cultures were determined by counting the number of colonies (CFU/ml) on the LB plates after an overnight incubation at 30° C. The proportion of Phl+cells in the culture was determined by replica plating to phospholipase indicative plates, viz. plates with LB agar supplemented with 1% egg-yolk and 100 μg/ml ampicillin and incubating the plates overnight at 30° C. followed by two hours incubation at 41° C. (FIG. 19).

The results of the experiment is summarized in the below table:

TABLE 9

Growth and survival of CSH50 transformed with pMG317 under phlA inducing conditions (41° C.) and non-inducing conditions (30° C.)

| time/min | $OD_{450}$ | CFU/ml | % Phl+ |
|---|---|---|---|
| 41° C. culture: | | | |
| 0 | 0.450 | $1.8 \times 10^7$ | 100 |
| 15 | 0.530 | 500 | 70 |
| 30 | 0.280 | <100 | 2 |
| 60 | 0.180 | <100 | 1 |
| 120 | 0.145 | <100 | 0 |
| 180 | 0.160 | 800 | 0 |
| 240 | 0.160 | $4.3 \times 10^3$ | 0 |

Killing effect after 15 minutes: $4 \times 10^4$, killing effect after 30 minutes: $>2 \times 10^5$.

| 30° C. culture: | | | |
|---|---|---|---|
| 0 | 0.450 | $1.8 \times 10^7$ | 100 |
| 120 | 3.00 | $1.2 \times 10^8$ | 100 |

The above results are also illustrated in FIG. 19.

B. Construction of Model Plasmid pMG323/33

Figure 20:
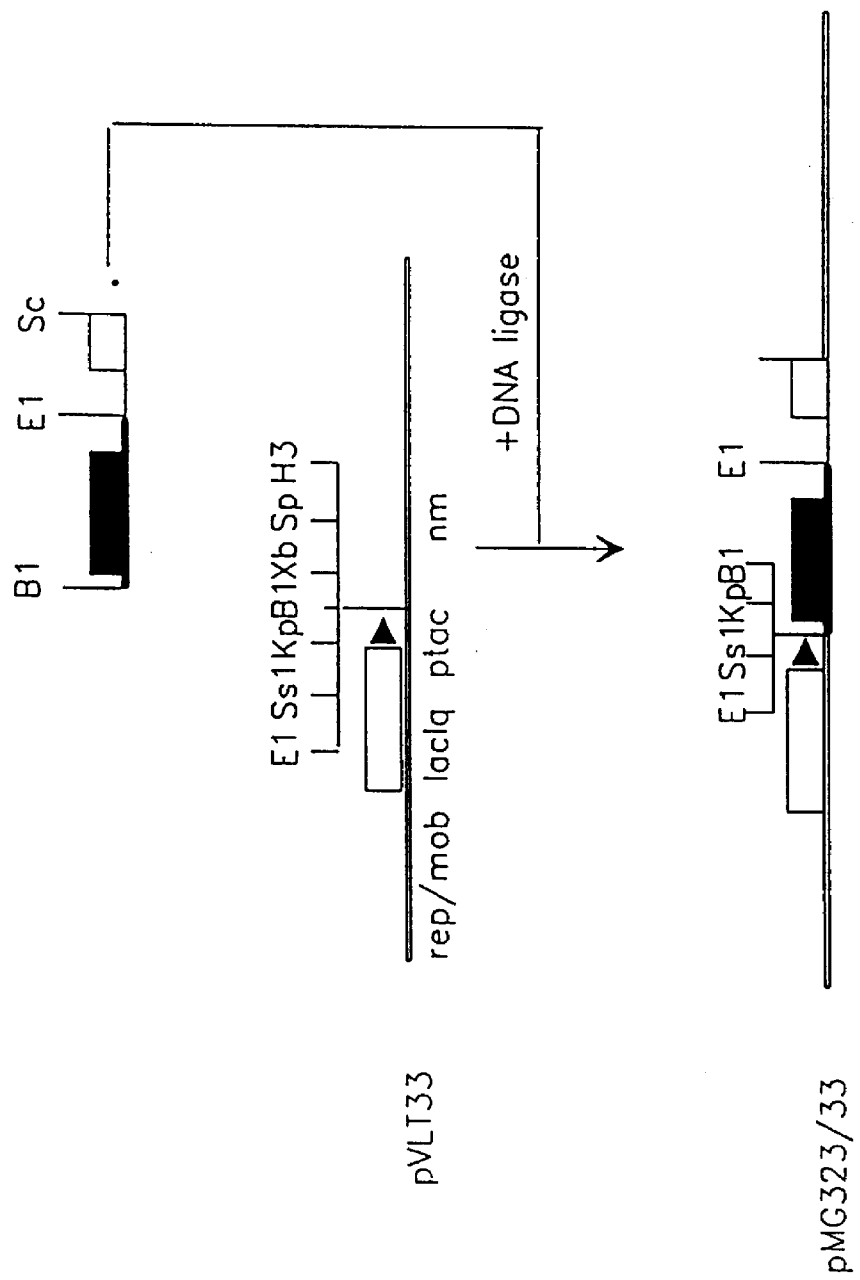
FIG. 20 shows the construction of the plasmids pMG317, pMG323 and pMG323/33. Enzyme abbreviations: B1 BamHI, B2 BglII, E1 EcoRI, H3 HindIII, Kp KpnI, Sm SmaI, Sc ScaI, Sp SphI, Ss SstI. Genes: bla and nm encoding resistance to ampicillin and kanamycin, respectively, ori replication origin, rep replication functions, mob conjugative transfer, CI857 temperature sensitive lambda repressor, pR lambda promoter region, laciq lactose repressor, ptac tac promoter. Heavy line is Serratia DNA.

Plasmid pMG323 was digested with BamHI and ScaI. PVLT33 was digested with HindIII treated with Klenow polymerase to create blunt ends, digested with BamHI and l gated to purified BamHI-ScaI restriction fragment obtained from pMG323 giving rise to plasmid pMG323/33 (FIG. 20) where PhlA production is inducible by addition of IPTG. The plasmid confer resistance to kanamycin and can be transferred to other bacteria by conjugation.

EXAMPLE 16

Figure 21:
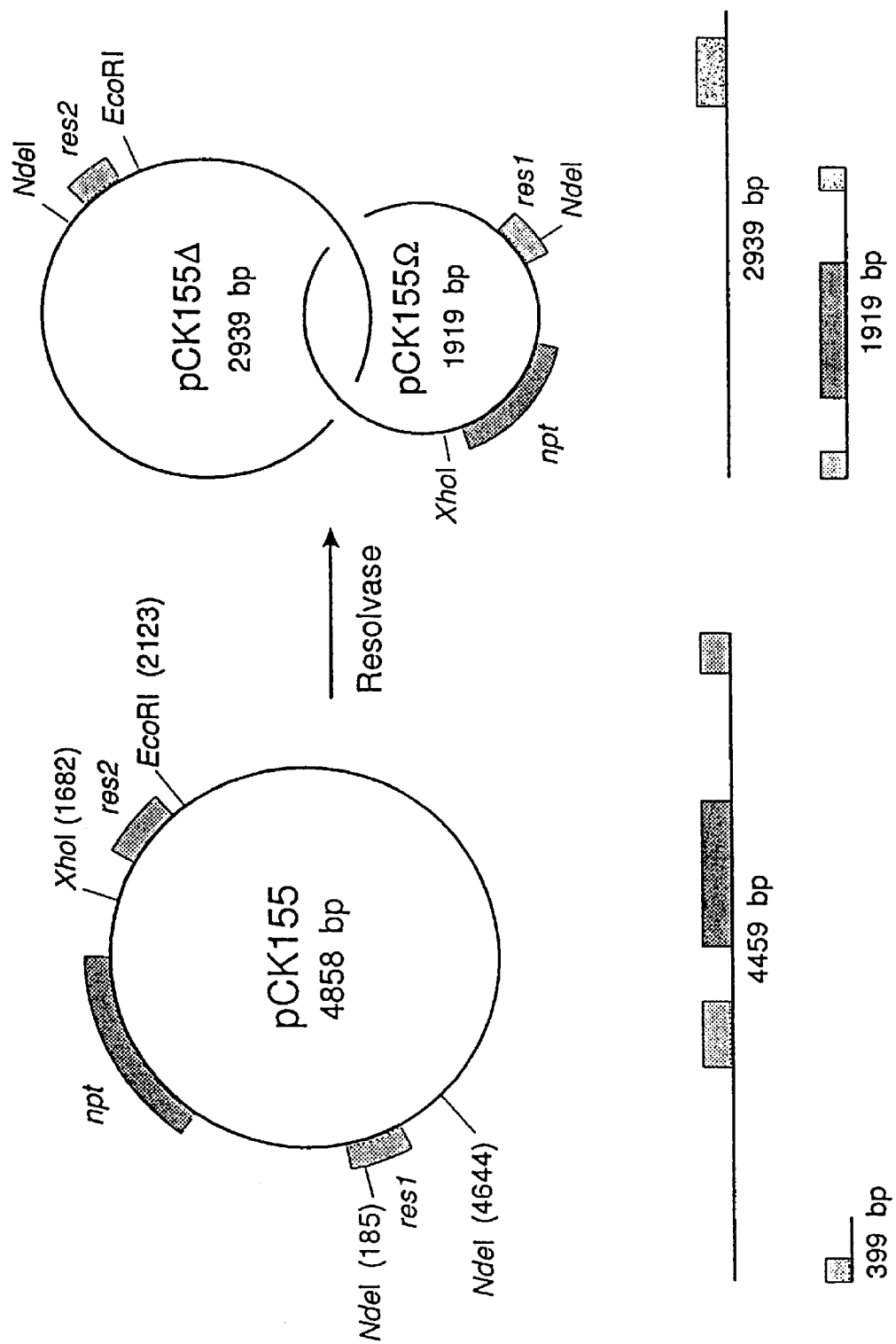
FIG. 21 shows a schematic representation of the resolvase-mediated recombination reaction. Plasmid pCK155 was converted to two other species, pCK155delta and pCK15omega. The resulting fragments resulting from cutting with restriction enzyme NdeI are shown for each of the plasmid configurations.

Construction of Plasmids for Site-Specific Recombination Mediated Stochastically Regulated Induction of Genes The resolution system of the broad-host range plasmid RP4 is essential for multimer resolution of the plasmid during replication (Grinter et al. 1989, Plasmid, 22, 203–214). The involved components, the resolvase gene (parA) and the site for this site-specific resolution (mrs) have been cloned previously (Gerlitz et al. 1990, J.Bacteriol. 172, 6194–6203; Roberts et al., 1990, J.Bacteriol. 172, 6204–6216). If two mrs sites are placed in direct orientation, the intervening sequence can be deleted with a high frequency by supplying the parA in trans (Roberts et al. supra. The reaction is outlined in FIG. 21.

A. A Model System for Testing the Resolvase Mediated Recombination

A plasmid containing two directly oriented mrs sites was constructed on the basis of pCK46 and pCK30 described in Example 9. pMRS19A (Eberl et al., 1992a, Molec. Microbiol., in press) was linearized with NdeI and filled in with the large subunit of DNA polymerase I (Klenow fragment). This blunt ended fragment was subsequently cut with SalI and the smaller fragment, containing the mrs site was ligated to pCK46 cut with SmaI and SalI, resulting in pCK145.

pMRS19A was cut with BamHI and SphI. The small fragment was inserted into pCK30 digested with BglII and SphI, giving pCK146. A plasmid, pSM891, containing the transposon Tn5 was digested with HindIII and SmaI and the about 1100 base pair fragment containing the kanamycin (npt) gene was blunt ended as described. This fragment was inserted into pCK146, opened in SmaI. The resulting plasmids were named pCK153 and pCK154. pCK153 has the recreated SmaI site proximal to the XhoI site. In pCK154 the Tn5 fragment is inverted. pCK155 (cf. FIG. 22) was created by inserting the approximately 1500 base pair XhoI-HindIII fragment of pCK153 into pCK145, linearized with XhoI and HindIII.

Figure 22:
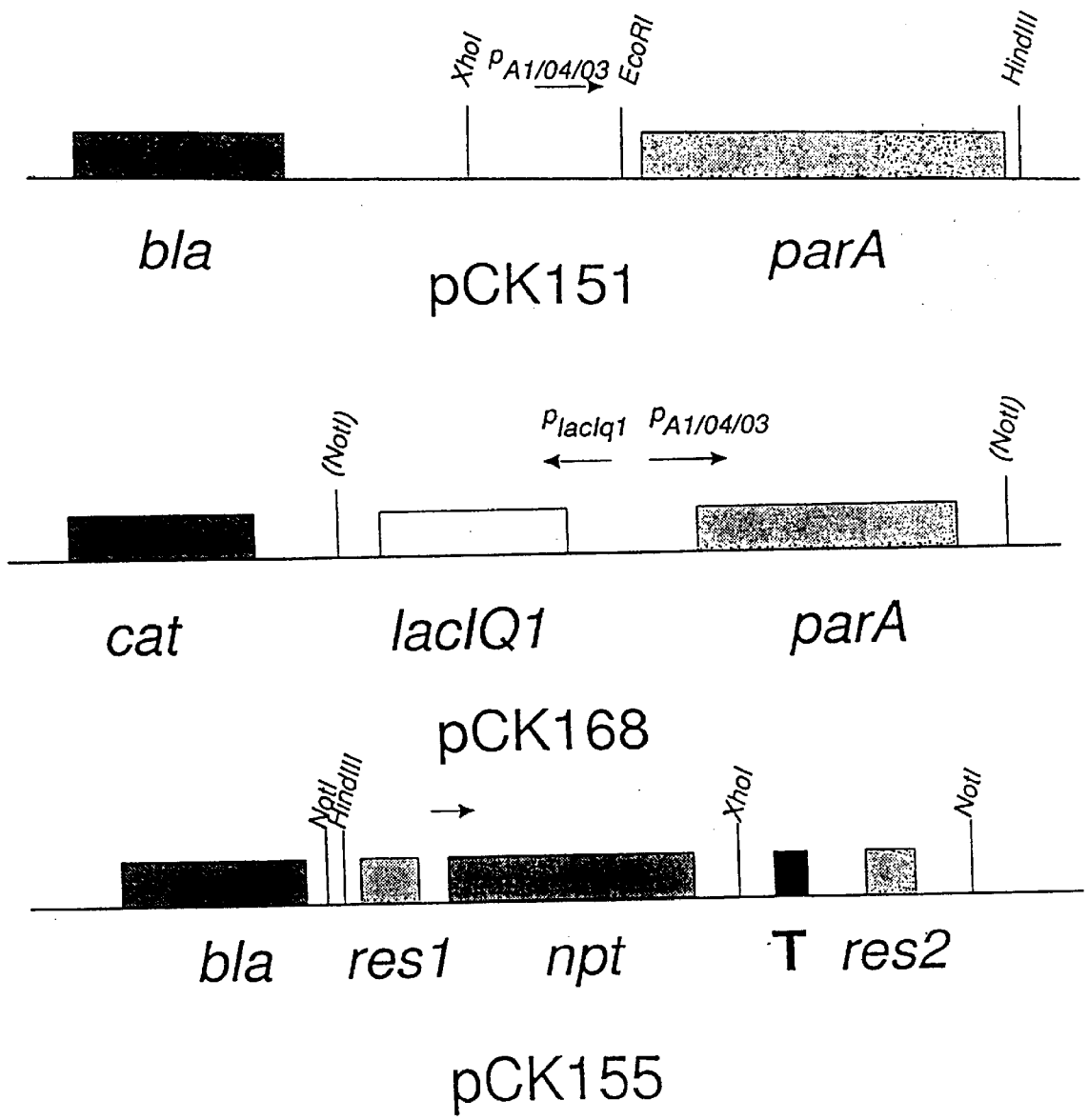
FIG. 22 shows an overview of the plasmids pCK151, pCK155 and pCK168. Unique restriction sites are shown. Restriction sites in parentheses indicate filled-in (non-functional) sites. The abbreviation T indicates the rpoCt' terminator. Plasmids pCK151 and pCK155 have a replicon derived from pUC18, whereas pCK168 is derived from pACYC184.

The resolvase was cloned from pGMA70 (Eberl et al., 1992b, manuscript in preparation). The promoterless parA from pGMA70 was excised as an approximately 1100 base pair EcoRI-HindIII fragment and inserted into the EcoRI-HindIII cut pUHE24-1 (Lanzer et al., 1988, Proc. Natl. Acad. Sci. USA 85, 8973–8977), resulting in pCK151 (FIG. 22). This plasmid contains the parA under the control of the synthetic lac-promoter pA1/04/03. The resolvase expression can be repressed by the lac repressor, lacI, and be induced by adding IPTG (isopropyl-β-D-thiogalactoside) to a culture containing the plasmid. This plasmid is used for overexpression of the resolvase protein for purifying purposes.

The parA gene was likewise moved to pLBJ65 (Bogo Jensen et al., 1992, manuscript in preparation) as the EcoRI-HindIII fragment described above. The resulting plasmid, pCK158 (FIG. 22), contains the resolvase under control of the pA1/04/03 promoter and the lacIq1 repressor (M üller-Hill, 1975, Prog.Biophys.Molec.Biol. 30, 227–252) with its own promoter. From pCK158 the entire cassette containing the lac-repressor and the resolvase with promoter was moved as a filled in NotI fragment into the EcoRV site of pACYC184 (Chang et al., 1978, J.Bacteriol. 134, 1141–1156), resulting in pCK151 and pCK168 (FIG. 22), differing by the orientation of the insert. In pCK151 the resolvase gene is located proximal to the origin of the plasmid.

B. Initial Testing of the Double mrs-site Plasmid pCK155 in vivo

Figure 23:
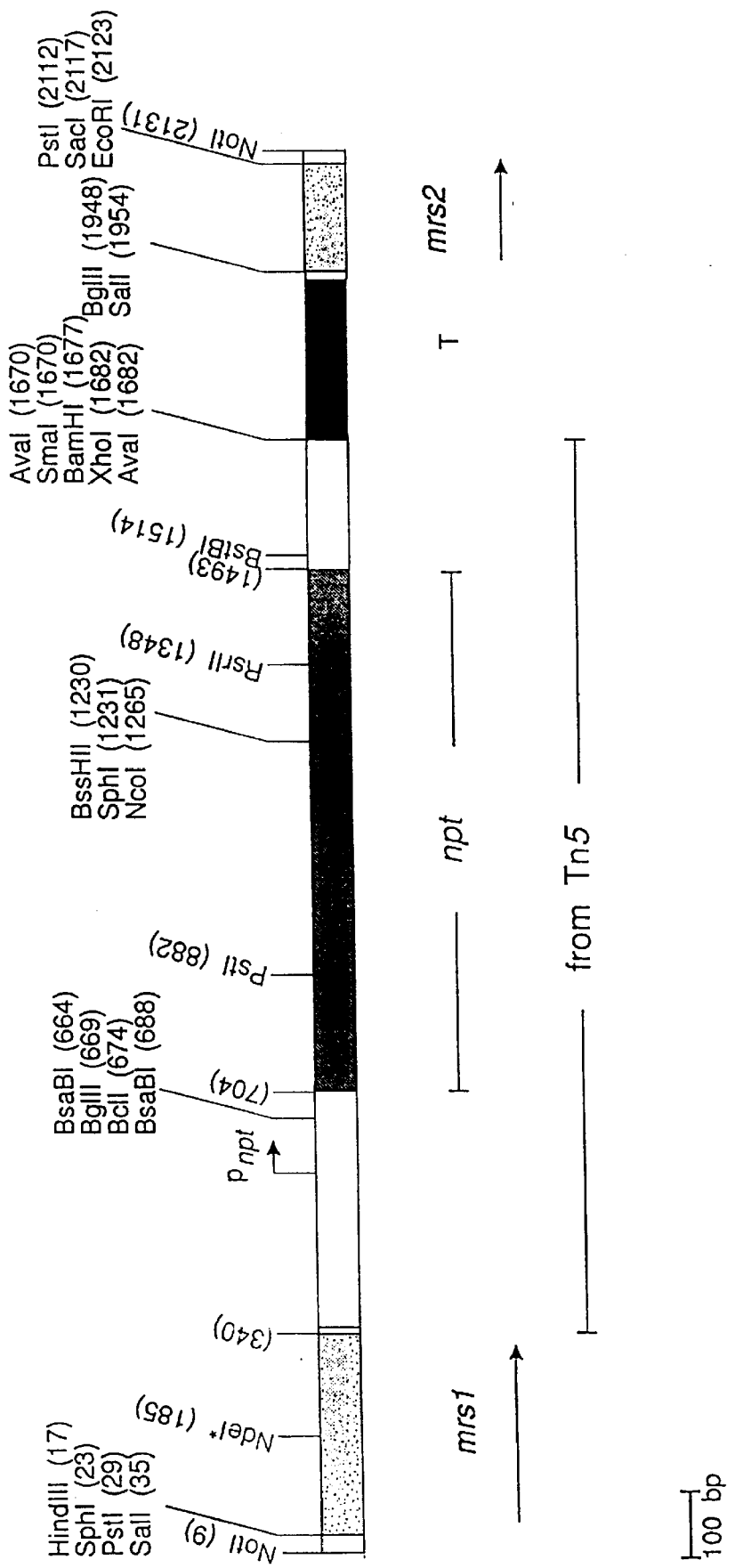
FIG. 23 shows a detailed map of pCK155.
Figure 24:
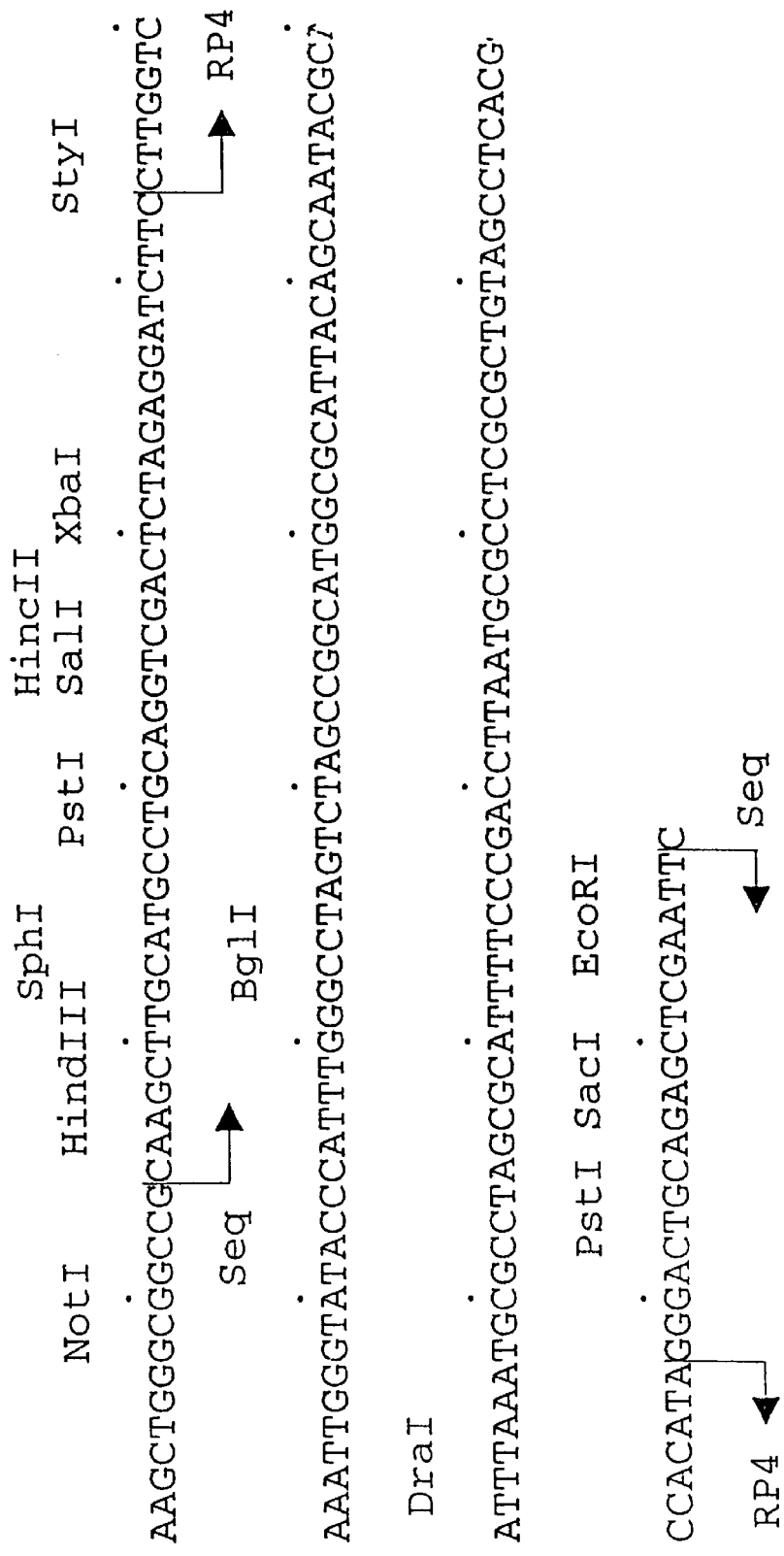
FIG. 24 shows the hybrid resolution site (SEQ ID NO:8) in pCK155delta resulting form the in vivo parA resolvase mediated recombination. The sequenced part is indicated by 'seq' and the bases originating from RP4 are marked 'RP4'.

The homologous recombination deficient (recA) strain HB101 (Boyer et al., 1969, J.Mol.Biol. 41, 459) was transformed with pCK155 and plated on LB agar plates supplemented with either 50 μg/ml of kanamycin (kan) or 100 μg,/ml of ampicillin (amp). pCK155 contains a bla gene conferring ampicillin resistance outside of the two mrs sites and an npt gene conferring kanamycin resistance within the two mrs sites (FIG. 23). Any significant homologous recombination between the two mrs sites would be identified as a lower plating efficiency on kanamycin plates than on ampicillin plates. No significant difference in plating efficiency could be detected.

pLEO26 (a plasmid containing the entire par-region of RP4 (Eberl et al , 1992a, Molec. Microbiol. in press) was subsequently transformed into the strain containing pCK155 and plated on the two types of plates as defined above, but further supplemented with 50 μg of chloramphenicol (cam) to select for pLEO26 containing the cat gene conferring chloramphenicol resistance. The transformation yielded about 2000 cam and amp resistant transformants and 4 cam and kan resistant transformants, indicating that recombination had occurred in the cells. pCKlS3 was used instead of pCK155 in a control experiment. Here no difference could be detected. Plasmids were isolated according to the method described by Birnboim et al., 1979, Nucleic Acids Res. 7, 1513–1523) from 10 pCK155/pLEO26 clones. The plasmids were separated by passing through HB101 by retransformation and subsequent plasmid preparation. The plasmids were examined by restriction mapping. In all 10 plasmids the restriction pattern resembles the expected for a plasmid having undergone a site specific recombination between the two mrs-sites. One clone was further examined by sequencing according to Sanger et al., 1977 (Proc.Natl. Acad.Sci. USA, 74, 5463–5467), using the modification for plasmid sequencing as described by the supplier of the sequencing kit (United States Biochemical) and using the M13 universal sequencing primer. The resulting sequence (FIG. 24) shows that a perfect site specific recombination had occurred (cf. restriction map of pCK155, (FIG. 23). The pCK155 derivative which had undergone deletion in-vivo was designated pCK155delta.

The strain containing pCK155 was transformed with pCK168 and plated on four different plates:

| Plate type | Number of transformants |
| --- | --- |
| 50 μg cam + 100 μg amp, no IPTG | app. 1000 |
| 50 μg cam + 100 μg amp, 2 mM IPTG | app. 1000 |
| 50 μg cam + 50 μg kan, no IPTG | app. 500 |
| 50 μg cam + 50 μg kan, 2 mM IPTG | 3 |

The drop in the uninduced cells can be ascribed to read-through of the promoter controlling the resolvase gene thus generating a background level of resolvase protein in the cells, enabling the recombination to a low extent.

C. Growth Experiments with pCK155

A strain containing pCK168 was transformed with pCK155 or pCK153 and kanamycin and chloramphenicol resistant colonies were picked.

Figure 25:
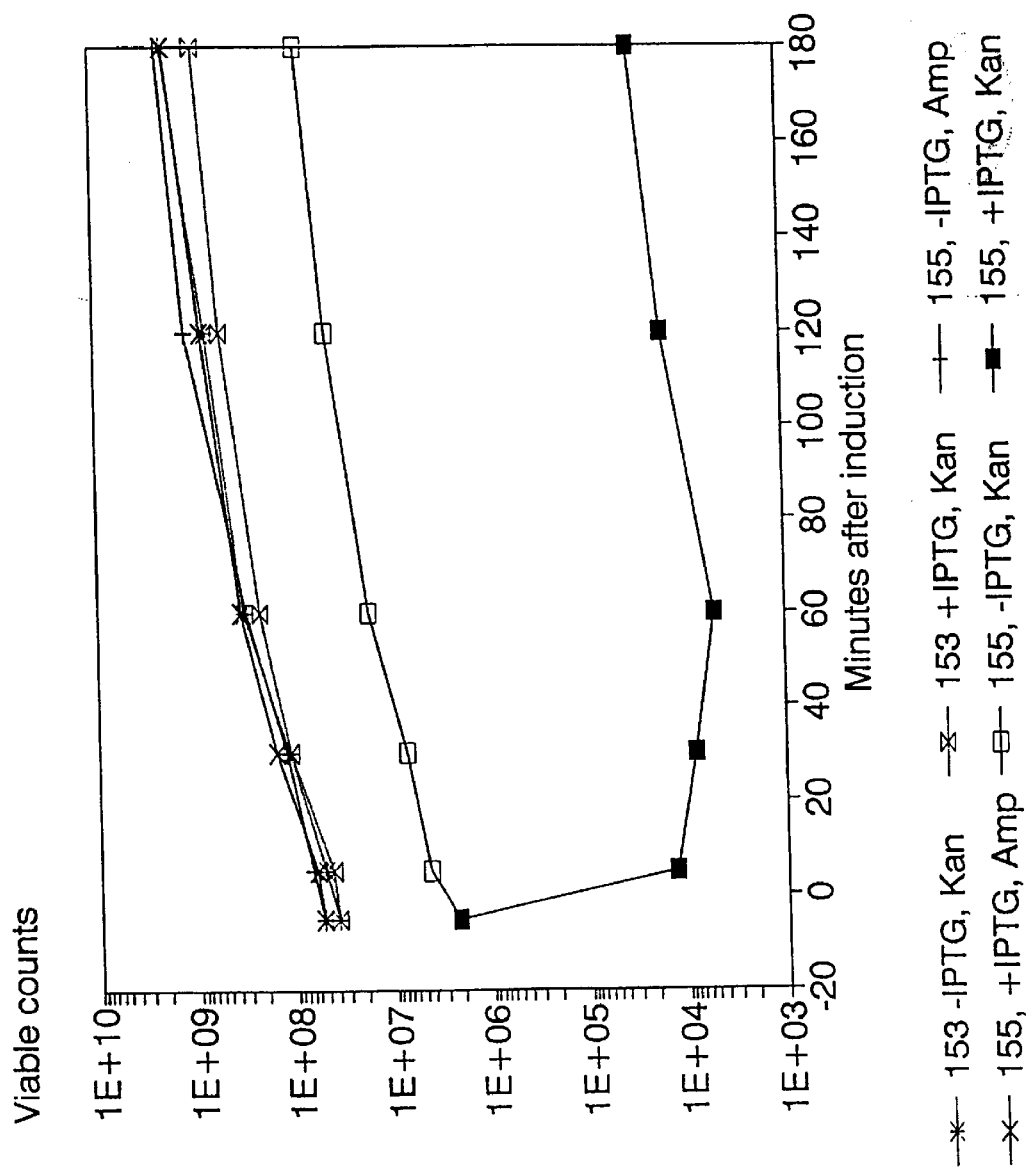
FIG. 25 shows growth experiments using pCK155 and pCK 153 (control). Viable counts are measured as plate counts from appropriate dilutions at the indicated points of time on either LB plates containing 50 µg/ml chloramphenicol and 100 µg/ml ampicillin, or 50 µg/ml chloramphenicol and 50 µg/ml kanamycin. Plates do not contain IPTG.

From a restreaked colony of each type of strain, a 10 ml LB broth culture was grown overnight in the presence of 50 μg/ml kan and 50 μg/ml cam. From these cultures 50 ml flasks were seeded to an $OD_{450}$ of 0.05 in LB broth supplemented with 50 μg/ml cam and 100 μg/ml amp. At an $OD_{450}$ of 0.5, the cultures were diluted in fresh medium of the same type to an $OD_{450}$ of 0.05. The OD was measured to ensure that the cultures were in balanced growth and at about OD 0.5 the cultures were divided and a sample was taken for determination of viable counts on each of the following plates: 50 μg/ml kan+50 μg/ml cam and 100 μg/ml amp+50 μg/ml cam. The counts on plates containing amp+ cam represent the number of plasmid-carrying viable cells, whereas the counts on kan+cam plates represent the viable cells with (at least one copy of) an intact, i.e. not deleted by recombination, copy of npt gene. After 5 minutes, IPTG was added at a final concentration of 2 mM to one half of each culture. After further 5 minutes another viable count sample was taken. Samples were then taken at time intervals and one sample after overnight growth. The viable counts as a function of time is shown in FIG. 25.

The experiment showed that following induction of the resolvase gene in cells containing the plasmids pCK168 and pCK155, a 500 fold drop in viable counts of kanamycin resistant cells compared to the uninduced culture, occurs. The drop is prominent already after 5 minutes of induction. After further 60 minutes, the difference in viable counts between the induced and the uninduced culture is 5000 times. After this point kanamycin resistant cells in the induced culture emerges at the same rate as the kanamycin resistant cells in the uninduced culture. This must be due to mutants either in the resolvase gene or the promoter or in the resolution (res) sites in pCK155, both rendering the cells unable to delete the kanamycin gene. At any point of time the kanamycin viable counts are only 1 percent of the viable counts of the uninduced culture on ampicillin plates. The explanation for this could be leakiness of the promoter regulating the resolvase or homologous recombination between the two res sites. The ampicillin viable counts in the induced culture closely follows that of the uninduced, indicating that IPTG and the resolution reaction per se is not responsible for the observed served drop in kanamycin viable counts. This is further confirmed by the observation that viable counts of the control culture (pCK168+pCK153), are essentially the same on both kanamycin and ampicillin throughout the experiment.

The conclusion of this experiment is that the resolvase action is efficient and exceptionally fast in this in-vivo setup. The promoter controlling the resolvase might be responsible for a certain degree of undesired expression of the protein and concomitant deletion of the kanamycin gene in uninduced cells. A small proportion of cells in the culture was unable to delete the kanamycin gene and grew normally in the presence of IPTG and kanamycin.

D. In Vitro Experiments Using the Purified Resolvase on pCK155 as the DNA Substrate The resolvase was purified from a culture of HB101 harboring pCK151. The cells were grown in 250 ml LB to an $OD_{590}$ of 0.8 to 1.0 and subsequently induced by 1 mM IPTG and shaken for additional 4 hours. The cells were harvested and resuspended in 7.5 ml buffer C (25 mM Tris pH 8.0, 0.1 ml4 EDTA, 50 AM benzamidin, 100 AM PMSF, 1 mM 2-mercaptoethanol, 0.02% Brij, 200 mM NaCl). The cells were opened by sonication. The lysate was ultracentrifuged at 36 000 rpm for 45 minutes at 4 C. The supernatant was dialysed against buffer B (buffer A with 250 mM NaCl final concentration). The resulting pellet was washed in buffer A and subsequently dissolved in 0.5 ml buffer C (buffer A with 1M NaCl final concentration). The solution was concentrated to app. 50 µl.

pCK155 was prepared by two rounds of cesium chloride density gradient centrifugation (Maniatis et al., 1982, Molecular cloning: A Laboratory Manual, Cold Spring Harbor Laboratory Press, New York). The concentration of the DNA was determined by UV absorbance at 260 nm and the protein concentration was determined by the method of Bradford, 1976 (Anal.Biochem. 72, 248–254).

The resolution assay was performed with 110 ng of plasmid DNA in a reaction volume of 10 µl. The final concentration of the reaction buffer was 150 mM KCl, 10 mM $MgSO_4$. 30 mM Tris-HCl pH 7.5 and 1 mM 1,4-dithioerythritol (DTE). The reactions were stopped by heat inactivation at 65° C. for 10 minutes. The samples were assayed by digesting with NdeI in a final volume of 30 µl. To the above reaction mixture, enzyme buffer and enzyme was added and the resulting mixture was incubated for 1 hour at 37° C. Samples were run on a 0.7 % agarose gel at 2 V/cm overnight. The gel was dyed with EtBr and photographed on a Polaroid negative film using UV light. The negatives were scanned on a Shimatzu scanner model CS-930 V-05. The area under each peak was evaluated as an indication of the amount of DNA in the corresponding band on the gel when corrected for fragment size (cf. FIG. 26 and FIG. 27).

Figure 26:
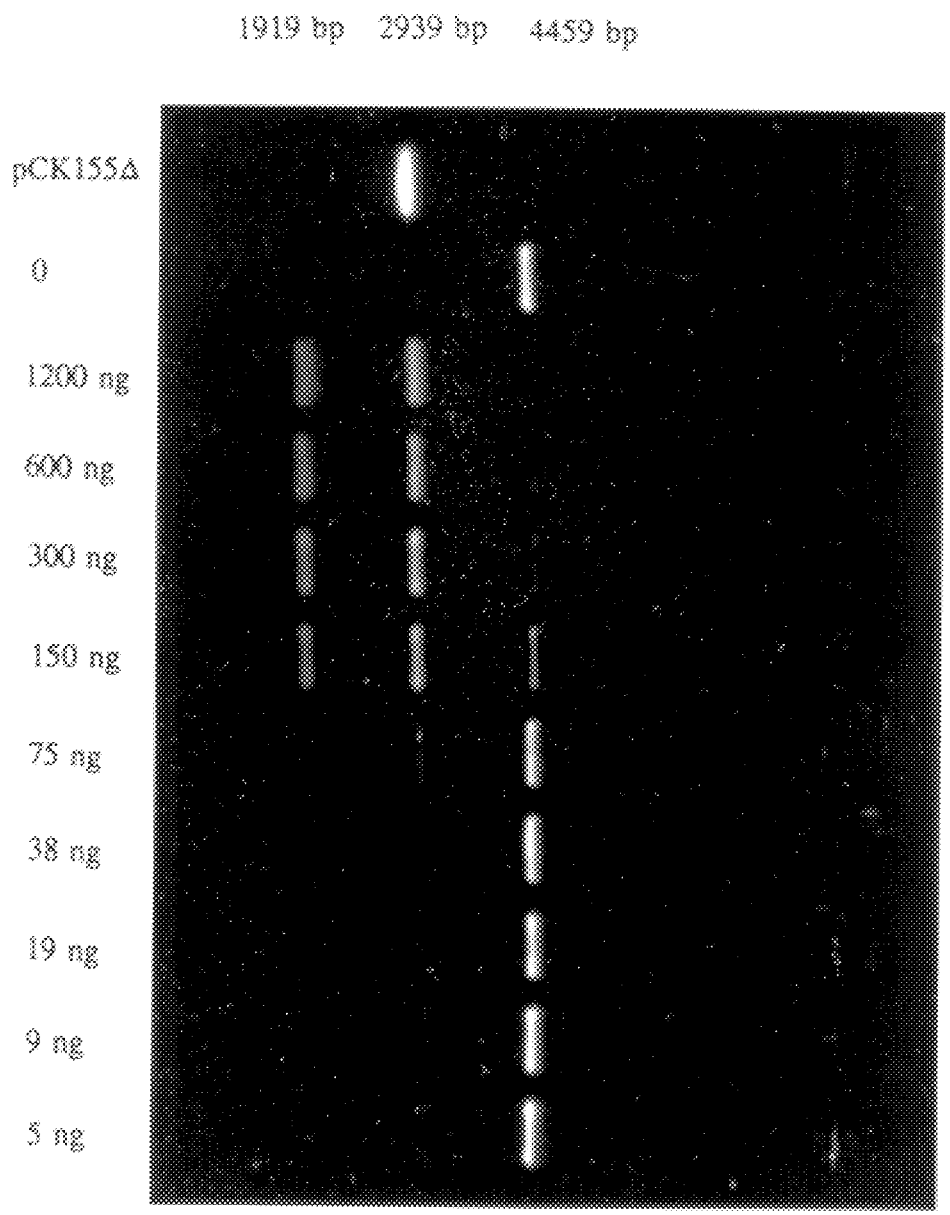
FIG. 26 shows in vitro titration assay of resolvase reaction (0.7% agarose gel). Lane 1 contains 110 ng of pCK155delta (0). Lanes 2–11 contain 110 ng of pCK155 treated with the indicated amounts of resolvase (5–1200 ng) for 30 minutes at 37° C. All reactions are treated with restriction enzyme NdeI for 1 hour prior to applying the samples to the gel. The band at 4459 bp represents the unresolved plasmid pCK155 and the bands at 2939 bp and 1919 bp, respectively represent plasmids, pCK155delta and pCK15omega, respectively, FIG. 27 show scanning curves corresponding to bands illustrated in FIG. 26. Absorption units are arbitrary.
Figure 27:
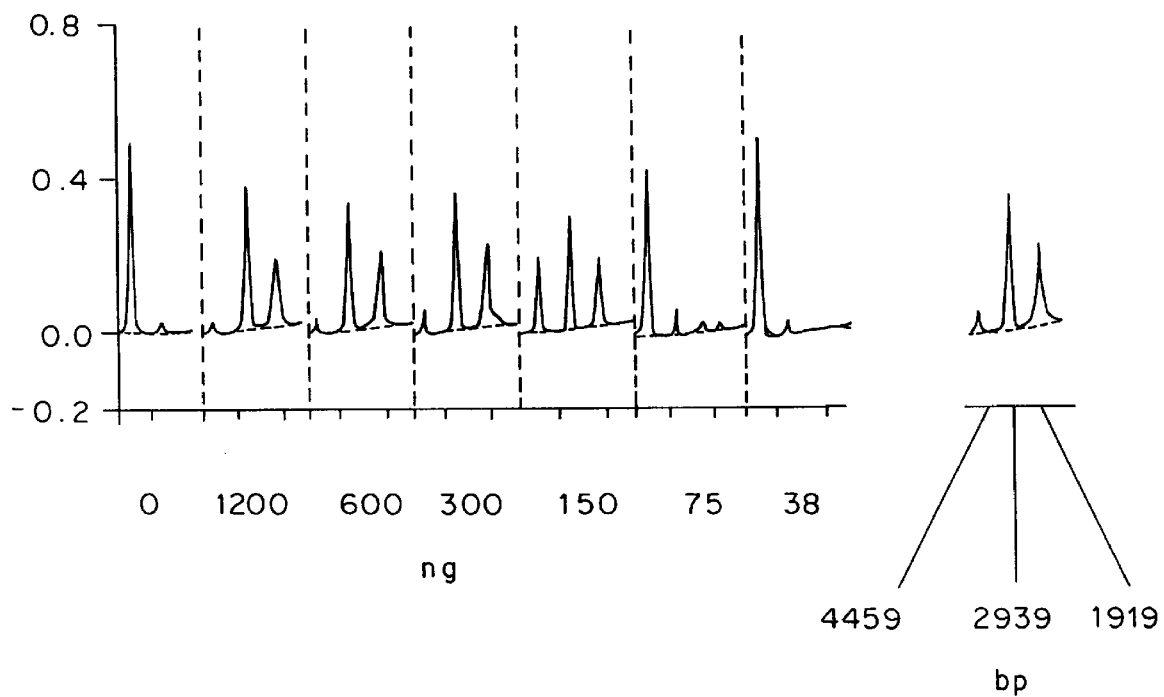

The unreacted pCK155 yielded two bands of 4.5 kb and 0.4 kb, while the resolved plasmid, which is converted into two species, pCK155delta and pCK155omega, yields two bands of 2.9 kb and 1.9 kb, respectively (FIG. 26).

E. Titration of the Resolvase

Figure 28:
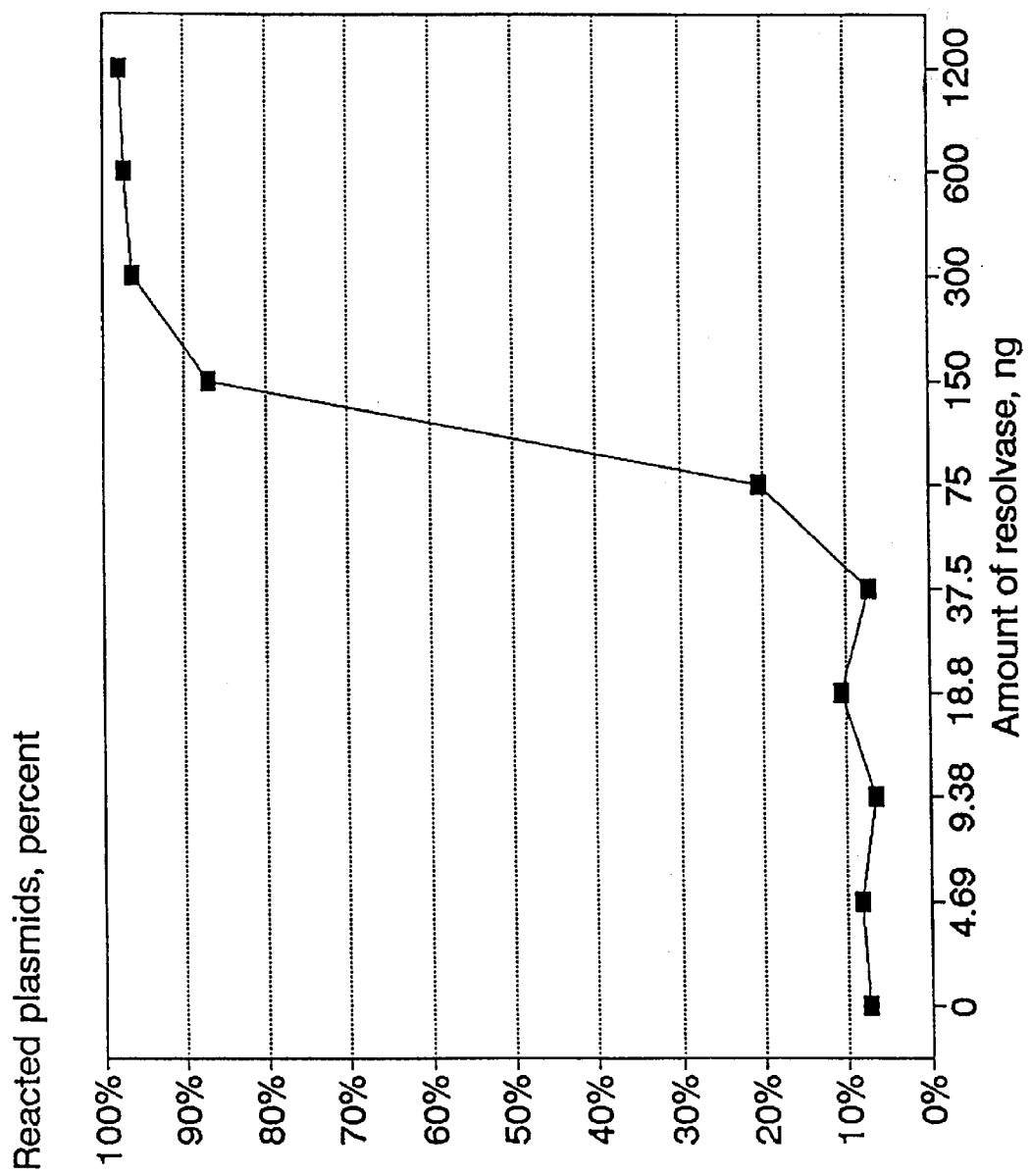
FIG. 28 shows in vitro titration of resolvase reaction. The percentage of reacted plasmid is defined as the area of the peaks shown in FIG. 27 from scans of pCK155delta and pCK15-omega divided by the respective fragment lengths (2939 bp and 1919 bp) relative to the area of the major peak from pCK155 divided by the length of the pCK155 NdeI major fragment (4459 bp)

To 100 ng of pCK155 was added varying amounts of resolvase: 1200, 600, 300, 150, 75, 38, 19, 9, 5 and 0 ngs. The reaction was performed at 37C. for 30 minutes. The results were plotted in FIG. 28. A relatively sharp drop in ability to resolve the plasmid, expressed as the fraction of deleted plasmids relative to intact plasmids, is observed between 150 ng and 75 ng of protein, corresponding to about 60 molecules of resolvase per res site (150 ng). This indicates that a lower level of the resolvase concentration can be determined and below this level little recombination occurs. When the level of resolvase is above this level, essentially all substrate is converted.

The above Figure shows that even without adding resolvase, a small fraction of substrate is converted. This could be due to indigenous resolvases in the *E. coli* host used for propagation of the plasmid. Also a small fraction cannot be converted even at very high concentrations of resolvase. This can be accounted for by noting that the resolvase requires a supercoiled substrate for reaction and that a small fraction of even a highly purified plasmid purification will be relaxed.

F. Kinetics of Resolvase in vitro

Figure 29:
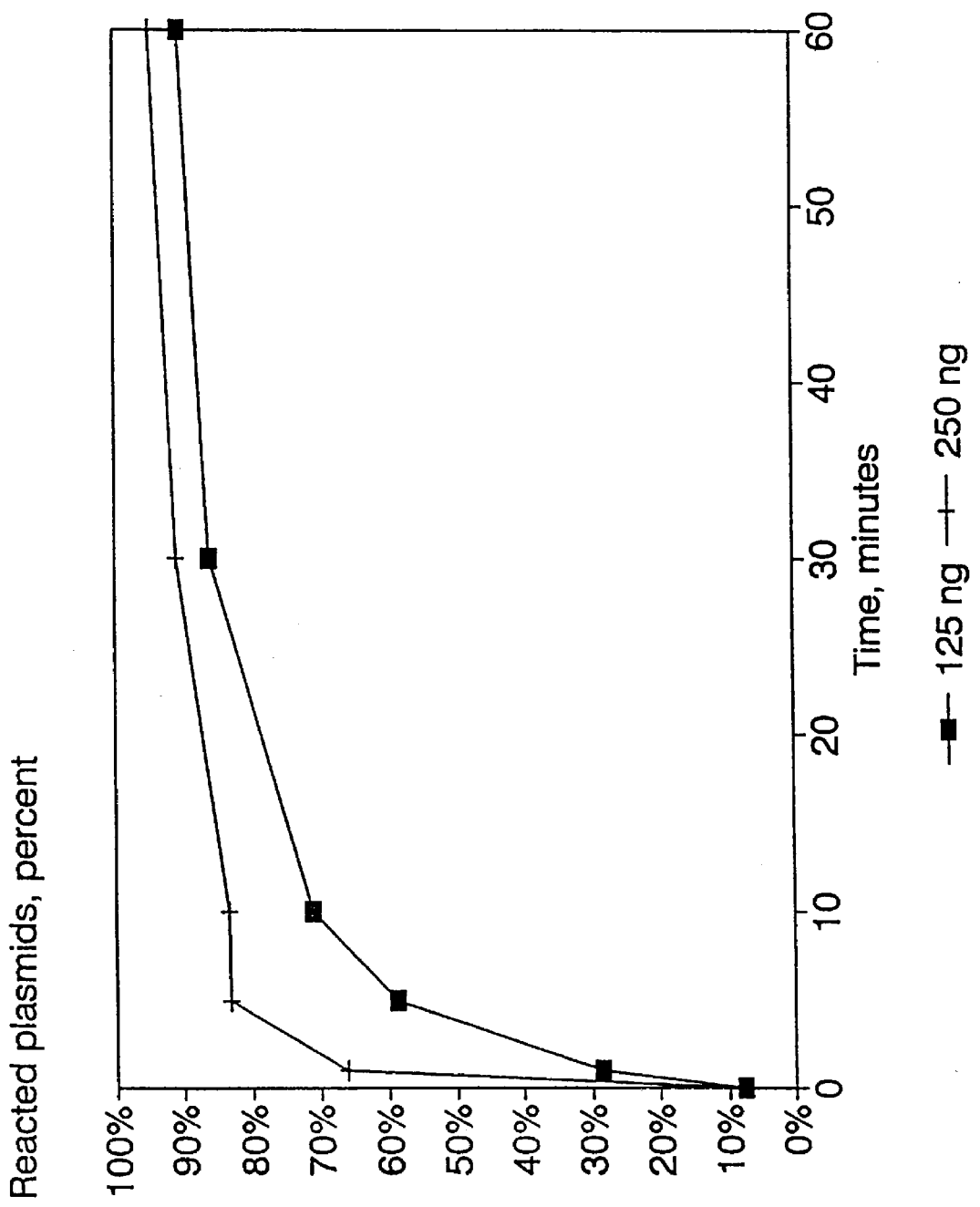
FIG. 29 shows the kinetics of resolution reaction in vitro. 110 ng of pCK155 was treated with the two indicated amounts of resolvase and the reaction was stopped by heat inactivation at the indicated times.

Samples with 110 ng of the above DNA substrate and either 125 ng or 250 ng of resolvase were incubated at 37° C. at varying periods of time: 1, 5, 10, 30 and 60 minutes. The data shown in FIG. 29 shows that when the amount of enzyme is sufficient, the reaction is almost completed within the first minute (more than 65% conversion) and has reached the final extent of reaction within the first 5 minutes. When the amount of enzyme is less than optimal, the kinetics are slower which can be accounted for by considering the apparent reaction speed as the speed of building up the complexes needed for resolution.

EXAMPLE 17

Intracellular Expression and Stability of a Mutant *Staphylococcus Aureus* Nuclease Gene in *Escherichia Coli*

A. Cloning of the Mutant Staphylococcal Nuclease Gene for Intracellular Expression As it has been described in Examples 13 and 14 above, the wild type nuclease gene from the plasmid pFOG408 without its signal sequence may be expressed intracellularly and used as the basis for a conditional cell function-limiting system in bacteria. However, it has been found that although the expression of the wild type nuclease protein is predominantly intracellularly, some export of the signal peptide-less enzyme outside the cell may be observed. Accordingly, it was attempted to prevent such extracellular transport of staphylococcal nuclease by removal, not only of the signal peptide, but of further amino acid residues of the mature protein.

Figure 31:
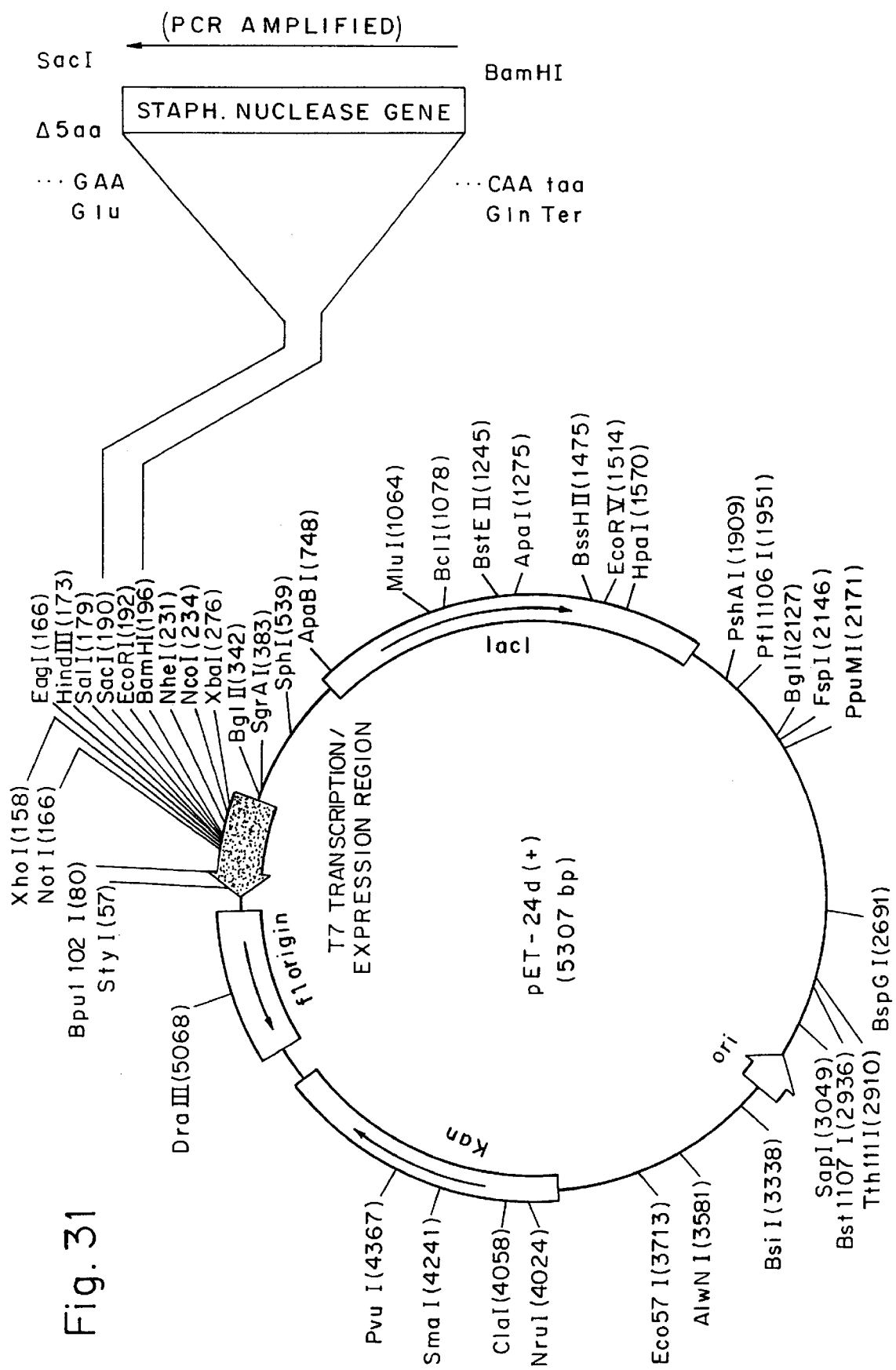
FIG. 31 shows the construction of pSNUC24-26 by ligation of PCR amplified, truncated Staphylococcus aureus (Foggi) nuclease encoding gene fragment digested with BamHI and SacI (deletion of 9 amino acid residues of the mature nuclease protein) to pET24d(+) also digested with BamHI and SacI.

DNA sequences encoding a total of 30 amino acid residues (21 amino acid residues of the signal peptide sequence and 9 amino acid residues of the mature protein, cf. FIG. 30) of the nuclease derived from the *Staphylococcus aureus* (Foggi) strain (ATCC 27355) were deleted and rest of the gene segment constituting 426 bp was PCR amplified using oligonucleotide primers flanked with appropriate restriction enzyme sites and cloned into pET24d(+) plasmid vector (5307 bp) (Novagen, Inc. 597 Science Drive, Madison, Wis. 53711). The location, lengths and the nucleotide sequences of the oligonucleotide primers which were used for PCR amplication of the staphylococcal nuclease gene are described in FIG. 31. For the intracellular biological activity, the specific amino acid residue # 31 (Glu encoded by the nucleotide sequence GAA) at the N-terminal end of the nuclease gene was selected as the first amino acid of the gene. This selection of the first amino acid was based on Tucker et al., 1979, Molecular and Cellular Biochemistry, 23, 131–141, according to which the deletion of amino acid residues starting from # 10 and onwards of the *Staphylococcus aureus* (Foggi) nuclease produces a marked fall in both structure and activity of the enzyme.

For cloning, the pET24d(+) vector was treated with BamHI and SacI restriction endonucleases and ligated to similarly digested PCR amplified staphylococcal nuclease gene fragment as defined above. The pET24d(+) plasmid vector comprises a promoter sequence from bacteriophage T7, the lac operator (lacO) DNA segment which interacts with the repressor protein in the absence of IPTG, a DNA sequence for ribosome binding site (rbs), followed by several unique bacterial restriction endonuclease sites (multiple cloning sites or MCSs) for the insertion of a foreign DNA segment. The repressor protein is encoded by the lacI gene which is located on the pET24d(+) vector. Also, the pET24d (+) vector comprises a gene that encodes for resistance to kanamycin (KM), and the colE1 replication origin. The DNA sequence (ATG) that codes for the translational start codon (Met) is located immediately after the rbs in the multiple cloning site for expression of the nuclease protein from the truncated nuclease gene segment without the translational first codon. There was no BamHI or SacI restriction endonuclease sites within the nuclease gene fragment.

Figure 32:
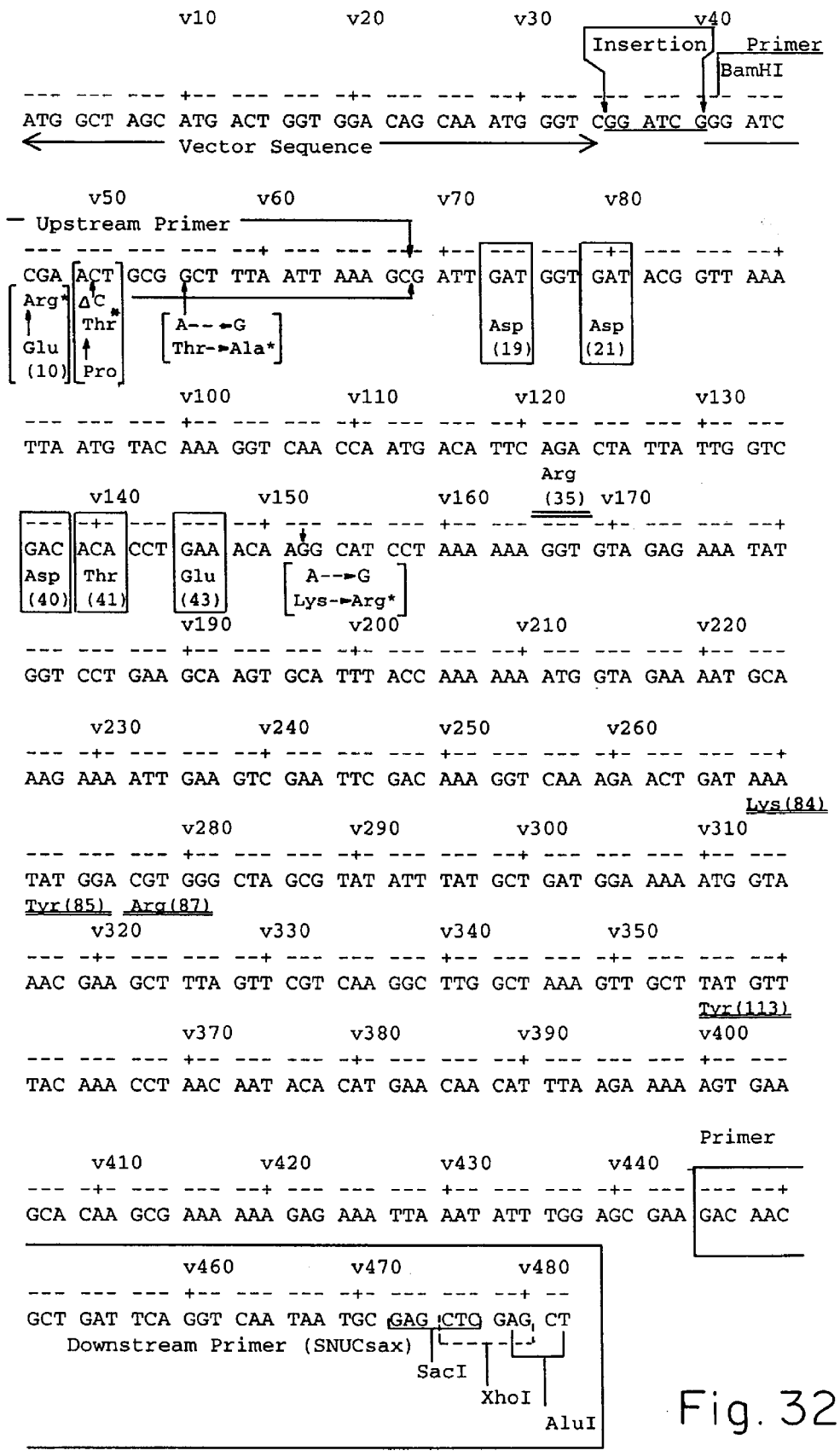
FIG. 32 shows the nucleotide sequence (SEQ ID NO:12) of the mutant staphylococcal nuclease gene in pSNUC24-26. Amino acids in boxes represent essential amino acids required for binding to $Ca^{2+}$ providing the conformational stability of the protein. Amino acids which are doubly underlined are important for conformational stability of the protein. An * indicates amino acid residues after mutation. Amino acid positions in brackets represent the position of the amino acids in the wild type nuclease gene without signal sequence (mature protein)

The pET24d(+) vector ligated to the digested PCR amplified staphylococcal gene fragments as defined above was used for transformation of the *E. coli* strain HMS174(DE3) (genotype: F⁻, recA, $r_{k12}$-, $M_{k2}$-, Rif^r) (Novagen, Inc., Madison, Wis.) which carries the T7 RNA polymerase gene under the lacUV5 control located on the chromosome. Transformants were selected on DNAse agar with toluidine blue (3BL cat# 99081) supplemented with 75 μg per ml of kanamycin. A number of clones with the characteristic nuclease "halo" were identified after 16–24 h of incubation at 37° C. However, a few colonies were found to be relatively slow growing on the same agar plates and showed secondary nuclease activity as evidenced by a relatively slowly developing "halo" on the DNAse test agar. One of these relatively slow growing colonies was selected and further tested with regard to the nature of the nuclease gene. The cloned nuclease gene in the pET24d(+) which was isolated from the slow growing *E. coli* HMS174(DE3) transformants was designated as pSNUC24-26 (FIG. 32).

pSNUC24-26 in the *E. coli* HMS174(DE3) host strain was deposited in accordance with the Budapest Treaty with the American Type Culture Collection (ATCC, 123C1 Parklawn Drive, Rockville, Md. 20852, USA on 8 Oct. 1993 and assigned the accession number ATCC 69462.

B. Determination of Genetic Characteristics of the Staphylococcal Nuclease Gene Cloned in pSNUC24-26

In order to determine the genetic characteristics of the nuclease gene in pSNUC24-26, nucleotide sequence analysis was performed by following the Sanger dideoxy chain termination method using the T7 promoter primer (5'-TAATACGACTCACTATA-3') (SEQ ID NO:9) and the T7 terminator primer 3'-TGGCGACTCGTTATTGATC-5' (SEQ ID NO:10) (this primer being complementary to the sequence 5'-ACCGCTGAGCAATAACTAG-3') (SEQ ID NO:11). The complete nucleotide sequence of the nuclease gene in pSNUC24-26 is presented in FIG. 32. A number of point mutations and addition of several base pairs were detected in the cloned staphylococcal nuclease gene in pSNUC24-26 resulting in a mutant form of the gene. A small DNA sequence, 5'-GGATCG-3', was inserted by an unknown mechanism immediately upstream of the BamHI site of the left side primer sequence during the PCR DNA amplification. Also, deletion of a nucleotide base, C, in the second position of the second codon [CCT>CT, i.e. C(ΔC)T], and transition of A>G at the 4th and 36th codons (ACT>GCT at the 4th and AAG>GAG at the 36th positions) were evidenced.

Although, the deletion of a nucleotide base, C, at the second codon resulted in a frameshift mutation, the wild type amino acid residues of the nuclease protein were restored at the 3rd codon (GCG-Ala) and from the 5th codon (TTA-Leu) onwards. As a result, for the conformational stability and biological activities, the amino acid residues at positions 19 (GAT-Asp), 21 (GAT-Asp), 40 (GAC-Asp), 41 (ACA-Thr) and 43 (GAA-Glu) that have been shown to be essential for binding to $Ca^{2+}$ (Tucker et al., 1979, Molecular and Cellular Biochemistry, 23, 67–86) together with the amino acid residues at positions 35 (AGA-Arg), 84 (AAA-Lys), 85 (TAT-Tyr), 87 (CGT-Arg) and 113 (TAT-Tyr) that have been shown to be essential for intramolecular interactions to establish the "active site" of the protein (Tucker et al., 1979), were not affected by this mutation (cf. FIG. 32).

However, the changes in amino acid residues from Glu>Arg at position 10, from Pro>Thr at position 11 due to a single base deletion (CCT>CT) and the insertion of the DNA sequence 5'-GGATCG-3' upstream of the primer location, and changes in the amino acid residues of Thr>Ala at position 13 and of Lys>Arg at position 36 due to the point mutations (A>G) of the wild type nuclease gene may have altered the extracellular transport and relative biological activities of the protein encoded by the plasmid pSNUC24-26.

C. Kinetics of the pSNUC24-26-Encoded Staphylococcal Nuclease in *E. Coli* HMS174(DE3)

Figure 33:
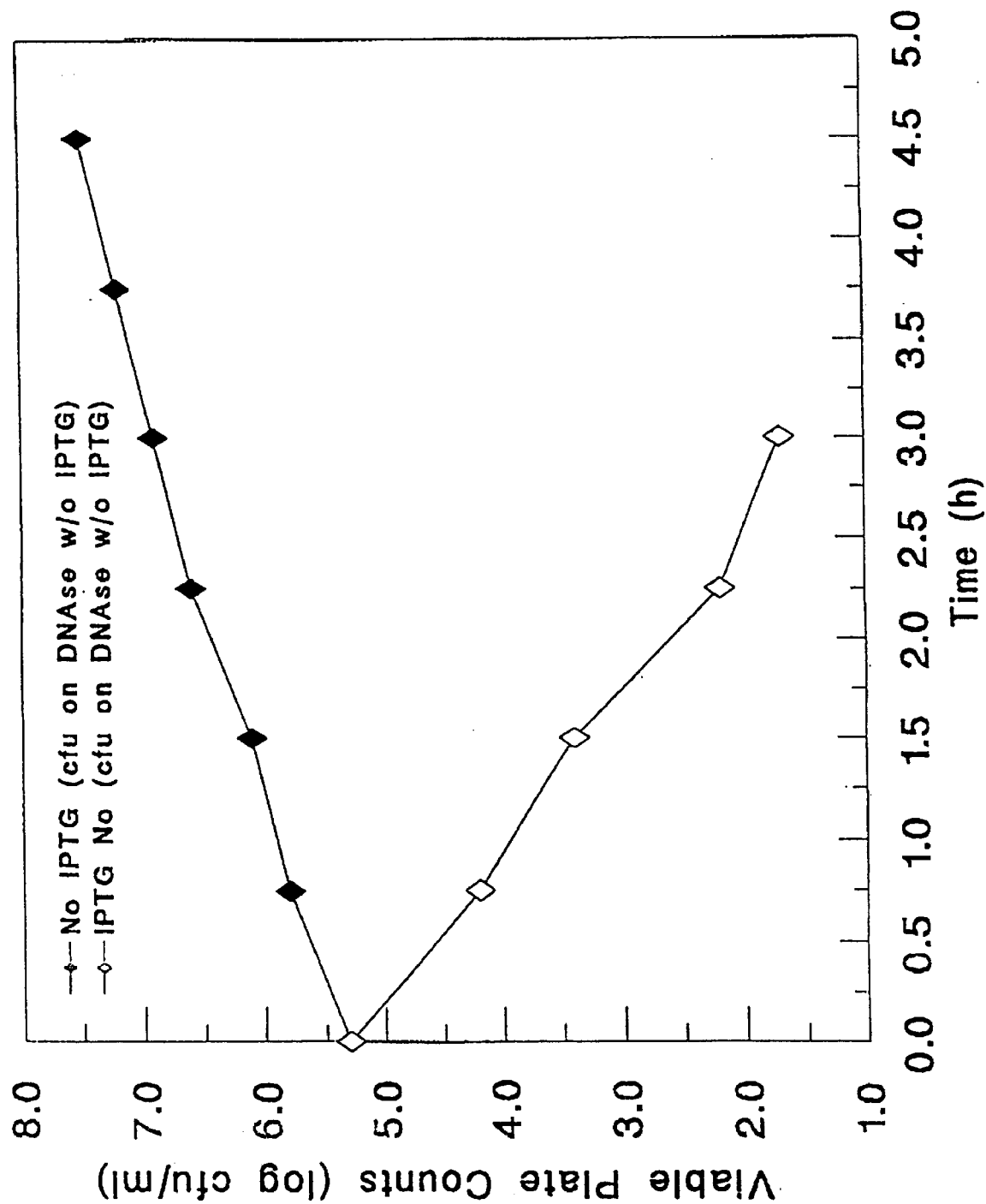
FIG. 33 shows kinetics of staphylococcus nuclease (SNUC) induction in E. coli HMS174(DE3) harboring pSNUC24-26.

To determine the cell function-limiting (or killing) efficiencies of the mutant staphylococcal nuclease gene in the pSNUC24-26 plasmid, induction of the *E. coli* HMS174 (DE3) carrying this plasmid was performed by the addition of 1 mM of IPTG in an exponentially growing liquid culture. Before and after addition of IPTG (i.e. induction), aliquots of serially diluted culture were tested on DNAse Test Agar plates without IPTG. A decrease in the cell number at the level of >4 log was evidenced within the first 3 h time period following induction when plated onto DNAse Test Agar plates without IPTG, (FIG. 33).

D. Intracellular Stability of the Mutant Nuclease Enzyme as Determined by Immunological Assay The stability of the mutant nuclease enzyme within the *E. coli* cells was determined by ELISA assay using polyclonal antibodies raised in rabbit against purified wild type *Staphylococcus aureus* (Foggi) nuclease. An exponentially growing culture of *E. coli* HMS174(DE3) carrying pSNUC24-26 was induced by the addition of 1 mM of IPTG for 30 minutes. Immediately after induction, 40 μg per ml of chloramphenicol was added to the culture to inhibit protein synthesis and the cells were continued to grow for another 3 hours. Aliquots of the culture were separated at every 30 min interval for up to 3 h, centrifuged, washed 2×with phosphate buffered saline (PBS) (pH 7.2), resuspended in PBS and the cells were disrupted by using a sonic disrupter to release the total cellular proteins. An aliquot of the proteins released at every time period following chloramphenicol treatment was immobilized into a microtiter plate and ELISA assay was performed as described in Example 14.

Figure 34:
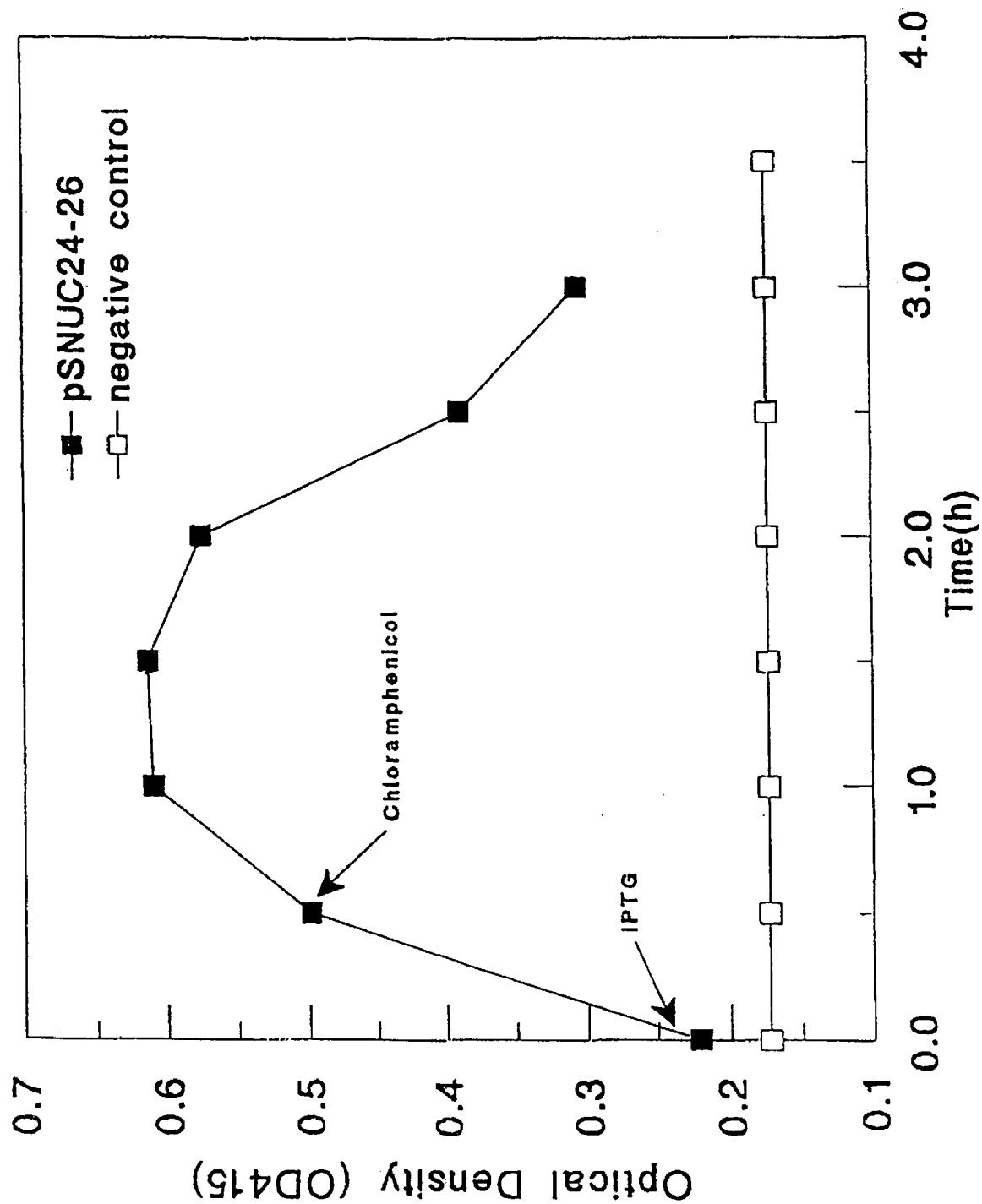
FIG. 34 illustrates intracellular stability of the mutant staphylococcal nuclease encoded by pSNUC24-26.

About 2.5 fold increase in the nuclease protein was evidenced following induction and the nuclease protein was stable within the cell>1.5 h following chloramphenicol treatment (FIG. 34). Therefore, the intracellular stability of the mutant nuclease protein was not affected to the same extent as it was observed with the wild type nuclease protein. However, the basal level of production of nuclease was found to be extremely low in the mutant staphylococcal nuclease protein suggesting that the modifications in the nucleotide sequences may have contributed to less extracellular transport of the mutant protein.

E. Identification of the Mutant Nuclease Protein by Immunological Assays

For identification of the mutant nuclease protein in the pSNUC24-26 plasmid, western blot analysis was performed by using polyclonal antibody raised against purified wild type *Staphylococcus aureus* (Foggi) nuclease in rabbit. Total cellular proteins in *E. coli* HMS174(DE3) harboring pSNUC24-26 plasmid before and after IPTG induction were subjected to electrophoretic separation in denaturing polyacrylamide gel with appropriate size standards. The proteins were immobilized on a nitrocellulose membrane and subjected to western blot analysis according to the procedure as described in Example 13.

The western blot analysis of the mutant staphylococcal nuclease showed very weak signal before induction. However, following induction, the signal increased significantly. In the wild type clones, differences in the intensities of the nuclease enzyme before and after induction was indistinguishable. This suggests that the mutant nuclease gene encoded the modified protein that may significantly have prevented the extracellular transport of the modified mutant nuclease.

F. Cloning of the Mutant Staphylococcal Nuclease Gene in the pSE420 Plasmid Vector The intracellular effectiveness of the above mutant staphylococcal nuclease under the control of a different promoter element was tested by cloning the mutant staphylococcal gene with the upstream coding sequences under the control of the $P_{trc}$ promoter/lacO (a synthetic promoter generated by the fusion of the tryptophan and the lactose promoters) in pSE420 (Invitrogen Corp., 3985 B Sorrento Valley Blvd., San Diego, Calif. 92121). The NcoI and the XhoI restriction endonuclease-digested fragment from pSNUC24-26 plasmid consisting of the mutant staphylococcal nuclease gene with the upstream coding sequences was purified and ligated to the similarly digested pSE420 plasmid vector and the resulting recombinant plasmid was designated pSNUC420-26.

pSNUC was transformed into *E. coli* NM522 (Genotype= F'{proAB+lacI$^q$ lacZ ΔM15}, supE, thi1, (lacproAB) , hsd5 (r$^-$ m$^-$)$^{\lambda-}$ (Invitrogen Corp.)

pSNUC420-26 in the *E. coli* NM522 host strain was deposited in accordance with the Budapest Treaty with the American Type Culture Collection (ATCC, 12301 Parklawn Drive, Rockville, Md. 20852, USA on 8 Oct. 1993 and assigned the accession number ATCC 69463.

G. Kinetics of SNUC Induction in *E. Coli* NM522 (-SNUC420-26)

Figure 35:
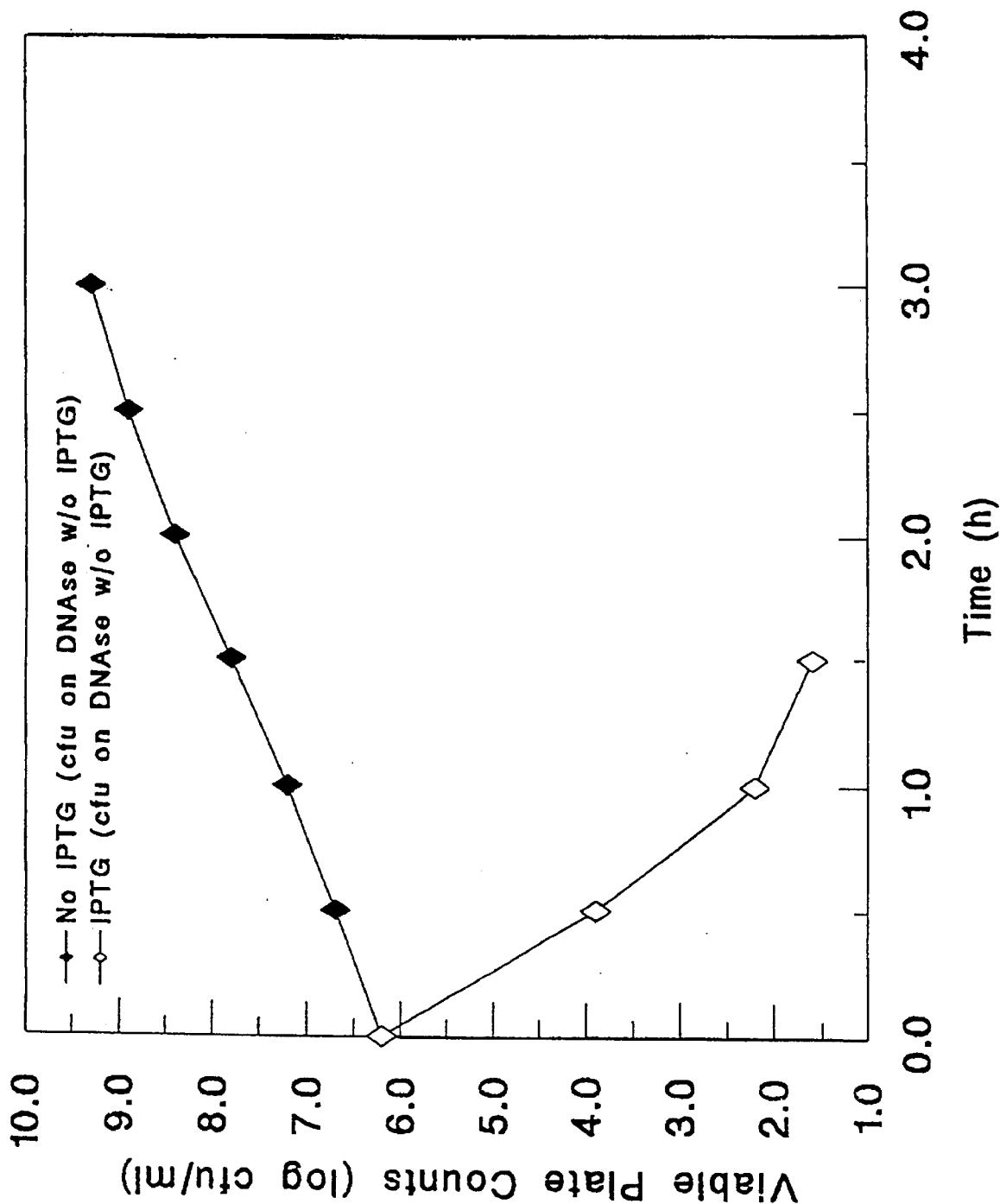
FIG. 35 shows kinetics of staphylococcus nuclease (SNUC) induction in E. coli NM522 harboring pSNUC420-26.

The procedure for induction with IPTG and viable plate counts as described above for pSNUC24-26 was followed. The results of the induction are presented in FIG. 35. A significant reduction of cell numbers (>5 log) within the first 1.5 h time period was evidenced.

H. Stability of the Mutant Nuclease in *E. Coli* NM522 (pSNUC420-26)

Figure 36:
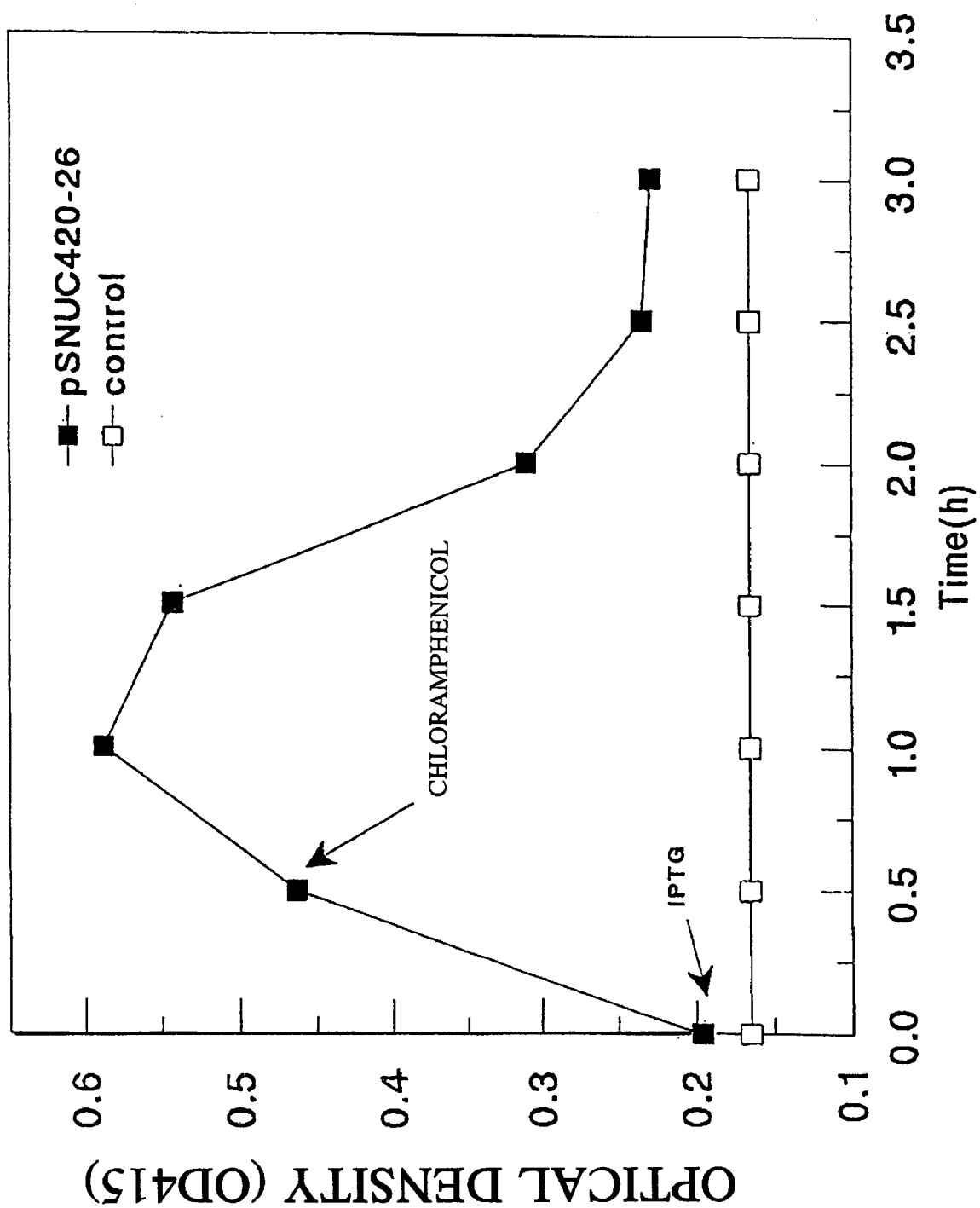
FIG. 36 illustrates intracellular stability of the mutant staphylococcal nuclease encoded by pSNUC420-26.

The intracellular stability of the mutant nuclease protein in pSE420-26 was determined by ELISA assay as described above for pSNUC24-26. The results are presented in FIG. 36. About 2-fold increase in the intracellular nuclease was evidenced following induction. Also, the intracellular stability of the mutant nuclease was determined to about 1.5 h following treatment with rifampicin. It was also observed that the basal level of nuclease expression during uninduced state was negligible. This result is comparable with that of the ELISA assay in pSNUC24-26.

I. Identification of the DSE420-26-Encoded Mutant Nuclease by Western Blot Analysis Western blot analysis of the mutant staphylococcal nuclease in pSE420-26 showed low level of signal before induction and the higher signal following induction as observed above for the pSNUC24-26 plasmid.

EXAMPLE 18

The Use of the xth Exonuclease III Gene from *Escherichia Coli* in Combination with a Mutant Staphylococcal Nuclease Gene (snuc*) for the Containment of Genetically Engineered Micro-Organisms The exonuclease III of *E. coli* has multiple catalytic activities in vivo: (i) it has 3'-5'exonuclease activities specific for the double stranded DNA, (ii) it can remove a number of 3'-end termini from duplex DNA, including 3'-phosphates, (iii) it is an AP endonuclease which cleaves phosphodiester bonds at AP sites to yield base-free deoxyribose 51-phosphate end groups, (iv) it has an RNase H activity which preferentially degrades the RNA strand in a RNA-DNA hybrid duplex (Weiss, 1981).

The exonuclease III of *E. coli* is encoded by the gene xth, the sequence of which has been determined and reported by Saparito et al. (1988).

The coding sequence including the ribosome binding site (SD sequence) of the xth gene was PCR amplified using two oligonucleotide primers L-XTH and R-XTH and cloned into the pCRII® vector and then cloned into the pSE420® plasmid vector (Novagen, Inc.) at the XbaI and Kpn restriction sites under the control of the trp-lac promoter ($P_{tac}$)/lac operator (lacO) and lacjq. The orientation of the cloned xth gene in pSE420 vector has been confirmed by restriction enzyme analysis. The $P_{tac}$/lacO::xth gene from the pSE420 vector will be recovered by restriction enzyme digestion and cloned into pUC18Not vector which already has the $P_{tac}$/lacO::snuc* and the lacI$^q$ gene.

Following cloning, the $P_{tac}$/lacO::xth, $P_{tac}$/lacO::snuc* and lacI$^q$ genes as a complete genetic cassette will be recovered from the pUC18Not vector as a NotI fragment and inserted into a similarly digested transposon vector pUTKM for insertion on the chromosome of the host microbial strain. In this system, both the staphylococcal nuclease gene (snuc*) and the exonuclease III (xth) gene can be expressed simply by addition of IPTG and the efficiency of killing of the host strain can be determined by viable cell plate counts. During the normal physiological conditions (uninduced stage), both genes will remain silent due to the binding of the repressor protein encoded by the lacd gene to the lacO DNA sequence.

EXAMPLE 19

The Construction of a Replicon Simultaneously Expressing the snuc* and the hok Genes The $P_{tac}$/lacO::snuc* and the lacI$^q$ gene cassette was recovered from the pSNUC26-420 vector using the EcoRV and XhoI restriction enzymes and blunt ended by "fill in" reaction. This fraction was cloned in pBAP24h vector (Bej et al., 1992) at the SalI restriction site which was also blunt ended by "fill in" reaction. The pBAP24h vector has the hok gene under the control of the $P_{tac}$/lacO promoter-operator and the lacI$^q$. Upon induction with IPTG, both genes, snuc* and hok can be expressed simultaneously. The cell function-limiting effects due to the simultaneous expression of the hok and the snuc* genes can be monitored by induction with ITPG and viable cell plate counts. The clones with the appropriate orientation of the genes was confirmed by restriction analysis.

EXAMPLE 20

Dual Conditional Lethal System in *Pseudomonas Putida* 2442 Using Mutant Staphylococcal Nuclease (snuc*) and gef Genes Under the Control of 3-Methyl Benzoate (3-MB)

A. Objectives

The objectives of the present study was to clone the mutant version of the staphylococcal nuclease gene (snuc*, also referred to herein as nucS*) in combination with the gef gene in *P. putida* 2442 strain under the regulatory genetic elements which are inducible by a xenobiotic compound, 3-methyl benzoate (3-MB), and determine the effectiveness of such a "dual" conditional lethal system in the presence or absence of 3-MB in a pure culture.

B. Genetic Construction of Dual Conditional Lethal System

Figure 37:
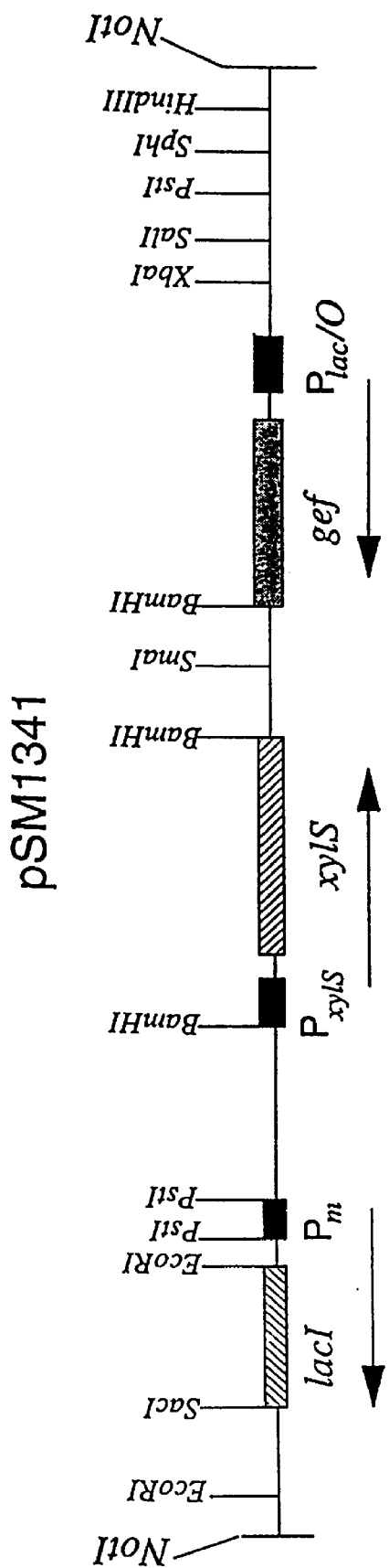
FIG. 37 is a schematic diagram of the plasmid pSM1341 showing the suicide construct of the gef gene under the control of 3-MB.
Figure 38:
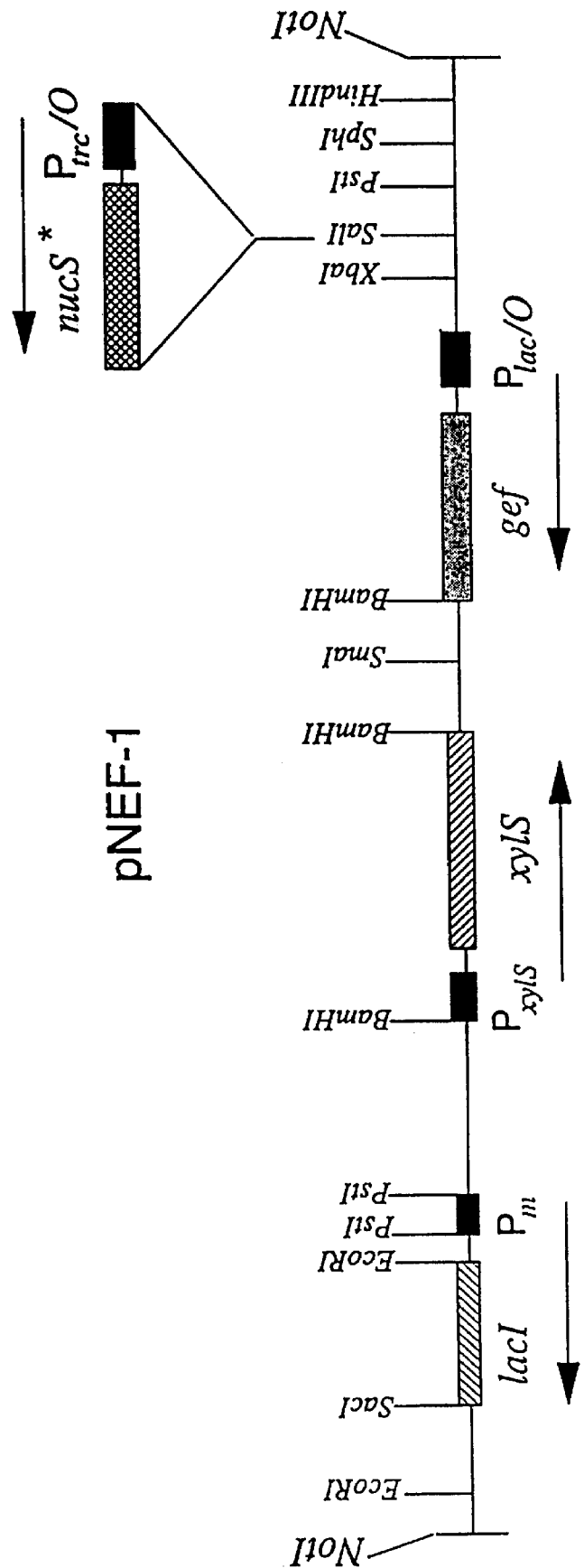
FIG. 38 is a schematic diagram of the plasmid PNEF-1 showing the suicide construct of both nucS* and gef genes under the control of 3-MB.

The snuc* gene under the regulation of $P_{trc}$/lacO was recovered from pSNUC420-26 plasmid (see Example 17) following treatment with NdeI and XhoI restriction endonucleases and "end repaired" with Klenow fragment of DNA polymerase I (Ausubel et al. (eds), 1989, Current Protocols in Molecular Biology, John Wiley & Sons, Inc., New York) to create blunt ended DNA fragments. The pSM1341 plasmid (FIG. 37) was treated with SalI restriction endonuclease to linearize the DNA and "end repaired" with Klenow fragment of the DNA polymerase I (Ausubel et al., supra) to create blunt ends. The pSM1341 contains the gef gene under the genetic regulatory elements $P_{lac}$/O, xylS gene which is inducible in the presence of 3-MB, and the $P_m$::lacI gene which is regulated by the XylS protein. All these genetic elements were cloned in pUC18NotI plasmid as a NotI DNA fragment. The $P_{trc}$/lacO::snuc* (blunt ended) fragment was ligated in pSM1341 plasmid at the SalI site (blunt ended), transformed into *Escherichia coli* NM522 (Invitrogen, Inc.) strain and the transformants were selected on LB agar plates (10 g bacto tryptone, 5 g yeast extract, and 10 g NaCl, 14 g bacto agar per liter) supplemented with 50 μg ampicillin (Sigma) per ml and 1 mM 3-MB (Aldrich Chemicals). The positive clones were tested by the production of a characteristic nuclease "halo" on DNAse agar plates+toluidine blue (TB) indicator dye supplemented with 40 μg ampicillin per ml. The new chimeric plasmid containing the gef and the snuc* genes was designated pNEF-1 (p=plasmid; N=staphylococcal nuclease gene; EF=gef gene; 1=clone number) (FIG. 38).

The NotI fragment from the pNEF-1 plasmid was recovered following treatment with NotI restriction endonuclease and ligated in pUTkm mini-Tn5 transposon plasmid delivery vector (Lorenzo et al., 1990, Journal of Bacteriology, 172:6568–6572) which was similarly treated with NotI restriction endonuclease followed by treatment with calf alkaline phosphatase (CAP) (Ausubel et al., supra) to prevent self-ligation of the vector during ligation process. The ligation reaction was used to transform *E. coli* CC118λ.pir strain (Lorenzo et al., supra) and the transformants were selected on LB agar plates supplemented with 40 μg kanamycin per ml and 1 mM 3-MB. The positive clones were characterized by the production of characteristic nuclease "halos" on DNAse agar plates+toluidine blue (TB) indicator dye supplemented with 40 μg kanamycin antibiotic per ml. The new chimeric plasmid is designated as pNEF-KR4.

C. Transfer of pNEF-KR4 in *P. putida* 2442 Strain

The pNEF-KR4 plasmid was transferred to *P. putida* 2442 strain for chromosomal insertion of the NotI DNA fragment consisting of the $P_{lac}$/O::gef and the $P_{trc}$/lacO::snuc* lethal genes and the regulatory elements, $P_m$::lacI, xylS, by triparental mating. In triparental mating, the *E. coli* (pRK2013) (helper plasmid) (Km$^r$, Rif$^s$; r=resistance and s=sensitivity to antibiotics), *E. coli* CC118λl18pir (pNEF-KR4) (Km$^r$, Rif$^s$), and the *P. putida* 2442 (Km$^r$, Rif$^r$) strains were "plate-mated" by overlapping streaking of the strains onto LB agar plates supplemented with 1 mM 3-MB. After overnight incubation at 30° C., the *P. putida* 2442 ex-conjugants (pNEF-KR4) (Km$^r$, Rif$^r$) were counter selected onto M9 minimal medium with sodium citrate as a sole carbon source, supplemented with 50 μg rifampicin and 50 μg kanamycin per ml and 1 mM 3-MB. The *P. putida* 2442 (pNEF-KR4) (Km$^r$, Rif$^r$) ex-conjugants were further characterized for the transfer of the snuc* gene by characterizing nuclease "halos" on DNAse agar+TB supplemented with 50 μg rifampicin and 50 μg kanamycin per ml.

A sample of *Pseudomonas putida* 2442 (pNEF-KR4) was deposited with the American Type Culture Collection (ATCC), Parklawn Drive, Rockville, Md. 20852 USA on 1 Sep. 1995 under the accession number ATCC 55705.

D. Kinetics of gef and snuc* in the Absence of 3-MB

*P. putida* 2442 (pNEF-KR4) (Km$^r$, Rif$^r$) was grown in 100 ml LB broth supplemented with 50 μg kanamycin and 50 μg rifampicin per ml and 1 mM 3-MB at 30° C. till the OD$_{450}$ reached 0.4. The cells were harvested by centrifugation at 3,500×g for 15 min and the cell pellet was washed 3 times (each time with 100 ml of LB broth) to remove 3-MB. The cell pellet was resuspended in 100 ml of LB broth and initial cell count was determined by plating an aliquot (0.1 ml) of serially diluted culture onto LB agar plates supplemented with 50 μg rifampicin, 50 μg kanamycin and 1 mM 3-MB. The culture was divided into two sterile tubes each containing 50 ml and supplemented with 50 μg rifampicin and 50 μg kanamycin. In one of the two cultures, 1 mM 3-MB was added. The cultures were transferred to a shaking (150 rpm) incubator at 30° C. To determine the efficiency of the gef and snuc* induction, viable plate counts were performed at every 2 h intervals for a total of 8 h, and 16 h later by plating an aliquot of the serial dilution of the cultures. All serial dilutions of the two cultures were plated on LB agar supplemented with 50 μg rifampicin, 50 μg kanamycin and 1 mM 3-MB. The plates were incubated at 30° C. for 36–48 h and colonies were counted and tested for the presence of snuc* gene by plating onto DNAse agar plates+toluidine blue (TB) indicator dye supplemented with 50 μg rifampicin and 50 μg kanamycin per ml.

E. Microscopic Examination of Viability and Nuclease Activity in *P. Putida* 2442 (DNEF-KR4) (Km$^r$, Rif$^r$) Grown a Culture with or without 3-MB To determine the viability of the *P. putida* 2442 (pNEF-KR4) (Km$^r$, Rif$^r$) strain without 3-MB or with 3-MB in the culture, commercially available BacLite (Molecular Probes, Inc.) nucleic acid-based fluorescent staining kit was used. Also, the intracellular snuc* activity was monitored by DAPI fluorescent staining (Hiraga et al., 1989, Journal of Bacteriology, 171:1496–1505) of the cells after 4 h of removal of 3-MB from one of the two cultures.

F. Results a. Genetic Construction of the "Dual" Conditional Lethal System

Figure 39:
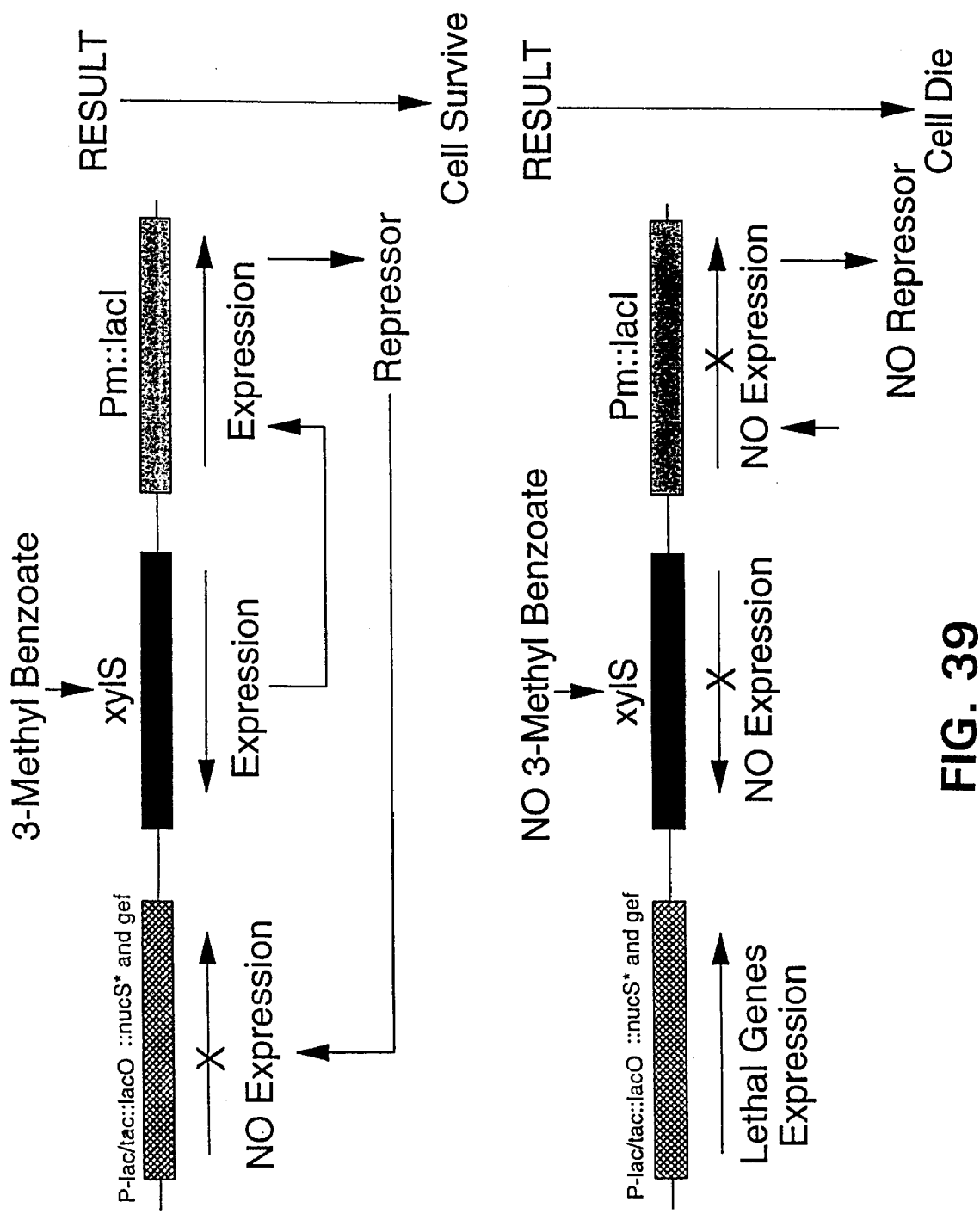
FIG. 39 illustrates the fundamental concept of a dual conditional lethal system for the containment of genetically engineered microorganisms using nucs* and gef genes under the control of a xenobiotic compound, 3-MB.

The fundamental concept of the dual conditional lethal system for the containment of genetically engineered microorganisms under the control of a xenobiotic compound, 3-MB, is schematically illustrated in FIG. 39. The characteristic nuclease "halo" production was noticed within 48 h after spreading the cells onto DNAse agar+TB without any 3-MB. The majority of the cells died except few (approximately 8–15 colonies per plate out of approximately 10$^8$ cells originally spread on the plate) slow-growing colonies with significantly reduced size which were noticed after 48–72 h of incubation at 30° C. The cells grown in the presence of 3-MB appeared as visible colonies within 24–36 h of incubation and weak nuclease halos were noticed after 4–5 days of incubation. This result suggests that the dual lethal genetic system is stable in the presence of 3-MB and these genes are well-repressed in the presence of 3-MB.

b. Transfer of pNEF-KR4 in *P. putida* 2442 Strain

For the triparental mating, the ex-conjugants were selected on M9 minimal medium with citrate as a sole carbon source which ensured the growth of only *P. putida* 2442 strain since *E. coli* cells are unable to utilize citrate as a sole carbon source. Relatively moderate numbers (20–35) of putative *P. putida* 2442 (pNEF-KR4) (Km$^r$, Rif$^r$) ex-conjugants were selected. Among them, 20% of the colonies showed characteristics nuclease halos on DNAse agar+TB supplemented with 50 μg rifampicin and 50 μg kanamycin per ml.

c. Kinetics of gef and snuc* Induction in the Absence of 3-MB

Figure 40:
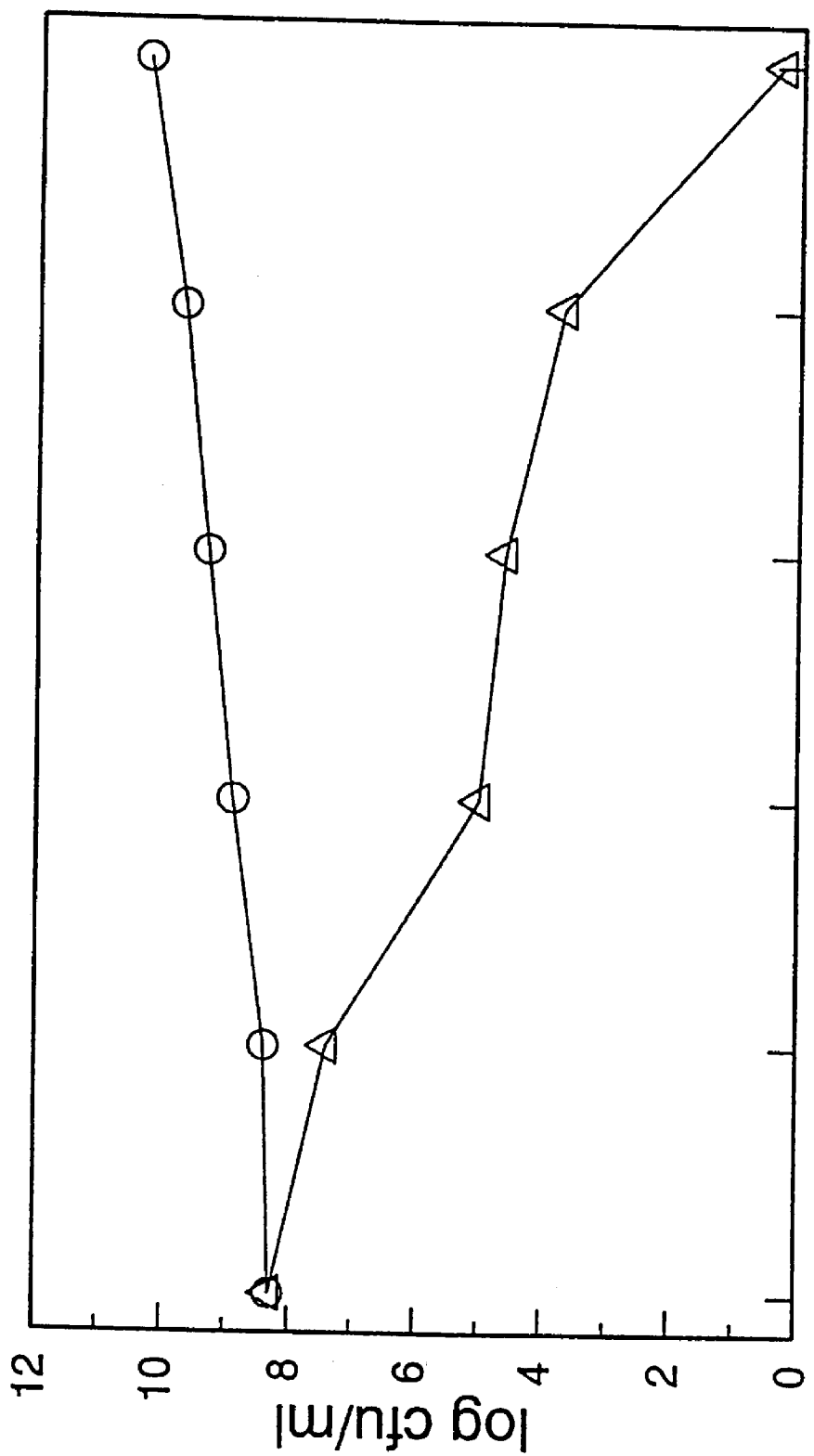
FIG. 40 illustrates the kinetics of gef and nucS* induction in *Pseudomonas putida* 2442 (pNEF-KM).

The kinetics of gef and snuc* induction is presented in Table 10 and graphically illustrated in FIG. 40. As indicated in this Table and Figure, there was a 3-fold decrease in the cells number in the culture without 3-MB within first 4 h of induction as compared to the culture which had 3-MB in it. After 8 h of incubation, another 2-fold decrease in cell number was noticed. After 16 h of incubation, only 2×10$^0$ cells per ml (plating of 0.1 ml did not show any viable colonies; however, plating 1 ml of the culture showed 2 cells on the agar plate. Therefore, a total of approximately 90 cells present in 45 ml of the culture (out of an initial cell number of 2×10$^8$) were evidenced. Recovery of these cells on LB agar supplemented with 50 μg rifampicin and 50 μg kanamycin per ml and 1 mM 3-MB was very slow (48–72 h with reduced colony size) and can be considered as an indication that the cells are physiologically debilitated. The culture with 3-MB showed increased cell growth as shown in Table 20.1 and FIG. 40. Therefore, the dual conditional lethal system under the control of 3-MB is very effective for the *P. putida* 2442 strain.

TABLE 10

Viable plate counts of the *P. putida* 2442 (pNEF-KR4) (Km$^r$, Rif$^r$) strain in the presence or absence of 3-MB

| *P. putida* 2442 (pNEF-KR4) (Km$^r$, Rif$^r$) −3 MB | | | *P. putida* 2442 (pNEF-KR4) (Km$^r$, Rif$^r$) +3 MB | | |
|---|---|---|---|---|---|
| Time | CFU/ml* | log CFU/ml | Time | CFU/ml | log CFU/ml |
| 0 h† | 2 × 10$^8$ | 8.3 | 0 h | 2 × 10$^8$ | 8.3 |
| 2 h | 3 × 10$^7$ | 7.4 | 2 h | 3 × 10$^8$ | 8.4 |
| 4 h | 1 × 10$^5$ | 5.0 | 4 h | 8 × 10$^8$ | 8.9 |
| 6 h | 4 × 10$^4$ | 4.6 | 6 h | 2 × 10$^9$ | 9.3 |
| 8 h | 5 × 10$^3$ | 3.7 | 8 h | 5 × 10$^9$ | 9.7 |
| 16 h | 2 × 10$^0$ | 0.3 | 16 h | 2 × 10$^{10}$ | 10.3 |

*colony forming unit per ml of the culture. Each data is an average of 3 studies.
†hour d. Microscopic Examination of Viability and Nuclease Activity in *P. putida* 2442 (pNEF-KR4) (Km$^r$, Rif$^r$) Grown in a Culture with 3-MB or without 3-MB In the microscopic examination using the BACLITE fluorescent stains, the cells grown without 3-MB showed reduced size with some "ghost" appearance or very poor staining with thin and slender cell morphologies as compared to the cells from the culture where 3-MB was present which were brightly stained. In this context, the term "ghost appearance" indicates an altered cell morphology where most of the intracellular material condensed in zones, leaving the rest of the cell transparent. This result suggests that the absence of 3-MB activates the lethal genes and causes death to the host cells.

The DAPI stain showed significantly reduced fluorescence for the cells in which 3-MB was not added as compared to the cells in which the culture was supplemented with 3-MB. This result suggests that the absence of 3-MB de-repressed the snuc* gene resulting in the destruction of the cellular nucleic acids.

e. Discussion

The dual conditional lethal system using gef and the snuc* genes under the regulatory genetic elements that were controlled by 3-MB showed significant decrease in cell numbers within 4–16 h period of time. The system was stable in the presence of 3-MB and well-regulated as evidenced by the stable cell counts. The activation of the gef gene in the absence of 3-MB was visualized under microscope by "ghost" cell morphologies. The de-repression of the snuc* and its intracellular activity was evidenced by significant reduction of the fluorescent dye incorporation due to the destruction of the cellular nucleic acids. The results show promise of dual conditional lethal systems for genetically engineered microorganisms under the control of a xenobiotic compound.

REFERENCES

1. Akimoto S., K. Ono and Y. Ohnishi, 1986, FEMS Microbiol. Letters, 33:241–245.
2. Amann E., J. Brosius and M. Ptashne, 1983, Gene, 25:167–178.
3. Ausubel F. M., R. Brent, R. E. Kingston, D. D. Moore, J. in Molecular Biology. John Wiley & Sons, Inc., New York.
4. Bachmann B. J, 1987, In *Escherichia coli* and *Salmonella typhimurium* ed. Neidhard, F. C., et al., ASM, pp. 1190–1219.

5. Bech F., S. T. Jorgensen, B. Diderichsen and O. H. Carlstrdm, 1985, Embo, 4:1059–1066.
6. Birnboim H. C. and J. Doly, 1979, Nucleic Acid Research, 7:1513–1523.
7. Bolivar F, 1978, Gene, 4:121–136.
8. Boros, 1984, Gene, 30:257–260.
9. Boyer, et al., 1969, J. Mol. Biol., 41:459.
10. Bradford, 1976, Anal. Biochem. 72:248–254.
11. Brosius J., A. Ullrich, M. A. Raker, A. Gray, T. J. Dull, R. R. Gutell and H. F. Noller., 1981, Plasmid, 6:112–118.
12. Brosius, J. and A. Adriana, 1984, Proc. Natl. Acad. Sci. U.S.A., 81:6929–6933.
13. Chang A. C. Y. and S. N. Xohen, 1978, J. Bacteriology, 134:1141–1156.
14. Csonka, L. N. and A. J. Clark, 1979, Genetics, 93:321–343.
15. de Lorenzo V., M. Herrero, U. Jakubzik and K. N. Timmis, 1990, Journal of Bacteriology. 172:6568–6572.
16. Eberl, et al., 1992, Molec. Microbiol., 6 (14):1969–1979.
17. Gerdes K., P. B. Rasmussen and S. Molin, 1986, Proc. Natl. Acad. Sci USA, 83:3316–3320.
18. Gerlitz, et al., 1990, J.Bacteriol., 172:6194–6203.
19. Givskov and Molin, 1988, J.Bacteriol., 170:5855–5862.
20. Grinter, et al., 1989, Plasmid, 22:203–214.
21. Herrero, et al., 1990, J.Bacteriol., 172:6557–6567.
22. Hiraga S., H. Niki, T. Ogura, C. Ichinose, H, Mori, B. Ezaki and A. Jaffe, 1989, Journal of Bacteriology, 171:1496–1505.
23. Humphreys G. O., G. A. Willahaw, H. R. Smith and E. S. Anderson, 1976, Mol. Gen. Genet., 145:101–108.
24. Lanzer, et al., 1988, Proc. Natl. Acad. Sci., USA, 85:8973–8977.
25. Maniatis et al., 1982, Molecular cloning: A Laboratory Manual, Cold Spring Harbor Laboratory Press, New York.
26. Muller-Hill, 1975, Prog. Biophys. Molec. Biol., 30:227–252.
27. Nielsson, et al., 1983, Nucl. Acid Res., 11:8019–8030.
28. Ono K., S. Akimoto and Y. Ohnishi, 1987, Microbiol. Immunol., 31:1071–1083.
29. Paulsen, L. K. N. W. Larsen, S. Molin and P. Andersson, 1989, Molecular Microbiology, 3:1463–1472.
30. Poulsen L. K., A. Refn, S. Molin and P. Andersson, 1991, Molecular Microbiology, 5:1639–1648.
31. Roberts, et al., 1990, J.Bacteriol., 172:6204–6216.
32. Sakikawa T., S. Akimoto and Y. Ohnishi, 1989, Biochim. Biophys. Acta, 1007:158–166.
33. Sanger, et al, 1977, Proc. Natl. Acad. Sri. USA, 74:5463–5467.
34. Schneider, et al., 1987, Meth. Enzymol., 153:452–461.
35. Shortle D. and D. Bottstein, 1983, Gene, 22:181–189.
36. Silhavy et al., 1984, Experiments with Gene Fusions, Cold Spring Harbour Laboratory, New York, pp. xi–xii.
37. Simon R., U. Priefer and A. Puhler, 1983, Biotechnology, 1:784–790.
38. Squires C. A. Krainer, G. Barry, W. F. Chen and C. L. Squires, 1981, Nucleic Acid Res., 9:6827–6839.
39. Stark M. J. R., 1987, Gene, 51:255–267.
40. Tucker, et al., 1979, Molecular and Cellular Biochemistry, 23:131–141.
41. WO 86/06743 (Molin, et al.)
42. Yanisch-Perron, et al., 1985, Gene, 33:103–109.

---

We claim:

1. A microbial cell containing a gene whose expression results in the formation of an enzyme which is present and hydrolytically active in the cytoplasm of said cell, the cell further containing a regulatory nucleotide sequence which regulates the expression of the gene, the expression of said gene leading to formation of the enzyme in the cell at a rate which results in the hydrolysis of hydrolysable cytoplasmic substances necessary for non-limited function of the cell, to an extent whereby the function of the cell is being limited.

2. A cell according to claim 1 wherein the enzyme is selected from the group consisting of a nuclease, a phospholipase, a lipase, a lysozyme, a protease, and a carbohydrase.

3. A cell according to claim 1 wherein the expression of the gene results in the formation of a nuclease which hydrolyses diesterphosphate bonds in nucleic acids in the cell, the expression of said gene leading to formation of the nuclease in the cell at a rate which results in the presence of nicks in one strand of the cell nucleic acids to an extent which cannot be repaired by the nucleic acid repair mechanism of the cell, thereby limiting the function of said cell.

4. A cell according to claim 1 wherein the gene whose expression results in the formation of a hydrolytically active enzyme is contained in a recombinant replicon or recombinant replicons.

5. A cell according to claim 4 wherein the regulatory sequence is contained in a recombinant replicon or recombinant replicons.

6. A cell according to claim 1 wherein the gene whose expression results in the formation of a hydrolytically active enzyme is a gene lacking a sequence coding for a peptide signal sequence which, if present, would have permitted the enzyme to be transported through the cell membrane.

7. A cell according to claim 1 wherein the regulatory nucleotide sequence contains a regulatable promoter operably linked to the gene encoding the hydrolytically active enzyme.

8. A cell according to claim 7 wherein the regulatable promoter is regulated by a factor selected from the environmental conditions of the cell, the physiological state of the cell and a stochastic event.

9. A cell according to claim 8 wherein the regulatable promoter is regulated by a factor selected from the physical conditions in the environment and the presence or absence of a certain chemical in the environment.

10. A cell according to claim 9 wherein the chemical is isopropyl-beta-D-thiogalactopyranoside (IPTG).

11. A cell according to claim 1 wherein the expression of the gene whose expression results in the formation of a hydrolytically active enzyme is stochastically induced as a result of a recombinational excision of an excisable negatively functioning regulatory nucleotide sequence being operably linked to said gene which nucleotide sequence, while present in the cell, inhibits expression of the gene whose expression results in the formation of the hydrolytically active enzyme.

12. A cell according to claim 11 wherein said excisable negatively functioning regulatory nucleotide sequence is a sequence which is flanked by a first flanking sequence and a second flanking sequence substantially homologous with said first flanking sequence whereby said regulatory element is recombinationally excisable in the cell.

13. A cell according to claim 12 wherein the gene whose expression results in the formation of a hydrolytically active enzyme encodes a first RNA which is a messenger RNA, and the excisable negatively functioning regulatory nucleotide sequence being operably linked to said gene, is a gene encoding a second RNA which forms an RNA-RNA duplex with said first messenger RNA and thereby, when it is expressed, inhibits translation of said gene coding for the hydrolytically active enzyme.

14. A cell according to claim 12 wherein the excisable negatively functioning regulatory nucleotide sequence is a gene encoding a polypeptide repressor of transcription of the gene whose expression results in the formation of a hydrolytically active enzyme.

15. A cell according to claim 14 wherein the excisable negatively functioning regulatory nucleotide sequence is a gene encoding a lac repressor, and the gene whose expression results in the formation of a hydrolytically active enzyme is operably linked to the lac promoter, said lac promoter including the operator site for the lac repressor.

16. A cell according to claim 12 wherein the negatively functioning regulatory nucleotide sequence is a termination sequence preventing transcription of the gene whose expression results in the formation of a hydrolytically active enzyme.

17. A cell according to claim 1 wherein the expression of the gene whose expression results in the formation of a hydrolytically active enzyme is stochastically induced as a result of a site-specific recombinational excision of an excisable negatively functioning regulatory nucleotide sequence being operably linked to said gene which nucleotide sequence, while present in the cell, inhibits expression of the gene whose expression results in the formation of the hydrolytically active enzyme.

18. A cell according to claim 17 wherein said excisable negatively functioning regulatory nucleotide sequence is a sequence which is flanked by a first site for site-specific resolution and a second site for site-specific resolution, the second site being resolvable by the same or a functionally equivalent multimer resolving enzyme as is the first site, whereby said regulatory element is recombinationally excisable in the cell.

19. A cell according to claim 17 wherein the first and second site for site-specific resolution is the mrs site derived from plasmid RP4.

20. A cell according to claim 17 wherein the gene whose expression results in the formation of a hydrolytically active enzyme encodes a first messenger RNA, and the excisable negatively functioning regulatory nucleotide sequence being operably linked to said gene, is a gene encoding a second messenger RNA which forms an RNA-RNA duplex with said first messenger RNA and thereby, when it is expressed, inhibits translation of said gene coding for the hydrolytically active enzyme.

21. A cell according to claim 17 wherein the excisable negatively functioning regulatory nucleotide sequence is a gene encoding a polypeptide repressor of transcription of the gene whose expression results in the formation of a hydrolytically active enzyme.

22. A cell according to claim 21 wherein the excisable negatively functioning regulatory nucleotide sequence is a gene encoding a lac repressor, and the gene whose expression results in the formation of a hydrolytically active enzyme is operably linked to the lac promoter, said lac promoter including the operator site for the lac repressor.

23. A cell according to claim 17 wherein the negatively functioning regulatory nucleotide sequence is a termination sequence preventing transcription of the gene whose expression results in the formation of a hydrolytically active enzyme.

24. A cell according to claim 1 wherein the gene whose expression results in the formation of a hydrolytically active enzyme is stochastically expressed as a result of recombinational inversion of an invertible promoter sequence of said regulatory nucleotide sequence said promoter being operably linked to the gene.

25. A cell according to claim 1 wherein the gene whose expression results in the formation of a hydrolytically active enzyme is a gene which is derived from a bacterial replicon.

26. A cell according to claim 1 wherein the hydrolytically active enzyme is encoded by a gene derived from a Serratia species.

27. A cell according to claim 26 wherein the gene is derived from a Serratia species selected from the group consisting of S. liquefaciens and S. marcescens.

28. A cell according to claim 27 wherein the enzyme is an endonuclease encoded by a gene having the following DNA sequence (SEQ ID NO:1).

29. A cell according to claim 27 wherein the enzyme is a phospholipase encoded by a gene having the following DNA sequence (SEQ ID NO:2).

30. A cell according to claim 25 wherein the gene is derived from *Staphylococcus aureus*.

31. A cell according to claim 1 wherein at least one of the genes whose expression results in the formation of a hydrolytically active enzyme and the nucleotide sequence regulating said gene is truncated and/or mutated at one or more sites, whereby the cell function-limiting effect of the enzyme encoded by the gene, when expressed in the cell is the same or increased relative to the cell function-limiting effect of the enzyme expressed in a cell containing said gene and said nucleotide sequence in non-truncated or non-mutated form.

32. A cell according to claim 31 wherein the cell contains a gene coding for an endonuclease.

33. A cell according to claim 32 wherein the gene is derived from a Serratia species.

34. A cell according to claim 1 which comprises a further regulatably expressible gene which encodes a cell function-limiting gene product.

35. A cell according to claim 34 wherein the further regulatably expressible gene is regulated by a regulatory nucleotide sequence of the same type as the sequence regulating the gene whose expression results in the formation of a hydrolytically active enzyme.

36. A cell according to claim 34 wherein the further regulatably expressible gene is regulated by a regulatory nucleotide sequence of another type than the sequence regulating the gene whose expression results in the formation of a hydrolytically active enzyme, said other type being a regulatory nucleotide sequence which regulates the gene whose expression results in the formation of the hydrolytically active enzyme.

37. A cell according to claim 34 wherein the further regulatably expressible gene is the hok gene from the parB region of plasmid R1 or a DNA sequence which is functionally homologous to the R1 hok gene.

38. A cell according to claim 34 wherein the further regulatably expressible gene is the gef gene.

39. A cell according to claim 1 which further comprises a DNA sequence not naturally related to the replicon carrying the gene whose expression results in the formation of a hydrolytically active enzyme or the replicon carrying the regulatory nucleotide sequence, said DNA sequence being selected from the group consisting of a sequence coding for a pesticidally active gene product and a sequence coding for a pollutant-degrading gene product.

40. A cell according to claim 1 which is a cell transformed with a recombinant replicon or recombinant replicons containing a gene whose expression results in the formation of an enzyme which is present and hydrolytically active in the cytoplasm of said cell, the expression of said gene leading to formation of the enzyme in the cell at a rate which results in the hydrolysis of hydrolysable cytoplasmic substances necessary for non-limited function of the cell, to an extent whereby the function of the cell is limited, the expression of said gene being regulated by a regulatory nucleotide sequence which is contained in the recombinant replicon containing the gene or in another recombinant replicon present in the transformed cell.

41. A recombinant replicon containing a regulatably expressible gene which, when expressed in a microbial cell encodes an enzyme which is present and hydrolytically active in the cytoplasm of the cell, the expression of said gene leading to formation of the enzyme in the cell at a rate which results in the hydrolysis of hydrolysable cytoplasmic substances necessary for non-limited function of the cell, to an extent whereby the function of the cell is being limited, the expression of said genes being regulated by a regulatory nucleotide sequence which is contained in the recombinant replicon or in another recombinant replicon present in a cell containing the replicon.

42. A recombinant replicon according to claim 41 which contains the regulatory nucleotide sequence.

43. A replicon according to claim 41 wherein the hydrolytically active enzyme is an enzyme which, when the replicon is expressed in a cell, is retained in the cell.

44. A replicon according to claim 43 wherein the enzyme being encoded is a phospholipase.

45. A replicon according to claim 41 wherein the expression of the gene results in the formation of a nuclease which hydrolyses diesterphosphate bonds in nucleic acids in the cell, the expression of said gene leading to formation of the nuclease in the cell at a rate which results in the presence of nicks in one strand of the cell nucleic acids to an extent which cannot be repaired by the nucleic acid repair mechanism of the cell, thereby limiting the function of said cell.

46. A replicon according to claim 41 wherein the gene encoding the hydrolytically active enzyme is a gene lacking a sequence coding for a peptide signal sequence which, if present, would have permitted the enzyme to be transported through the cell membrane.

47. A replicon according to claims 41 wherein the regulatory nucleotide sequence contains a regulatable promoter operably linked to the gene encoding the hydrolytically active enzyme.

48. A replicon according to claim 41 wherein the expression of the gene coding for the hydrolytically active enzyme is stochastically induced as a result of a recombinational excision of an excisable negatively functioning regulatory nucleotide sequence which, while present in the cell, inhibits expression of the gene coding for the hydrolytically active enzyme.

49. A replicon according to claim 48 wherein said excisable negatively functioning regulatory nucleotide sequence is a sequence flanked by a first flanking sequence and a second flanking sequence substantially homologous with said first flanking sequence whereby said regulatory element is recombinationally excisable in the cell.

50. A replicon according to claim 48 wherein the gene coding for the hydrolytically active enzyme encodes a first RNA which is a messenger RNA, and the excisable negatively functioning regulatory nucleotide sequence is a gene encoding a second RNA which forms an RNA-RNA duplex with said first messenger RNA and thereby inhibits translation thereof.

51. A replicon according to claim 48 wherein the negatively functioning regulatory nucleotide sequence is a gene encoding a polypeptide repressor of transcription of the gene coding for the hydrolytically active enzyme.

52. A replicon according to claim 51 wherein the negatively functioning regulatory nucleotide sequence is a gene encoding the lac repressor, and the gene coding for the hydrolytically active enzyme is operably linked to the lac promoter, said lac promoter including the operator site for said lac repressor.

53. A replicon according to claim 48 wherein the negatively functioning regulatory nucleotide sequence is a termination sequence preventing transcription of the gene coding for the hydrolytically active enzyme.

54. A replicon according to claim 41 wherein the expression of the gene whose expression results in the formation of a hydrolytically active enzyme is stochastically induced as a result of a site-specific recombinational excision of an excisable negatively functioning regulatory nucleotide sequence being operably linked to said gene which nucleotide sequence, while present in the cell, inhibits expression of the gene whose expression results in the formation of the hydrolytically active enzyme.

55. A replicon according to claim 54 wherein said excisable negatively functioning regulatory nucleotide sequence is a sequence which is flanked by a first site for site-specific resolution and a second site for site-specific resolution, the second site being resolvable by the same or a functionally equivalent multimer resolving enzyme as is the first site, whereby said regulatory element is recombinationally excisable in the cell.

56. A replicon according to claim 54 wherein the gene whose expression results in the formation of a hydrolytically active enzyme encodes a first RNA which is a messenger RNA, and the excisable negatively functioning regulatory nucleotide sequence being operably linked to said gene, is a gene encoding a second RNA which forms an RNA-RNA duplex with said first messenger RNA and thereby, when it is expressed, inhibits translation of said gene coding for the hydrolytically active enzyme.

57. A replicon according to claim 54 wherein the excisable negatively functioning regulatory nucleotide sequence is a gene encoding a polypeptide repressor of transcription of the gene whose expression results in the formation of a hydrolytically active enzyme.

58. A replicon according to claim 54 wherein the negatively functioning regulatory nucleotide sequence is a termination sequence preventing transcription of the gene whose expression results in the formation of a hydrolytically active enzyme.

59. A replicon according to claim 41 wherein the gene coding for the hydrolytically active enzyme is stochastically expressed as a result of recombinational inversion of an invertible promoter sequence of said regulatory nucleotide sequence said promoter being operably linked to the gene coding for the enzyme.

60. A replicon according to claim 41 wherein the gene coding for the hydrolytically active enzyme is derived from a bacterial replicon.

61. A replicon according to claim 60 wherein the hydrolytically active enzyme is encoded by a gene derived from a Serratia species.

62. A replicon according to claim 61 wherein the gene is derived from a Serratia species selected from the group consisting of *S. liquefaciens* and *S. marcescens*.

63. A replicon according to claim 62 wherein the hydrolytically active enzyme is an endonuclease encoded by a gene having the following DNA sequence (SEQ ID NO:1).

64. A replicon according to claim 62 wherein the hydrolytically active enzyme is a phospholipase encoded by a gene having the following DNA sequence (SEQ ID NO:2).

65. A replicon according to claim 60 wherein the gene is a gene derived from *Staphylococcus aureus*.

66. A replicon according to claim 41 wherein the gene coding for the hydrolytically active enzyme or the nucleotide sequence regulating said gene is truncated or mutated at one or more sites, whereby the cell function-limiting effect of the enzyme encoded by the gene, when expressed in the cell is the same or increased relative to the cell function-limiting effect of the enzyme expressed in a cell not containing truncated and/or mutated DNA.

67. A replicon according to claim 66 wherein gene coding for the hydrolytically active enzyme is a gene coding for an endonuclease.

68. A replicon according to claim 67 wherein the gene coding for an endonuclease is a gene derived from a Serratia species.

69. A replicon according to claim 41 which is a replicon comprising a further regulatably expressible gene encoding a cell function-limiting function.

70. A replicon according to claim 69 wherein the further regulatably expressible gene is the hok gene from the parB region of plasmid R1 or a DNA sequence which is functionally homologous to the R1 hok gene.

71. A replicon according to claim 69 wherein the further regulatably expressible gene is the gef gene.

72. A replicon according to claim 41, which is a replicon further comprising a DNA sequence not naturally related to the replicon carrying the gene coding for the hydrolytically active enzyme or the replicon carrying the regulatory nucleotide sequence, said DNA sequence being selected from the group consisting of a pesticidally active gene product and a sequence coding for a pollutant-degrading gene product.

73. A population of cells consisting of a multiplicity of cells as defined in claim 1, said cells containing a gene whose expression results in the formation of an enzyme which is present and hydrolytically active in the cytoplasm of said cells, the cells further containing a regulatory nucleotide sequence which regulates the expression of said gene, the expression of said gene leading to formation of the enzyme in the cells at a rate which results in the hydrolysis of hydrolysable cytoplasmic substances necessary for non-limited function of the cells, to an extent whereby the function of the cells is being limited.

74. A cell population according to claim 73 comprising cells transformed with a recombinant replicon, said replicon which replicates in said cells.

75. A cell population according to claim 73 wherein the cells are bacterial cells.

76. A cell population according to claim 73 wherein the expression of the gene coding for the function-limiting enzyme is regulatable by a repressor substance which can undergo a decay when said cells are released to the outer environment to an extent whereby the repressor substance is converted to a non-functional form, said repressor substance being present in the cells of the population in different amounts whereby as a result of said linear decay, the function of the cells of the population will be gradually limited.

77. A method of limiting the survival of a microbial cell population in a first or a second environment which method comprises transforming the cells of said population with a recombinant replicon being replicated in the cells of the population and containing a gene whose expression results in the formation of an enzyme which is present and hydrolytically active in the cytoplasm of said cell, the cells further containing a regulatory nucleotide sequence being regulatable by an environmental factor and which regulates the expression of said gene, the expression of said gene leading to formation of the enzyme in the cells at a rate which results in the hydrolysis of hydrolysable cytoplasmic substances necessary for non-limited function of the cell, to an extent whereby the function of the cells is being limited leading to a limitation of the survival of the cell population.

78. A method according to claim 77 wherein the cells of said population contain a gene whose expression results in the formation of an enzyme which is present and hydrolytically active in the cytoplasm of said cell, the cells further containing a regulatory nucleotide sequence which regulates the expression of the gene, the expression of said gene leading to formation of the enzyme in the cells at a rate which results in the hydrolysis of hydrolysable cytoplasmic substances necessary for non-limited function of the cell, to an extent whereby the function of the cells is being limited.

79. A method according to claim 77 wherein the survival of the cell population is limited in a first environment in which the gene is expressed, said cell population thereby being contained in said first environment.

80. A method according to claim 77 wherein the survival of the cell population is not limited when present in a first environment, which first environment could change to a second environment physically or chemically distinct from the first environment, in which first environment the gene whose expression results in the formation of a hydrolytically active enzyme is not expressed, but the survival of which cell population is limited when transferred to a second environment or when present in a physically or chemically changed first environment, where the gene is expressed.

81. A method according to claim 77 wherein the survival of a cell population is being limited by providing in the cells a gene coding for the hydrolytically active enzyme which is operably linked to a regulatory nucleotide sequence encoding a repressor substance which can undergo a decay when said cells are released to a human or animal body or the outer environment to an extent whereby the repressor substance is converted to a non-functional form, said repressor substance being present in the cells of the population in different amounts whereby as a result of said decay, the function of the cells of the population will be gradually be limited.

82. A method of containing an extrachromosomal recombinant replicon to a first kind of microbial cell, where said replicon is naturally transferable to a second kind of microbial cell, which method comprises providing on the recombinant extrachromosomal replicon a gene whose expression results in the formation of an enzyme which is present and hydrolytically active in the cytoplasm of a cell, the formation of said enzyme being at a rate which results in the hydrolysis of hydrolysable cytoplasmic substances necessary for non-limited function of the cell, to an extent whereby the function of the cell is being limited, said first kind of cells having or being modified to have a chromosomal replicon comprising a regulatory nucleotide sequence which inhibits the expression of said gene and thereby protects said first kind of cells, said regulatory gene being lacking in said second kind of cell, whereby, if a cell of the second kind receives said extrachromosomal recombinant replicon said gene is expressed and has a function-limiting effect thereon.

83. A method according to claim 81 wherein the recombinant replicon is a replicon which does not contain a regulatory nucleotide sequence.

84. A method according to claim 82 wherein the expression of the gene whose expression results in the formation of a hydrolytically active enzyme, results in the formation of an endonuclease which hydrolyses diesterphosphate bonds in nucleic acids in the cell, the expression of said gene leading to formation of the endonuclease in the cell at a rate which results in the presence of nicks in the cell nucleic acids to an extent which cannot be repaired by the nucleic acid repair mechanism of the cells, thereby limiting the function of said cell.

85. A method of stochastically limiting the survival of a microbial cell population which comprises transforming the cells thereof with a recombinant replicon containing a regulatably expressible gene which, when expressed in a cell encodes an enzyme which is present and hydrolytically active in the cytoplasm of the cell, the expression of said gene leading to formation of the enzyme in the cell at a rate which results in the hydrolysis of hydrolysable cytoplasmic substances necessary for non-limited function of the cells, to an extent whereby the function of the cells is being limited, the expression of said genes or genes being stochastically induced as a result of recombinational excision of an excisable negatively functioning regulatory nucleotide sequence which, while present in the cells, inhibits expression of the gene coding for the enzyme, said negatively functioning regulatory nucleotide sequence being contained in the recombinant replicon or in an other recombinant replicon present in cells of the population containing the replicon.

86. A method according to claim 85 wherein the recombinant replicon is a replicon wherein the expression of the gene coding for the hydrolytically active enzyme is stochastically induced as a result of a recombinational excision of an excisable negatively functioning regulatory nucleotide sequence which, while present in the cell, inhibits expression of the gene coding for the hydrolytically active enzyme and wherein said excisable negatively functioning regulatory nucleotide sequence is a sequence flanked by a first flanking sequence and a second flanking sequence substantially homologous with said first flanking sequence whereby said regulatory element is recombinationally excisable in the cell.

87. A method of stochastically limiting the survival of a microbial cell population which comprises transforming the cells thereof with a recombinant replicon containing a regulatably expressible gene which, when expressed in a cell encodes an enzyme which is present and hydrolytically active in the cytoplasm of the cell, the expression of said gene leading to formation of the enzyme in the cell at a rate which results in the hydrolysis of hydrolysable cytoplasmic substances necessary for non-limited function of the cells, to an extent whereby the function of the cells is being limited, the expression of said gene being stochastically induced as a result of a site-specific recombinational excision of an excisable negatively functioning regulatory nucleotide sequence which, while present in the cells, inhibits expression of the gene coding for the enzyme, said negatively functioning regulatory nucleotide sequence being contained in the recombinant replicon or in an other recombinant replicon present in cells of the population containing the replicon.

88. A method according to claim 87 wherein the recombinant replicon is a replicon wherein the expression of the gene whose expression results in the formation of a hydrolytically active enzyme is stochastically induced as a result of a site-specific recombinational excision of an excisable negatively functioning regulatory nucleotide sequence being operably linked to said gene which nucleotide sequence, while present in the cell, inhibits expression of the gene whose expression results in the formation of the hydrolytically active enzyme and wherein said excisable negatively functioning regulatory nucleotide sequence is a sequence which is flanked by a first site for site-specific resolution and a second site for site-specific resolution, the second site being resolvable by the same or a functionally equivalent multimer resolving enzyme as is the first site, whereby said regulatory element is recombinationally excisable in the cell.

89. A method of stochastically limiting the survival of a microbial cell population which comprises transforming the cells thereof with a recombinant replicon containing a regulatably expressible gene which, when expressed in the cells of the population encodes an enzyme not being transportable over the cell membrane of said cells, and which is hydrolytically active in the cytoplasm of the cells, the expression of said gene leading to formation of the enzyme in the cells at a rate which results in the hydrolysis of hydrolysable cytoplasmic substances necessary for non-limited function of the cells, to an extent whereby the function of the cells is being limited, the expression of said gene being stochastically expressed as a result of recombinational inversion of an invertible promoter sequence of said regulatory nucleotide sequence, said promoter being operably linked to the gene coding for the enzyme which, while present in the cells, inhibits expression of the gene coding for the enzyme, said regulatory nucleotide sequence being contained in the recombinant replicon or in an other recombinant replicon present in a cells containing the replicon.

90. A method according to claim 89 wherein the promoter sequence is a sequence carrying the fimA promoter or functional homologue thereof.

91. A pesticidally active composition which contains a viable microbial cell population as defined in claim 73 wherein the cells contain a further DNA sequence not naturally related to the gene coding for the hydrolytically active enzyme or to the regulatory nucleotide sequence, which further sequence is a sequence coding for a pesticidally active gene product, the cells being function-limited to an extent which, when the composition is administered to an environment containing a pest, allows the cells to express the pesticidally active gene product for a period of time and in an amount sufficient to obtain an effective pesticidal effect in said environment but which does not allow the cells to persist in the environment.

92. A composition according to claim 91 wherein the further DNA sequence codes for a gene product which is toxic for insects or their progeny.

93. A composition according to claim 92 wherein the further DNA sequence is a sequence derived from a strain of *Bacillus thuringiensis* encoding an insecticidal protein.

94. An environmental pollutant-degrading composition which contains a viable microbial cell population as defined in claim 73 wherein the cells contains a further DNA sequence not naturally related to the gene coding for the hydrolytically active enzyme or to the regulatory nucleotide sequence, which further sequence is a sequence coding for an environmental pollutant-degrading gene product, the cells being function-limited to an extent which, when the composition is administered to an environment containing a pollutant to be degraded, allows the cells to express said pollutant degrading gene product for a period of time and in an amount sufficient to obtain an effective pollutant-degrading effect in said environment but which does not allow The cells to persist in the environment.

95. A composition according to claim 94 wherein the gene or genes the expression of which results in the formation of a cell function-limiting enzyme is only expressed when the pollutant degradable by the pollutant-degrading gene product is substantially degraded.

96. A cell according to claim 31 wherein the truncated or mutated gene is derived from a Staphylococcus spp.

97. A cell according to claim 96 wherein the truncated or mutated gene is a Staphylococcus spp gene coding for a mutant nuclease.

98. A cell according to claim 97 wherein the truncated or mutated nuclease is selected from nucleases encoded by pSNUC24-26 and pSNUC420-26.

99. A cell according to claim 96 wherein the gene whose expression results in the formation of a truncated or mutated *Staphylococcus aureus* nuclease is derived from *Staphylococcus aureus* (Foggi) ATCC 27355.

100. A cell according to claim 99 wherein the expression of the gene results in the formation of a truncated nuclease.

101. A cell according to claim 100 wherein the truncated nuclease lacks at least 9 amino acid residues of those of the parent enzyme.

102. A cell according to claim 99 wherein the nuclease is encoded by the DNA sequence of FIG. 32 (SEQ ID NO:7).

103. A cell according to claim 34, wherein the further regulatably expressible gene is the *E. coli* xth gene encoding exonuclease III.

104. A replicon according to claim 66 wherein the truncated or mutated gene is derived from a Staphylococcus spp.

105. A replicon according to claim 104 wherein the truncated or mutated gene is a Staphylococcus spp gene coding for a mutant nuclease.

106. A replicon according to claim 105 wherein the truncated or mutated nuclease is selected from nucleases encoded by pSNUC24-26 and pSNUC420-26.

107. A cell according to claim 1 wherein the regulatory nucleotide sequence which regulates the expression of the gene is regulated by the presence or absence of a xenobiotic compound.

108. A cell according to claim 107 wherein the xenobiotic compound is 3-methyl benzoate.

109. A cell according to claim 107 wherein the regulatory nucleotide sequence comprises the xylS gene.

110. A cell according to claim 109 which further comprises the $P_m$::lacI gene.

111. A cell according to claim 107 which comprises a further regulatably expressible gene which encodes a cell function-limiting gene product.

112. A cell according to claim 111 in which the further regulatably expressible gene is selected from the group consisting of the gef, hok and xth genes.

113. A cell according to claim 107 wherein the gene whose expression results in the formation of a hydrolytically active enzyme is truncated or mutated at one or more sites, whereby the cell function-limiting effect of the enzyme encoded by the gene, when expressed in the cell is the same or increased relative to the cell function-limiting effect of the enzyme expressed in a cell containing said gene and said nucleotide sequence in non-truncated or non-mutated form.

114. A cell according to claim 113 wherein the truncated and/or mutated gene is derived from a Staphylococcus spp.

115. A cell according to claim 114 wherein the truncated or mutated gene is a Staphylococcus spp gene coding for a mutant nuclease.

116. A cell according to claim 115 wherein the truncated or mutated nuclease is selected from nucleases encoded by pSNUC24-26 and pSNUC420-26.

117. A cell according to claim 114 wherein the gene whose expression results in the formation of a truncated or mutated *Staphylococcus aureus* nuclease is derived from *Staphylococcus aureus* (Foggi) ATCC 27355.

118. A cell according to claim 117 wherein the expression of the gene results in the formation of a truncated nuclease.

119. A cell according to claim 118 wherein the truncated nuclease lacks at least 9 amino acid residues of those of the parent enzyme.

120. A cell according to claim 117 wherein the nuclease is encoded by the DNA sequence of FIG. 32 (SEQ ID NO:7).

121. A population of cells consisting of a multiplicity of cells as defined in claim 107.

122. A recombinant replicon according to claim 41 wherein the regulatory nucleotide sequence is regulated by the presence or absence of a xenobiotic compound.

123. A method according to claim 77 wherein the regulatory nucleotide sequence being regulatable by an environmental factor is regulated by the presence or absence of a xenobiotic compound.

124. A method according to claim 82 wherein the regulatory nucleotide sequence is regulated by the absence or presence of a xenobiotic compound.

125. A composition which comprises the cell population of claim 107.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 743 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CGGCCGACAC   GCTCGAATCC   ATCGACAACT   GCGCGGTCGG   CTGCCCGACC   GGCGGCAGCA      60

GCAACGTGTC   TATCGTGCGC   CATGCTTATA   CGTTGAACAA   CAACAGCACC   ACCAAGTTCG     120

CCAACTGGGT   GGCCTATCAC   ATCACCAAAG   ACACGCCGGC   CAGCGGCAAG   ACGCGCAACT     180

GGAAAACCGA   TCCGGCTCTC   AATCCGGCGG   ACACTCTGGC   GCCCGCCGAT   TACACCGGTG     240

CCAACGCCGC   GCTGAAGGTC   GATCGCGGTC   ATCAGGCGCC   GCTGGCCTCG   CTGGCGGGCG     300

TTTCCGACTG   GGAATCGTTG   AACTACCTGT   CCAACATCAC   GCCGCAAAAG   TCCGATCTGA     360

ACCAGGGCGC   CTGGGCTCGG   CTGGAAGATC   AGGAACGCAA   GCTGATCGAT   CGCGCCGATA     420

TCTCCTCGGT   CTATACCGTG   ACCGGGCCGC   TGTATGAGCG   CGATATGGGC   AAACTGCCGG     480

GCACCCAGAA   AGCGCACACC   ATCCCCAGCG   CCTACTGGAA   GGTAATTTTC   ATCAACAACA     540

GCCCGGCGGT   GAACCACTAT   GCCGCCTTCC   TGTTCGACCA   GAACACGCCG   AAGGGCGCCG     600
```

| ATTTCTGCCA | ATTCCGCGTG | ACGGTGGACG | AGATCGAGAA | ACGCACCGGC | CTGATCATCT | 660 |
| GGGCCGGTCT | GCCGGACGAC | GTGCAGGCTT | CGCTGAAGAG | CAAACCGGGC | GTTCTGCCGG | 720 |
| AGTTGATGGG | CTCCTGCCGG | AGT | | | | 743 |

( 2 ) INFORMATION FOR SEQ ID NO:2:

( i ) SEQUENCE CHARACTERISTICS:
        ( A ) LENGTH: 957 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

| ATGAGTATGC | CTTTAAGTTT | TACCTCTGCA | GTATCCCCGG | TGGCCGCGAT | CCCTACGCCT | 60 |
| CGCGCCGCTG | CCGAGACGCG | GACGGCGGCG | AGCCTGCGGC | ACGCCGGCAA | ATCCGGGCCG | 120 |
| GTGGCCTCTC | CCTCTCAGAA | CACGCTGAAC | GCGCAGAATC | TGTTGAATAC | GCTGGTCGGC | 180 |
| GATATCTCAG | CGGCGGCACC | GACGGCGGCG | GCAGCGCCGG | GCGTGACGCG | GGGGCAGCAA | 240 |
| TCGCAGGAGG | GGGATTATGC | GTTGGCGCTG | TTGGCCAAGG | ACGTTACTC | ACTCAATGGC | 300 |
| CAGGGCGCCG | CCGGGTTCAA | CCGCCTGAGC | GACAGCGCGC | TGCTCGGTTT | CGGCATCGAT | 360 |
| CCCGCCAGCC | TGCACGACGC | GGGCAGCGGT | TTCCAGGCTG | GGATTTACAG | CAACGACAAA | 420 |
| CAGTATGTGT | TGGCGTTCGC | CGGCACCAAC | GACTGGCGCG | ATTGGCTGAG | CAACGTGCGG | 480 |
| CAGGCGACGG | GCTATGACGA | TGTGCAGTAC | AATCAGGCGG | TTGCCGCTGC | CAAAAGCGCC | 540 |
| AAGGCGGCCT | TCGGCGATGC | GCTGGTGATC | GCCGGCCATT | CGCTTGGCGG | TGGTCTGGCG | 600 |
| GCCACCGCCG | CGCTGGCGAC | CGGCACCGTC | GCGGTCACCT | TCAACGCGGC | CGGGGTCTCG | 660 |
| GATTACACCC | TGAATCGCCT | GGGCATCGAT | CCGGCGGCAG | CGAAGAAAGA | TGCCGAAGCC | 720 |
| GGCGGCATTC | GCCGCTACAG | CGAGCAATAT | GACATGCTGA | CCAGCACCCA | GGAGTCGACC | 780 |
| TCGCTGATCC | CGGATGCCAT | CGGCCACAAC | ATCACCCTGG | CCAACAACGA | TACCCTGACC | 840 |
| GGCATCGATG | ACTGGCGGCC | GAGCAAACAT | CTGGATCGCA | GCCTGACGGC | GCACGGCATC | 900 |
| GACAAGGTGA | TAAGCTCGAT | GGCGGAACAA | AAGCCGTGGG | AGGCGAAGGC | CAATGCC | 957 |

( 2 ) INFORMATION FOR SEQ ID NO:3:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

| CTGCAGTCCC | GGGTGTCGAC | AGATCTAGAC | ATGCATCTCG | AGTGCA | | 46 |

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:4:

CTCGAGGATC CTCCCGGGAG ATCTGCATG 29

(2) INFORMATION FOR SEQ ID NO:5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:5:

GATCCGGATC CGCAACTTCA ACTAAAAAAT TACATAA 37

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:6:

GGTACCGGAA TTCGTGCCAC TAGCAGCAGT GAC 33

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:7:

CCATGGGAGG ATCGGCGGCC GACACGGC 28

(2) INFORMATION FOR SEQ ID NO:8:

(i) SEQUENCE CHARACTERISTICS:
        (A) LENGTH: 208 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

AAGCTGGGCG GCCGCAAGCT TGCATGCCTG CAGGTCGACT CTAGAGGATC TTCCTTGGTC 60

AAATTGGGTA TACCCATTTG GGCCTAGTCT AGCCGGCATG GCGCATTACA GCAATACGCA 120

ATTTAAATGC GCCTAGCGCA TTTTCCCGAC CTTAATGCGC CTCGCGCTGT AGCCTCACGC 180

CCACATAGGG ACTGCAGAGC TCGAATTC 208

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:9:

TAATACGACT CACTATA                                                                                              17

( 2 ) INFORMATION FOR SEQ ID NO:10:

( i ) SEQUENCE CHARACTERISTICS:
     ( A ) LENGTH: 19 base pairs
     ( B ) TYPE: nucleic acid
     ( C ) STRANDEDNESS: single
     ( D ) TOPOLOGY: linear ( i i ) MOLECULE TYPE: DNA (synthetic)

( x i ) SEQUENCE DESCRIPTION: SEQ ID NO:10:

CTAGTTATTG CTCAGCGGT                                                                                            19

( 2 ) INFORMATION FOR SEQ ID NO:11:

( i ) SEQUENCE CHARACTERISTICS:
     ( A ) LENGTH: 19 base pairs
     ( B ) TYPE: nucleic acid
     ( C ) STRANDEDNESS: single
     ( D ) TOPOLOGY: linear ( i i ) MOLECULE TYPE: cDNA ( x i ) SEQUENCE DESCRIPTION: SEQ ID NO:11:

ACCGCTGAGC AATAACTAG                                                                                            19

( 2 ) INFORMATION FOR SEQ ID NO:12:

( i ) SEQUENCE CHARACTERISTICS:
     ( A ) LENGTH: 482 base pairs
     ( B ) TYPE: nucleic acid
     ( C ) STRANDEDNESS: single
     ( D ) TOPOLOGY: linear ( i i ) MOLECULE TYPE: cDNA ( x i ) SEQUENCE DESCRIPTION: SEQ ID NO:12:

ATGGCTAGCA TGACTGGTGG ACAGCAAATG GGTCGGATCG GGATCCGAAC TGCGGCTTTA        60

ATTAAAGCGA TTGATGGTGA TACGGTTAAA TTAATGTACA AAGGTCAACC AATGACATTC       120

AGACTATTAT TGGTCGACAC ACCTGAAACA AGGCATCCTA AAAAAGGTGT AGAGAAATAT       180

GGTCCTGAAG CAAGTGCATT TACCAAAAAA ATGGTAGAAA ATGCAAAGAA AATTGAAGTC       240

GAATTCGACA AAGGTCAAAG AACTGATAAA TATGGAGCTG GGCTAGCGTA TATTTATGCT       300

GATGGAAAAA TGGTAAACGA AGCTTTAGTT CGTCAAGGCT TGGCTAAAGT TGCTTATGTT       360

TACAAACCTA ACAATACACA TGAACAACAT TTAAGAAAAA GTGAAGCACA AGCGAAAAAA       420

GAGAAATTAA ATATTTGGAG CGAAGACAAC GCTGATTCAG GTCAATAATG CGAGCTCGAG       480

CT                                                                    482

( 2 ) INFORMATION FOR SEQ ID NO:13:

( i ) SEQUENCE CHARACTERISTICS:
     ( A ) LENGTH: 763 base pairs
     ( B ) TYPE: nucleic acid
     ( C ) STRANDEDNESS: single
     ( D ) TOPOLOGY: linear ( i i ) MOLECULE TYPE: cDNA ( i x ) FEATURE:
     ( A ) NAME/KEY: CDS
     ( B ) LOCATION: 215..727
     ( D ) OTHER INFORMATION: /note= "The initiation codon GTG,
       while normally translated as Valine, may also be translated as N-formyl Methionine."

( x i ) SEQUENCE DESCRIPTION: SEQ ID NO:13:

```
CGTAACCGGC  TAGTTGCGGC  CGCTGCCAGC  CATTTGCCAC  TCTCCTTTTC  ATCCGCATCG        60

GCAGGGTCAT  CCGGGCGCAT  CCACCACTCC  TGATGCAGTA  ATCCTACGGT  GCGGAATGTG       120

GTGGCCTCGA  AATTCTGTCA  TAAAGTTGTC  ACGGCCGAGA  CTTATAGTCG  CTTTGTTTTT       180

ATTTTTTAAT  GTATTTGTAC  ATGGAGAAAA  TAAA GTG AAA CAA ACG ACT ATT             232
                                         Met Lys Gln Thr Thr Ile
                                          1               5
```

| GCA | CTG | GCA | CTC | TTA | CCG | TTA | CTG | TTT | ACC | CCT | GTG | ACA | AAA | GCC | GCA | 280 |
|-----|-----|-----|-----|-----|-----|-----|-----|-----|-----|-----|-----|-----|-----|-----|-----|-----|
| Ala | Leu | Ala | Leu | Leu | Pro | Leu | Leu | Phe | Thr | Pro | Val | Thr | Lys | Ala | Ala | |
| | | | 10 | | | | | 15 | | | | | 20 | | | |

| ACT | TCA | ACT | AAA | AAA | TTA | CAT | AAA | GAA | CCT | GCG | ACT | TTA | ATT | AAA | GCG | 328 |
|-----|-----|-----|-----|-----|-----|-----|-----|-----|-----|-----|-----|-----|-----|-----|-----|-----|
| Thr | Ser | Thr | Lys | Lys | Leu | His | Lys | Glu | Pro | Ala | Thr | Leu | Ile | Lys | Ala | |
| | | 25 | | | | | 30 | | | | | 35 | | | | |

| ATT | GAT | GGT | GAT | ACG | GTT | AAA | TTA | ATG | TAC | AAA | GGT | CAA | CCA | ATG | ACA | 376 |
|-----|-----|-----|-----|-----|-----|-----|-----|-----|-----|-----|-----|-----|-----|-----|-----|-----|
| Ile | Asp | Gly | Asp | Thr | Val | Lys | Leu | Met | Tyr | Lys | Gly | Gln | Pro | Met | Thr | |
| | | 40 | | | | 45 | | | | | 50 | | | | | |

| TTC | AGA | CTA | TTA | TTG | GTC | GAC | ACA | CCT | GAA | ACA | AAG | CAT | CCT | AAA | AAA | 424 |
|-----|-----|-----|-----|-----|-----|-----|-----|-----|-----|-----|-----|-----|-----|-----|-----|-----|
| Phe | Arg | Leu | Leu | Leu | Val | Asp | Thr | Pro | Glu | Thr | Lys | His | Pro | Lys | Lys | |
| 55 | | | | | 60 | | | | | 65 | | | | | 70 | |

| GGT | GTA | GAG | AAA | TAT | GGT | CCT | GAA | GCA | AGT | GCA | TTT | ACC | AAA | AAA | ATG | 472 |
|-----|-----|-----|-----|-----|-----|-----|-----|-----|-----|-----|-----|-----|-----|-----|-----|-----|
| Gly | Val | Glu | Lys | Tyr | Gly | Pro | Glu | Ala | Ser | Ala | Phe | Thr | Lys | Lys | Met | |
| | | | | 75 | | | | | 80 | | | | | 85 | | |

| GTA | GAA | AAT | GCA | AAG | AAA | ATT | GAA | GTC | GAA | TTC | GAC | AAA | GGT | CAA | AGA | 520 |
|-----|-----|-----|-----|-----|-----|-----|-----|-----|-----|-----|-----|-----|-----|-----|-----|-----|
| Val | Glu | Asn | Ala | Lys | Lys | Ile | Glu | Val | Glu | Phe | Asp | Lys | Gly | Gln | Arg | |
| | | | 90 | | | | | 95 | | | | | 100 | | | |

| ACT | GAT | AAA | TAT | GGA | CGT | GGG | CTA | GCG | TAT | ATT | TAT | GCT | GAT | GGA | AAA | 568 |
|-----|-----|-----|-----|-----|-----|-----|-----|-----|-----|-----|-----|-----|-----|-----|-----|-----|
| Thr | Asp | Lys | Tyr | Gly | Arg | Gly | Leu | Ala | Tyr | Ile | Tyr | Ala | Asp | Gly | Lys | |
| | | 105 | | | | | 110 | | | | | 115 | | | | |

| ATG | GTA | AAC | GAA | GCT | TTA | GTT | CGT | CAA | GGC | TTG | GCT | AAA | GTT | GCT | TAT | 616 |
|-----|-----|-----|-----|-----|-----|-----|-----|-----|-----|-----|-----|-----|-----|-----|-----|-----|
| Met | Val | Asn | Glu | Ala | Leu | Val | Arg | Gln | Gly | Leu | Ala | Lys | Val | Ala | Tyr | |
| | 120 | | | | | 125 | | | | | 130 | | | | | |

| GTT | TAC | AAA | CCT | AAC | AAT | ACA | CAT | GAA | CAA | CAT | TTA | AGA | AAA | AGT | GAA | 664 |
|-----|-----|-----|-----|-----|-----|-----|-----|-----|-----|-----|-----|-----|-----|-----|-----|-----|
| Val | Tyr | Lys | Pro | Asn | Asn | Thr | His | Glu | Gln | His | Leu | Arg | Lys | Ser | Glu | |
| 135 | | | | | 140 | | | | | 145 | | | | | 150 | |

| GCA | CAA | GCG | AAA | AAA | GAG | AAA | TTA | AAT | ATT | TGG | AGC | GAA | GAC | AAC | GCT | 712 |
|-----|-----|-----|-----|-----|-----|-----|-----|-----|-----|-----|-----|-----|-----|-----|-----|-----|
| Ala | Gln | Ala | Lys | Lys | Glu | Lys | Leu | Asn | Ile | Trp | Ser | Glu | Asp | Asn | Ala | |
| | | | | 155 | | | | | 160 | | | | | 165 | | |

```
GAT TCA GGT CAA TAATGCTCAT TGTAAAAGTG TCACTGCTGC TAGTGGCAC              763
Asp Ser Gly Gln
            170
```

( 2 ) INFORMATION FOR SEQ ID NO:14:

( i ) SEQUENCE CHARACTERISTICS:
        ( A ) LENGTH: 170 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met Lys Gln Thr Thr Ile Ala Leu Ala Leu Leu Pro Leu Leu Phe Thr
 1               5                  10                  15

Pro Val Thr Lys Ala Ala Thr Ser Thr Lys Lys Leu His Lys Glu Pro
                20                  25                  30

Ala Thr Leu Ile Lys Ala Ile Asp Gly Asp Thr Val Lys Leu Met Tyr
            35                  40                  45

Lys Gly Gln Pro Met Thr Phe Arg Leu Leu Leu Val Asp Thr Pro Glu
```

-continued

|  |  |  |  |  | 50 |  |  |  | 55 |  |  |  | 60 |  |  |
|---|---|---|---|---|---|---|---|---|---|---|---|---|---|---|---|
| Thr 65 | Lys | His | Pro | Lys | Lys 70 | Gly | Val | Glu | Lys | Tyr 75 | Gly | Pro | Glu | Ala | Ser 80 |
| Ala | Phe | Thr | Lys | Lys 85 | Met | Val | Glu | Asn | Ala 90 | Lys | Lys | Ile | Glu | Val 95 | Glu |
| Phe | Asp | Lys | Gly 100 | Gln | Arg | Thr | Asp | Lys 105 | Tyr | Gly | Arg | Gly | Leu 110 | Ala | Tyr |
| Ile | Tyr | Ala 115 | Asp | Gly | Lys | Met | Val 120 | Asn | Glu | Ala | Leu | Val 125 | Arg | Gln | Gly |
| Leu | Ala 130 | Lys | Val | Ala | Tyr | Val 135 | Tyr | Lys | Pro | Asn | Asn 140 | Thr | His | Glu | Gln |
| His 145 | Leu | Arg | Lys | Ser | Glu 150 | Ala | Gln | Ala | Lys | Lys 155 | Glu | Lys | Leu | Asn | Ile 160 |
| Trp | Ser | Glu | Asp | Asn 165 | Ala | Asp | Ser | Gly | Gln 170 |  |  |  |  |  |  |